US007541141B2

(12) United States Patent
Mertz et al.

(10) Patent No.: US 7,541,141 B2
(45) Date of Patent: Jun. 2, 2009

(54) METHOD OF USING ESTROGEN-RELATED RECEPTOR ALPHA (ERRα) STATUS TO DETERMINE PROGNOSIS, TREATMENT STRATEGY AND PREDISPOSITION TO BREAST CANCER, AND METHOD OF USING ERRα AS A THERAPEUTIC TARGET FOR THE TREATMENT OF BREAST CANCER

(75) Inventors: Janet E. Mertz, Madison, WI (US); Stephen D. Johnston, Wheaton, IL (US); Richard J. Kraus, McFarland, WI (US); Eric A. Ariazi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1063 days.

(21) Appl. No.: 10/235,079

(22) Filed: Sep. 5, 2002

(65) Prior Publication Data

US 2003/0152959 A1 Aug. 14, 2003

Related U.S. Application Data

(63) Continuation-in-part of application No. 09/488,730, filed on Jan. 20, 2000, now abandoned, which is a continuation-in-part of application No. 09/031,250, filed on Feb. 26, 1998, now abandoned.

(60) Provisional application No. 60/033,808, filed on Feb. 27, 1997.

(51) Int. Cl.
*C12Q 1/68* (2006.01)
*G01N 33/53* (2006.01)
(52) U.S. Cl. .......................................... 435/6; 435/7.1
(58) Field of Classification Search .................. 436/64, 436/813; 530/399; 424/198.1, 9.34
See application file for complete search history.

(56) References Cited

U.S. PATENT DOCUMENTS 5,298,429 A 3/1994 Evans et al.

OTHER PUBLICATIONS

Ali et al., J. Mammary Gland Biology and Neoplasia, 2000, 5(3): 271-281.*
Relf et al., Cancer Research, 1997, 57:963-969.*
Utsumi et al., Int. J. Cancer: 2000, 89:39-43.*
Suzuki et al., Cancer Res. 2004, 64: 4670-4676.*
Suzuki et al., Cancer Res., 2004, 64, 4670-4676.*
Beers and Berkow, Eds. The Merk Manual of Diagnosis and Therapy: 17th Edition. Merk & Co. Whitehouse Station, N.J. 1999, pp. 973-981.
Chen, S., Zhou, D., Yang, C., and Sherman, M. Molecular basis for the constitutive activity of estrogen related receptor a-1 (ERRa-1). J Biol Chem. 16: 16. 2001.
Clark, G. M. and McGuire, W. L. Prognostic factors in primary breast cancer. Breast Cancer Res Treat. 3: S69-72, 1983.

Clark, G. M., McGuire, W. L., Hubay, C. A., Pearson, O. H., and Carter, A. C. The importance of estrogen and progesterone receptor in primary breast cancer. Prog Clin Biol Res 183-190, 1983.
Dowsett, M., T. Cooke, et al. (2000) "Assessment of HER2 status in breast cancer: why, when and how?" Eur. J. Cancer 36(2): 170-6.
Esteva, F. J., Valero, V., Booser, D., Guerra, L. T., Murray, J. L., Pusztai, L., Cristofanilli, M., Arun. B., Esmaeli, B., Fritsche, H. A., Sneige, N., Smith, T. L., and Hortobagyi, G. N. Phase II study of weekly docetaxel and trastuzumab . . . J Clin Oncol, 20: 1800-1808, 2002.
Giguere, V., Yang, N., Segui, P., and Evans, R. M. Identification of a new class of steroid hormone receptors. Nature, 331: 91-94, 1988.
Houston, S. J., Plunkett, T. A., Barnes, D. M., Smith, P., Rubens, R. D., and Miles, D. W. Overexpression of c-erbB2 is an independent marker of resistance to endocrine therapy in advanced breast cancer. Br J Cancer, 79: 1220-1226, 1999.
Hynes, N. E. and Stern, D. F. The biology of erbB-2/neu/HER-2 and its role in cancer. Biochim Biophys Acta, 1198: 165-184, 1994.
Johnston, S.D., et al., "Estrogen-related receptor 1 functionally binds as a monomer to extended half-site sequences including ones contained within estrogen-response elements," Mol. Endo. 11(3):342-352, 1997.
Klapper, L. N., Glathe, S., Vaisman, N., Hynes, N. E., Andrews, G. C., Sela, M., and Yarden, Y. The ErbB-2/HER2 oncoprotein of human carcinomas may function solely as a shared coreceptor for mutiple stroma-derived growth factors. Proc Natl Acad Sci U S A. 96: 4995-5000, 1999.
Klapper, L. N., Kirschbaum, M. H., Sela, M., and Yarden, Y. Biochemical and clinical implications of the ErbB/HER signaling network of growth factor receptors. Adv Cancer Res, 77: 25-79, 2000.
Kraus, R.J., et al. Estrogen-related receptor alpha 1 actively antagonizes estrogen receptor-regulated transcription in MCF-7 mammary cells. J Biol Chem 277: 24826-34, 2002.
Mertz, J.E., et al., "hERR1, a player in estrogen responsiveness?" Steroid/Thyroid/Retinoic Acid Gene Family, Keystone Symposium, Mar. 17-23, 1996 (Abstract).
Murray, B.S., et al., "Overexpression, purification, and functional analysis of the human androgen receptor protein," Steroid/Thyroid/Retinoic Acid Gene Family, Keystone Symposium, Mar. 17-23, 1996 (Abstract).
Nardulli, A.M., et al., "Effects of estrogen receptor truncation and mutation on DNA bending and transcription activation," Steroid/Thyroid/Retinoic Acid Gene Family, Keystone Symposium, Mar. 17-23, 1996 (Abstract).
Olayioye, M. A. Update on HER-2 as a target for cancer therapy: Intracellular signaling pathways of ErbB2/HER-2 and family members. Breast Cancer Res, 3: 385-389, 2001.
Pauletti, G., S. Dandekar, et al. (2000) "Assessment of methods for tissue-based detection of the HER-2/neu alteration in human breast cancer: a direct comparison of fluorescence in situ hybridization and immunohistochemistry" J. Clin. Oncol. 18(21): 3651-64.

(Continued)

*Primary Examiner*—Christopher H Yaen
*Assistant Examiner*—Hong Sang
(74) *Attorney, Agent, or Firm*—Quarles & Brady LLP

(57) ABSTRACT

The present invention provides that ERRα is a breast cancer biomarker of clinical course and treatment sensitivity and, itself, a target for breast cancer treatment. A high ERRα level in breast cancer indicates poor prognosis. Analyzing ERRα expression level along with the status of ERα and ErbB2 can help breast cancer patients make treatment choices. Furthermore, breast cancer can be treated by modulating ERRα activity.

16 Claims, 25 Drawing Sheets

OTHER PUBLICATIONS

Pearson, G., Robinson, F., Beers Gibson, T., Xu, B. E., Karandikar, M., Berman, K., and Cobb, M. H. Mitogen-activated protein (MAP) kinase pathways: regulation and physiological functions. Endocr Rev, 22: 153-183, 2001.

Russo, J., Hu, Y. F., Yang, X., and Russo, I. H. Developmental, cellular, and molecular basis of human breast cancer [In Process Citation]. J Natl Cancer Inst Monogr, 27: 17-37, 2000.

Santen, R. J., Song, R. X., McPherson, R., Kumar, R., Adam, L., Jeng, M. H., and Yue, W. The role of mitogen-activated protein (MAP) kinase in breast cancer. J Steroid Biochem Mol Biol, 80: 239-256, 2002.

Slamon, D. J., Leyland-Jones, B., Shak, S., Fuchs, H., Paton, V., Bajamonde, A., Fleming, T., Eiermann, W., Wolter, J., Pegram, M., Baselga, J., and Norton, L. Use of chemotherapy plus a monoclonal antibody against HER2 for metastatic . . . N Engl J Med, 344: 783-792, 2001.

Sliwkowski, M. X., Lofgren, J. A., Lewis, G. D., Hotaling, T. E., Fendly, B. M., and Fox, J. A. Nonclinical studies addressing the mechanism of action of trastuzumab (Herceptin). Semin Oncol. 26: 60-70, 1999.

Tremblay, G. B., Kunath, T., Bergeron, D., Lapointe, L., Champigny, C., Bader, J. A., Rossant, J., and Giguere, V. Diethylstilbestrol regulates trophoblast stem cell differentiation as a ligand of orphan nuclear receptor ERR beta. Genes Dev, 15: 833-838, 2001.

Vanacker, J. M., Bonnelye, E., Chopin-Delannoy, S., Delmarre, C., Cavailles, V., and Laudet, V. Transcriptional activities of the orphan nuclear receptor ERR alpha (estrogen receptor-related receptor-alpha). Mol Endocrinol, 13: 764-773, 1999.

Vanacker, J. M., et al., Cell Growth Differ. 9:1007-1014, 1998.

Vanacker, J. M., Pettersson, K., Gustafsson, J. A., and Laudet, V. Transcriptional targets shared by estrogen receptor-related receptors (ERRs) and estrogen receptor (ER) alpha, but not by ERbeta. EMBO J, 18: 4270-4279, 1999.

Vogel, C. L., Cobleigh, M. A., Tripathy, D., Gutheil, J. C., Harris, L. N., Fehrenbacher, L., Slamon, D. J., Murphy, M., Novotny, W. F., Burchmore, M., Shak, S., Stewart, S. J., and Press, M. Efficacy and safety of trastuzumab . . . J Clin Oncol, 20: 719-726, 2002.

Wiley, S. R., Kraus, R. J., Zuo, F., Murray, E. E., Loritz, K., and Mertz, J. E. (1993) Genes Dev. 7, 2206-2219.

Wright, C., Nicholson, S., Angus, B., Sainsbury, J. R., Farndon, J., Cairns, J., Harris, A. L., and Horne, C. H. Relationship between c-erbB-2 protein product expression and response to endocrine therapy in advanced breast cancer. Br J Cancer, 65: 118-121, 1992.

Xie, W., Hong, H., Yang, N. N., Lin, R. J., Simon, C. M., Stallcup, M. R., and Evans, R. M. Constitutive activation of transcription and binding of coactivator by estrogen-related receptors 1 and 2. Mol Endocrinol, 13: 2151-2162, 1999.

Yang, C. and Chen, S. Two organochlorine pesticides, toxaphene and chlordane, are antagonists for estrogen-related receptor alpha-1 orphan receptor. Cancer Res, 59: 4519-4524, 1999.

Yang, C., et al., Cancer Res. 58:5695-5700, 1998.

Yang, N., et al., "Estrogen-related receptor, hERR1, modulates estrogen receptor-mediated response of human lactoferrin gene promoter," J. Biol. Chem. 271(10):5795-5804, 1996.

Zhang, X. and Yee, D. Tyrosine kinase signalling in breast cancer: insulin-like growth factors and their receptors in breast cancer, Breast Cancer Res, 2: 170-175, 2000.

Zhang, Z. and Teng, C. T. Estrogen receptor alpha and estrogen receptor-related receptor alpha1 compete for binding and coactivator. Mol Cell Endocrinol, 172: 223-233, 2001.

Lu, et al. Transcriptional Regulation of the Estrogen-inducible pS2 Breast Cancer Marker Gene by the ERR Family of Orphan Nuclear Receptors. Cancer Research 61, 6755-6761, Sep. 15, 2001.

Greenwald, Peter. Cancer Risk Factors for Selecting Cohorts for Large-Scale Chemoprevention Trials. J Cellular Biochemistry 25S, 29-36, 1996.

Yang, N. et al. Journal of Biological Chemistry (1996), 271:5795-5804.

Johnston, S. et al. Molecular Endocrinology (1997) 11:342-352.

Leygue, E. et al. Cancer Research (1998) 58:3197-3201.

Dermer, G. et al. Bio/Technology (1994) 12:320.

Freshney, R.I., Culture of Animal Cells, A Manual of Basic Technique, Alan R. Liss, Inc., 1983, New York, p. 4.

* cited by examiner

A.
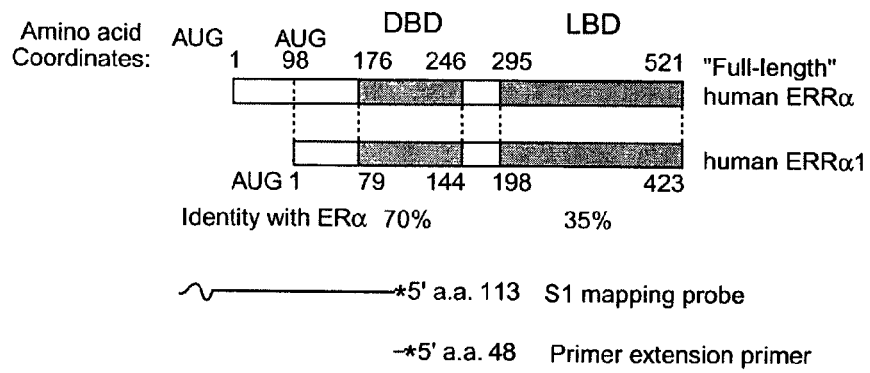
B.
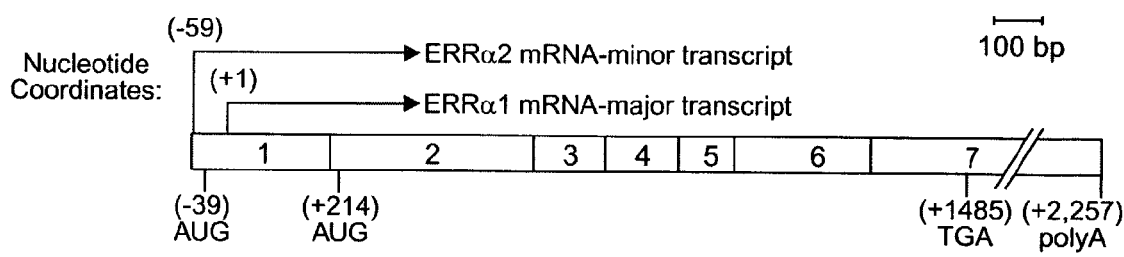
FIG. 1

| | Promoter | ERE | Oligonucleotide Sequence | el. Affinity |
|---|---|---|---|---|
| SEQ ID NO:56 | SF-1 | n.d. | GAGTTT TCAAGGTCA TGCTCAATTT | 1.0 |
| SEQ ID NO:57 | SV40+55 UP | n.d. | CGTTAAGGTT CCAAGGTCA TGGACTG | 0.8 |
| SEQ ID NO:58 | Lactoferrin | n.d. | TCCTAGGCACCT TCAAGGTCA TCTG | 0.8 |
| SEQ ID NO:59 | CYP1A2-2 | n.d. | TGAAAATTG TCAAGGTCA TCAAAAACAAGG | 0.4 |
| SEQ ID NO:60 | Prolactin D | + | AGCTAAC TAAAGGTCA CAAGCTGCTTCAGATGATC | 0.2 |
| SEQ ID NO:61 | CYP1A2-1 | n.d. | GCCAGGTGA TCAAGGTCA ACATCCACATCT | 0.1 |
| SEQ ID NO:62 | SV40+1 UP | n.d. | CTTT CAAAGGTCA TTTCAGGCCATGG | 0.1 |
| SEQ ID NO:63 | Prolactin 4 | + | AGCTAGAACC AGGTCA TCTGTCAGTCCAAAT | 0.1 |
| SEQ ID NO:64 | Vitellogenin | + | AGCTTCGAGG AGGTCA CAG TGACCT GGAGCGGATC | 0.09 |
| SEQ ID NO:65 | Creatine Kinase B | + | GGGCCCGC CCAAGGTCA GAACACCTGGGTGCTT | 0.08 |
| SEQ ID NO:66 | Prolactin 3 | + | AGCTAT AGATCATG AGGTCA TAACGATTTATGATC | 0.08 |
| SEQ ID NO:67 | Prolactin 5 | + | AGCTGCTTTGG GGTCA GAAGA GGCAGGCAGA | 0.04 |
| SEQ ID NO:69 | SV40+55 WT | n.d. | GTTA AGGTTC GT AGGTCA TGGA | 0.02 |
| SEQ ID NO:70 | SV40+1 WT | n.d. | TCAG AGGTTA TTTC AGGCCA TGGT | 0.02 |
| SEQ ID NO:71 | P450scc | n.d. | TCCAGGC TCAAGGTCA TCAGTGAGGCAAAACA | 0.02 |
| SEQ ID NO:72 | Ovalbumin D | + | CTTGTCCCAAGAAA AGGTCA GCTAAGGCTCTGCTGC | 0.008 |
| SEQ ID NO:73 | Ovalbumin B | + | AATCATTTGCTC AGGTCA CAGATGAATGTCGAA | 0.007 |
| SEQ ID NO:74 | Cathepsin D | + | GCTCGGGCCGGG GGTCA GCCGGCCAG | 0.006 |
| SEQ ID NO:75 | Prolactin P | + | GATCCACTCT AGGACA TAGTGACAAAAATGCAGCT | 0.004 |
| SEQ ID NO:76 | VLDL | + | AGCTCCTG GGTCA CTGA GCCCCTACATTT | 0.003 |
| SEQ ID NO:77 | Mutant Vitellogenin | - | AGCTTCGAGG AGaTCA CAG TGAtCT GGAGCGGATC | <0.001 |
| SEQ ID NO:78 | SV40+1 Mutant | n.d. | TCAG AGtTTA TTTC AGcCCA TGGT | <0.001 |
| | SV40+55 Mutant | n.d. | GTTA AGcTTC GT AGcTCA TGGA | <0.001 |
| Consensus: | | | 5'-TCAAGGTCA-3' | |

FIG. 5

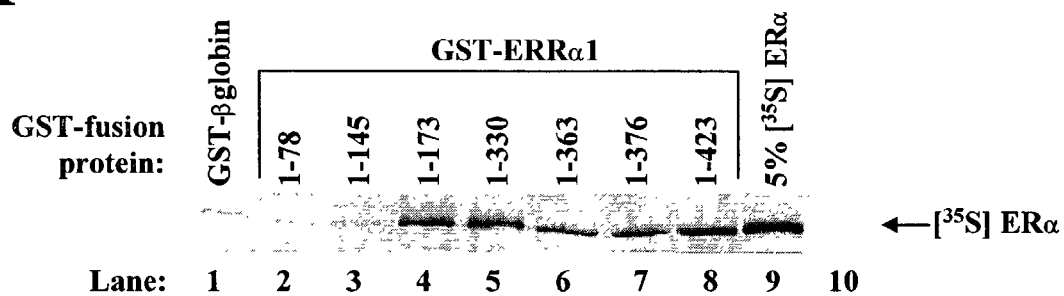
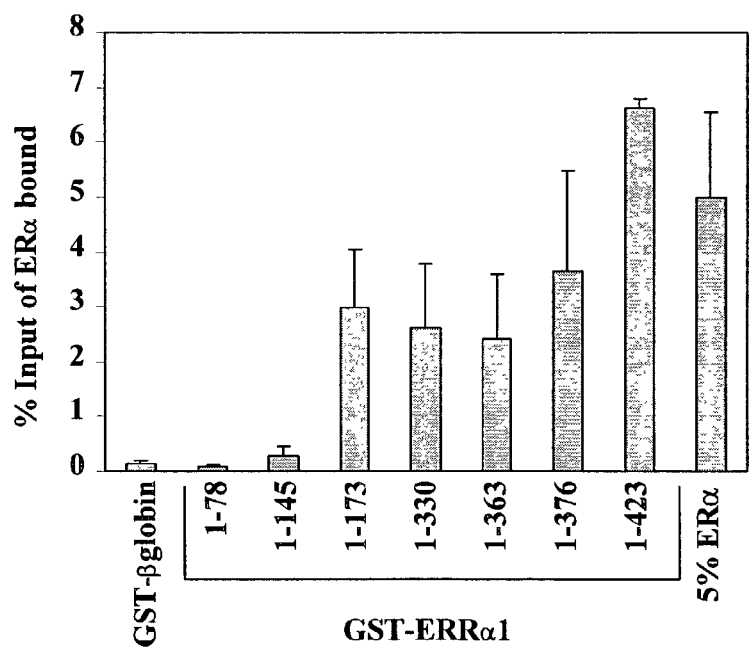
FIG. 10

NR Status

| | ER | ERRα1 | ERE-dependent transcription |
|---|---|---|---|
| 1. | Low | Low$_{rep}$ | + |
| 2. | Low | High$_{rep}$ | − |
| 3. | High | Low$_{rep}$ | + + + |
| 4. | High | High$_{rep}$ | + |
| 5. | Low | Low$_{act}$ | + + |
| 6. | Low | High$_{act}$ | + + + |

FIG. 20

SEQUENCE LISTING

```
<160> NUMBER OF SEQ ID NOS: 83

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
agcgccatgg ccagccaggt ggtgggcatt                                            30

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
gcgtctagag atgtagagag gctcaatgcc caccacc                                    37

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
cctgcaaggt cacggaggtc accccg                                                26

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
cctgcaaggt cacggtggcc acccg                                                 25

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ggagggcagg ggtgaa                                                           16

<210> SEQ ID NO 6
<211> LENGTH: 20
<212> TYPE: DNA
<213> ORGANISM: Artificial Sequence
<220> FEATURE:
```

<223> OTHER INFORMATION: Description of Artificial Sequence:
      oligonucleotide

<400> SEQUENCE: 6
ggccaggctg ttcttcttag                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
aaagtgctgg cccatttcta t                                                  21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
ccttgcctca gtccatcat                                                     19

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
taagcttagg tcacagtgac ctaagctta                                          29

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
gacttcgcca ccatgagcag ccaggtggtg gtgcattga                               39

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
ggatcctcag tccatcatgg cctcgagcat                                         30

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:

-continued oligonucleotide

<400> SEQUENCE: 12
ggatcctcac gggaagggca gtgggtcca                                               29

<210> SEQ ID NO 13
<211> LENGTH: 62
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ggatcctcag tccatcatgg cctcggccat ctccaagaac gccttgtgca tgggcacctt            60
gc                                                                           62

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
gaattcgcca ccatgaagcg cctctgcctg gtct                                        34

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
ggacccacag gatgccacac catagtggta                                              30

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
tgcaaagtct tcttcaagag gaccatcca                                               29

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:polypeptide
<220> FEATURE:
<221> NAME/KEY: UNSURE
<222> LOCATION: (2)
<223> OTHER INFORMATION: Can be any amino acid
<220> FEATURE:
<221> NAME/KEY: UNSURE
<222> LOCATION: (4)..(5)
<223> OTHER INFORMATION: Can be any amino acid

<400> SEQUENCE: 17

Leu Xaa Leu Xaa Xaa Leu

```
<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ttcccagcaa tgtcactaac tt                                              22

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
ttgaggttcc gcatacaga                                                  19

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
gtgaccgttt gggagttgat ga                                              22

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
ggctgaggga ggcgttctc                                                  19

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
gggaagaatg gggtcgtcaa a                                               21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
ctcctccctg gggtgtcaag t                                               21
```

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
gtggcactca gggagcattt a                                            21

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
tctgggactg gggaaaagg                                               19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
tgccctacag agccccaact a                                            21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gcttgcgtag ggtgccatta c                                            21

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
tgccctacga cgacaa                                                  16

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
actcctcctt ctccacctt                                               19

```
<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
ggccatcaga acggacttg                                                   19

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
gcccactacc tcccaggata                                                  20

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: unsure
<222> LOCATION: (7)..(9)
<223> OTHER INFORMATION: Can be any nucleotide

<400> SEQUENCE: 32
aggtcannnt gacct                                                       15

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
tcctaaggac tgtcaaggtc atcaaataca agg                                   33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
aaaggaactt tcccaaggtc acagagctga gct                                   33

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
```
tcgagagcag tggcgatttg tcaaggtcac acagtgag                                38

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
tccttgctaa acccaaggtc ataaatcttt tct                                     33

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
ggtgctccca cttagaggtc acgcgcggcg tcg                                     33

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
tcccttcccc ctgcaaggtc acggtggcca ccc                                     33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
tggcatattg ggtgaaggtc aagggagtgg ctt                                     33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
gctccggctc gctgaaggtc acagccgagg cga                                     33

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
gggagttcag ggtaaaggtc acggggccgg ggc                         33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
caaatttgaa actaaaggtc acaggctgct tta                         33

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 43
ctgtcggcag gaacaaggtc acccettggc gtt                         33

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
ctcccatctc acttaaggtc aaagccaggg tcc                         33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 45
gtaattgctg tacgaaggtc agaatcgcta cct                         33

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46
cctgagactc taccaaggtc agaaatgctg caa                         33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
aaaattgttt tgtctaggtc atttgcattt tca                         33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 48
caaataatgg gctgaaggtg aactatcttt act                                    33

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 49
gtaggacctg gattaaggtc aggttggagg aga                                    33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 50
atgtttggta tgaaaaggtc acattttata ttc                                    33

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 51
agaacatccc ttttaaggtc agaacaaagg tat                                    33

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 52
cctcagagtg gctcagggtc agagaaggta gag                                    33

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 53
gcgaggaaag cgtgaaggtg atttcagtta att                                    33

```
<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 54
ggtggacgct gctgaaggtg agcgagaccc cgg                              33

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 55
tgtccatttt cttctaggtc aaccccaatg gta                              33

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 56 gagttttttca aggtcatgct caattt                                     26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 57
cgttaaggtt ccaaggtcat ggactg                                      26

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 58
tcctaggcac cttcaaggtc atctg                                       25

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 59
tgaaaattgt caaggtcatc aaaaacaagg                                  30
```

```
<210> SEQ ID NO 60
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 60
agctaactaa aggtcacaag ctgcttcaga tgatc                              35

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 61
gccaggtgat caaggtcaac atccacatct                                    30

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 62
ctttcaaagg tcatttcagg ccatgg                                        26

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 63
agctagaacc aggtcatctg tcagtccaaa t                                  31

<210> SEQ ID NO 64
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 64
agcttcgagg aggtcacagt gacctggagc ggatc                              35

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 65
gggcccgccc aaggtcagaa caccctgggt gctt                               34

<210> SEQ ID NO 66
```

```
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 66
agctatagat catgaggtca taacgattta tgatc                              35

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 67
agctgctttg gggtcagaag aggcaggcag a                                  31

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 68
gttaaggttc gtaggtcatg ga                                            22

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 69
tcagaggtta tttcaggcca tggt                                          24

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 70
tccaggctca aggtcatcag tgaggcaaaa ca                                 32

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 71
cttgtcccaa gaaaaggtca gctaaggctc tgctgc                             36

<210> SEQ ID NO 72
<211> LENGTH: 34
```

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 72
aatcattttg ctcaggtcac agatgaatgt cgaa                             34

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 73
gctcgcgccc gcggggtcag cccggcccag                                  30

<210> SEQ ID NO 74
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 74
gatccactct aggacatagt gacaaaaatg cagct                            35

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 75
agctcctggg tcactgagcc ccctacattt                                  30

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 76
agcttcgagg agatcacagt gatctggagc ggatc                            35

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 77
tcagagctta tttcagccca tggt                                        24

<210> SEQ ID NO 78
<211> LENGTH: 22
<212> TYPE: DNA
```

```
<213> ORGANISM: Artificial Sequence
<220> FEATURE:
<223> OTHER INFORMATION: Description of Artificial Sequence:
      oligonucleotide

<400> SEQUENCE: 78
gttaagcttc gtagctcatg ga                                                  22

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 79
ttcctctttc agaggttatt tcaggccatg                                          30

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 80
aaggagaaag tctccaataa agtccggtac                                          30

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 81
tccgttaagg ttcgtaggtc atggactgaa a                                        31

<210> SEQ ID NO 82
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 82
aggcaattcc aagcatccag tacctgactt t                                        31

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence:polypeptide

<400> SEQUENCE: 83

Leu Phe Leu Glu Met Leu
 1               5
```

METHOD OF USING ESTROGEN-RELATED RECEPTOR ALPHA (ERRα) STATUS TO DETERMINE PROGNOSIS, TREATMENT STRATEGY AND PREDISPOSITION TO BREAST CANCER, AND METHOD OF USING ERRα AS A THERAPEUTIC TARGET FOR THE TREATMENT OF BREAST CANCER

CROSS-REFERENCE TO RELATED APPLICATION

This application is a continuation-in-part application of U.S. patent application Ser. No. 09/488,730, filed on Jan. 20, 2000, now abandoned which is a continuation-in-part application of U.S. patent application Ser. No. 09/031,250, filed on Feb. 26, 1998, now abandoned, which claims the benefit of U.S. provisional patent application Serial No. 60/033,808, filed on Feb. 27, 1997, all of which are herein incorporated by reference in their entirety.

STATEMENT REGARDING FEDERALLY SPONSORED RESEARCH OR DEVELOPMENT

This invention was made with United States Government support awarded by the following agencies: NIH, Grant Numbers CA22443, P30-CA07175 and T32-CA09681; U.S. Army Medical Research and Materiel Command Grant DAMD17-99-1-9452 and DAMD17-00-1-0668.. The United States has certain rights in this invention.

BACKGROUND OF THE INVENTION

The steroid/thyroid hormone nuclear receptor superfamily consists of a large number of transcription factors that regulate a wide variety of cellular processes (reviewed in Mangelsdorf, D. J., et al., *Cell* 83:835-839, 1995). The most highly conserved region of these proteins is their DNA binding domain (DBD) which contains two zinc finger modules. The DBD of hormone receptors interacts with a six nucleotide core recognition motif, or half-site, resembling the sequence 5'-AGGTCA-3'. Most members of the superfamily homo- and/or heterodimerize with other members of this superfamily, thus binding to two half-sites. The orientation and spacing between the half-sites provides the primary basis for specific DNA binding (reviewed in Glass, C. K., *Endocrine Rev.* 15:391-407, 1994). However, some members of this superfamily can bind to a single extended half-site version of this sequence (Scearce, L. M., et al., *J. Biol. Chem.* 268:8855-8861, 1993; Wilson, T. E., et al., *Mol. Cell. Biol.* 13:5794-5804, 1993; Harding, H. P., and Lazar, M., *Mol. Cell. Biol.* 15:4791-4802, 1995; Giguère, V., et al., *Mol. Cell. Biol.* 15:2517-2526, 1995). For example, an optimal binding site for steroidogenic factor 1 (SF-1) contains the sequence 5'-TCAAGGTCA-3' (Wilson, T. E., et al., supra, 1993).

Ligands for many members of the superfamily have been well-studied; they include the steroid hormones, thyroid hormones, retinoids and vitamin $D_3$. Other members of the superfamily have no known ligand; they are referred to as "orphan" receptors. Orphan receptors can bind DNA as heterodimers, homodimers, or monomers (reviewed in Mangelsdorf, D. J., and Evans, R. M., *Cell* 83:841-850, 1995).

The human estrogen-related receptor α (hERRα or human ERRα, officially termed NR3B1, Nuclear Receptors Nomenclature Committee, *Cell* 97:161-163, 1999; in the specification these terms are used interchangeably) is an orphan member of the steroid/thyroid hormone nuclear recepotor superfamily. cDNAs encoding portions of this protein and human ERRβ (officially termed NR3B2 (*Cell* 97:161-163, 1999); in the specification ERRβ and NR3B2 are used interchangeably) were initially isolated by a reduced-stringency screening of cDNA libraries with probes corresponding to the DBD of the human estrogen receptor α (ERα (officially termed NR3A1 (*Cell* 97:161-163, 1999)) formerly ER; in the specification, these two terms are used interchangeably) (Giguère, V., et al., *Nature* 331:91-94, 1988). Using chimeric receptors in transfected cells, Lydon, et al. (Lydon, J. P., et al., *Gene Express.* 2:273-283, 1992) demonstrated that ERRα contains a transcriptional activation domain. On the basis of amino acid sequence similarity with the receptor SF-1 in part of the DBD, Wilson, et al. (Wilson, T. E., et al., supra, 1993) predicted that ERRα might bind to the extended half-site sequence 5' TCAAGGTCA-3' recognized by SF-1. Yang, t al. (Yang, N., et al., *J. Biol. Chem.* 271:5795-5804, 1996) isolated new cDNA clones encoding most of mouse ERRα by screening a cDNA expression library for proteins capable of binding to sequences present in the promoter region of the lactoferrin gene.

Previously, Wiley, et al. reported the purification of proteins from a HeLa cell nuclear extract that bind the transcriptional initiation site of the major late promoter (MLP) of simian virus 40 (SV40) (Wiley, S. R., et al., *Genes Dev.* 7:2206-2219, 1993). These proteins, collectively referred to as IBP-s for initiator binding proteins of SV40, were shown to consist of multiple members of the steroid/thyroid hormone receptor superfamily (Wiley, S. R., supra, 1993; Zuo, F., and Mertz, J. E., *Proc. Natl. Acad. Sci. USA* 92:8586-8590, 1995). Partial peptide sequence analysis indicated that a major component of IBP-s was ERRα (Wiley, S. R., supra, 1993). Thus, at least one binding site for ERRα has been identified in the SV40 late promoter.

To identify functional activities of IBP-s, we performed a variety of genetical and biochemical experiments (Wiley, S. R., supra, 1993; Zuo, F., and Mertz, J. E., supra, 1995). The data from these experiments indicated the following: (i) The SV40 MLP contains at least two high-affinity binding sites for IBP-s situated immediately surrounding (+1 site) and approximately 55 bp downstream of (+55 site) the transcriptional start site. (ii) These high-affinity binding sites include the consensus half-site sequence 5'-AGGTCA-3'. (iii) The binding of IBP-s to these sites results in repression of transcription from the SV40 late promoter both in transfected CV-1 cells (derived from SV40's natural host) and in a cell-free transcription system. (iv) Transfection of CV-1 cells with a plasmid encoding an ERα-ERRα chimeric protein containing all but the first 38 amino acid residues of ERRα results in sequence-specific super-repression of the SV40 late promoter. Thus, ERRα likely possesses the functional activities of IBP-s.

Breast cancer afflicts one in eight women in the United States over their lifetime (Edwards, B. K., et al., *Cancer* 94:2766-2792, 2002). ERα mediates estrogen responsiveness (reviewed in Sanchez, R., et al., *Bioessays* 24: 244-254, 2002) and plays crucial roles in the etiology of breast cancer (reviewed in Russo, J., et al., *J Natl Cancer Inst Monogr.* 27:17-37, 2000). It has been developed into the single most important genetic biomarker and target for breast cancer therapy. ERα is present at detectable levels by ligand-binding and immunohistochemical assays in approximately 75% of clinical breast cancers. Selection of patients with ERα-positive breast tumors increases endocrine-based therapy response rates from about one-third in unselected patients to about one-half in patients with ERα-positive tumors (Clark, G. M. and McGuire, W. L., *Breast Cancer Res Treat.* 3:S69-72, 1983). Since expression of progesterone receptor (PgR, officially termed NR3C3 (*Cell* 97:161-163, 1999)) is dependent upon ERα activity, further selection of patients with ERα- and PgR-positive tumors enhances the breast cancer hormonal therapy response rate to nearly 80% (Clark, G. M. and McGuire, W. L., *Breast Cancer Res Treat.* 3: S69-72, 1983). Although ERβ (officially termed NR3A2 (*Cell* 97:161-163, 1999)) also mediates responses to estrogens (reviewed in Sanchez, R., et al., *Bioessays* 24: 244-254, 2002), its roles in breast cancer are not as well understood. Reports have linked ERβ expression with low tumor aggressiveness (Jarvinen, T. A., et al. *Am J Pathol.* 56:29-35, 2000) and higher levels of proliferation markers in the absence of ERα (Jensen, E. V., et al., *Proc Natl Acad Sci. USA* 98:25197-15202, 2001).

Members of the ErbB family of transmembrane tyrosine kinase receptors have been implicated in the pathogenesis of breast cancer. The members include epidermal growth factor receptor (EGFR, also HER1; ErbB1), ErbB2 (HER2; Neu), ErbB3 (HER3) and ErbB4 (HER4) (reviewed in Stern, D. F., *Breast Cancer Res.* 2:176-183, 2000). ErbB members stimulate signal transduction pathways that involve mitogen-activated protein kinase (MAPK). In response to initial binding of epidermal growth factor (EGF)-like peptide hormones, ErbB members form homodimers and heterodimers in various combinations to recruit distinct effector proteins (reviewed in Olayioye, M. A., *Breast Cancer Res.* 3:385-389, 2001). Although ErbB2 has not been demonstrated to interact directly with peptide hormones, it serves as a common regulatory heterodimer subunit with other ligand-bound ErbB members (reviewed in Klapper, L. N., et al., *Proc Natl Acad Sci. USA* 96: 4995-5000, 1999; Klapper, L. N., et al., *Adv Cancer Res.* 77:25-79, 2000). Unlike the other ErbB members, ErbB3 lacks intrinsic kinase activity and, therefore, is required to heterodimerize with other ErbB members to participate in signaling (Guy, P. M., et al., *Proc Natl Acad Sci. USA* 91: 8132-8136, 1994).

Independent overexpression of either EGFR (reviewed in Klijn, J. G., et al., *Endocr Rev.* 13:3-17, 1992) or ErbB2 (reviewed in Hynes, N. E. and Stern, D. F. *Biochim Biophys Acta.* 1198:165-184, 1994) associates with ER-negative tumor status, indicates aggressive tumor behavior, and predicts poor prognosis. Moreover, patients whose tumors coexpress both EGFR and ErbB2 exhibit a worse outcome than patients with tumors that overexpress only one of these genes (Torregrosa, D., et al. *Clin Chim Acta.* 262:99-119, 1997,Suo, Z., et al. *J Pathol.* 196:17-25, 2002). Overexpression of ErbB2, most often due to gene amplification, occurs in approximately 15-30% of all breast cancers (Slamon, D. J., et al., *Science* 235:177-182, 1987), reviewed in (Hynes, N. E. and Stern, D. F., *Biochim Biophys Acta.* 1198:165-184, 1994). Some (Wright, C., et al., *Br J Cancer* 65:118-121, 1992; Borg, A., et al., *Cancer Lett.* 81:137-144, 1994; Newby, J. C., et al., *Clin Cancer Res.* 3:1643-1651, 1997; Houston, et al., *Br J Cancer* 79:1220-1226, 1999; Dowsett, M., et al., *Cancer Res.* 61:8452-8458, 2001; Lipton, A., et al., *J Clin Oncol.* 20:1467-1472, 2002), but not all reports (Elledge, R. M., et al., *Clin Cancer Res.* 4:7-12, 1998; Berry, D., et al., *J Clin Oncol.* 18: 3471-3479., 2000.), have implicated ErbB2 in the development of resistance to antiestrogens.

ErbB2 has been targeted for development of the successful clinical agent Herceptin (trastuzumab), a recombinant humanized monoclonal antibody directed against this receptor's ectodomain (reviewed in Sliwkowski, M. X., et al., *Semin Oncol,* 26: 60-70, 1999). Herceptin has been shown to be a suitable option as a first-line single-agent therapy (Vogel, C., et al., *J Clin Oncol.* 20:719-726, 2002), but will likely prove most beneficial as an adjuvant (Slamon, D. J., et al., *N Engl J Med.* 344:783-792, 2001; Esteva, F. J., et al., *J Clin Oncol.* 20:1800-1808, 2002). Clinical trials are currently underway to evaluate the combination of Herceptin with antiestrogens as a rational approach to treating ERα-positive/ErbB2-overexpressing tumors (Lipton, A., et al., *J Clin Oncol.* 20:1467-1472, 2002). In the near future, Herceptin will also likely be evaluated in combination with the small molecule EGFR tyrosine kinase inhibitor ZD1829 (Iressa), since this ATP-mimetic has been shown to almost completely block transphosphorylation of ErbB2 via heterodimerization with EGFR in intact cells (Moulder, S. L., Yakes, et al., *Cancer Res.* 61:8887-8895, 2001) and inhibits the growth of breast cancer cell lines overexpressing both EGFR and ErbB2 (Normanno, N., et al., *Ann Oncol.* 13:65-72, 2002). Hence, a combination of ZD1829 and Herceptin may be particularly beneficial to those patients whose tumors coexpress EGFR and ErbB2.

The ability of ErbB3 and ErbB4 to predict clinical course is not as clearly recognized as that of EGFR and ErbB2. ErbB3 has been observed at higher levels in breast tumors than normal tissues, showing associations with unfavorable prognostic indicators including ErbB2 expression (Gasparini, G., et al., *Eur J Cancer* 1:16-22, 1994), lymph node-positive status (Lemoine, N. R., et al., *Br J Cancer* 66:1116-1121, 1992), and tumor size. However, it also associated with ERα-positive status, a favorable marker of hormonal sensitivity (Knowlden, J. M., et al., *Oncogene* 17:1949-1957, 1998). In stark contrast to ErbB2, higher levels of ErbB4 have been associated with ERα-positive status (Knowlden, J. M., et al., *Oncogene* 17:1949-1957, 1998; Bacus, S. S., et al., *Am J Pathol.* 148:549-558, 1996), more differentiated histotypes (Kew, T. Y., et al., *Br J Cancer* 82:1163-1170, 2000) and a more favorable outcome (Suo, Z., et al., *J Pathol.* 196:17-25, 2002).

Despite the utility of ERs and ErbB members as indicators of clinical course, there remains a great need to identify additional breast cancer biomarkers.

BRIEF SUMMARY OF THE INVENTION

The present invention discloses that ERRα is both a breast cancer biomarker and a breast cancer treatment target. In one embodiment, the present invention is a method of determining prognosis of breast cancer by determining the level of ERRα in the breast cancer tissue. A high level of ERRα indicates poor prognosis.

In another embodiment, the present invention is method of categorizing breast cancer patients for treatment purposes by determining the status of ERRα, and optionally the status of one or more of ERα, PgR, ErbB2, in the breast cancer tissue.

In another embodiment, the present invention is a method of treating breast cancer by modulating ERRα activities. If ERRα is an activator of ERE-dependent transcription in a particular breast cancer, the treatment calls for decreasing the levels or activity of ERRα. If ERRα is a repressor of ERE-dependent transcription in a particular breast cancer, the treatment calls for increasing the levels or activity of ERRα.

In another embodiment, the present invention is a method of identifying an individual for further breast cancer examination by screening for mutations in the ERRα gene.

It is an object of the present invention to identify more biomarkers and treatment targets for breast cancer.

It is an advantage of the present invention that the biomarker identified can predict prognosis and help patients make treatment choices.

Other objects, advantages, and features of the present invention will become apparent from the following detailed description of the invention.

BRIEF DESCRIPTION OF THE SEVERAL VIEWS OF THE DRAWINGS

FIGS. 1A and B are schematic diagrams of human ERRα. DBD and LBD denote the DNA binding and ligand binding domains, respectively. A, Structure of ERRα protein. ERRα1, except for lacking the first 97 amino acids, is the same as "full-length" ERRα described by Giguère, et al. (Giguère, V., et al., supra, 1988). The positions of the DBD and LBD are indicated, as are the percentages of amino acid identity between ERRα1 and ERα for each of these domains. Structures of the probes used in the experiments presented in FIG. 3 are shown at the bottom; the 5'-ends correspond to the regions encoding the amino acid residues of ERRα1, and the wavy line indicates sequences discontinuous with the ERRα cDNA. B, Structure of ERRα cDNA and its transcripts. The boxes numbered 1-7 indicate the locations and sizes of the exons. The coordinates refer to the nucleotides.

FIG. 2A represents proteins present in a HeLa cell nuclear extract and synthesized from an ERRα1 cDNA clone by in vitro transcription and translation ("TNT") that were detected by immunoblotting with an antiserum directed against GST-ERRα1$_{117-329}$.

FIG. 3A depicts S1 nuclease mapping analysis of ERRα mRNA using the probe shown in FIG. 1A.

FIG. 5 tabulates relative affinities of ERRα for DNA sequences from a variety of cellular and viral promoters.

FIG. 6A is a set of autoradiograms of DNase I footprints of GST-ERRα1 bound to the +1 and +55 sites of the SV40-MLP.

In FIG. 9A, ERα was fused to GST with ERRα1 made in reticulocyte lysates.

FIG. 10A is a radiographic image of an electrophoretic gel demonstrating that association of ERRα with ERα occurs via the C-terminus of ERRα. FIG. 10B shows the quantitation of the ERα-ERRα protein-protein interactions in FIG. 10A.

FIG. 20 is a model for ERRα modulation of estrogen responsiveness. See "Discussion" in Example 2 for details. The subscript rep denotes ERRα that is functioning as a repressor; the subscript act denotes ERRα that is functioning as an activator. Plus (+) and minus (−) symbols indicate relative levels of ERE-dependent transcription.

DETAILED DESCRIPTION OF THE INVENTION

Figure 2:
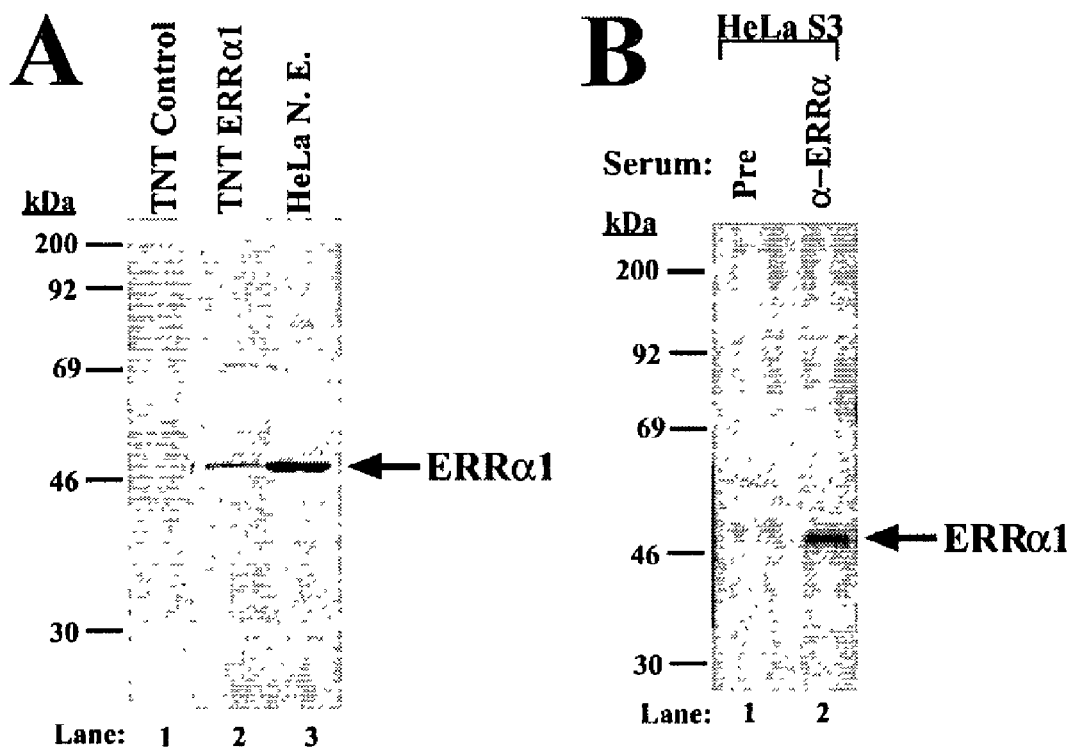
FIGS. 2A and B are radiographic images of electrophoretic gels that demonstrate the size of ERRα1 in human HeLa cells.
FIG. 2B represents HeLa cells that were metabolically labeled with [$^{35}$S]-methionine and -cysteine for 4 hours before being washed and lysed and their ERRα-related radiolabeled proteins collected by immunoprecipitation with the antisera indicated.

In the specification and claims, the term "status" of ERRα, ERα, PgR and ErbB2 refers to the "expression status" of these genes. The status can be determined either at the mRNA level or at the protein level, and either qualitatively (expressed or not expressed) or quantitatively (the level of expression). For ErbB2, the "expression status" can also be assessed directly by determining whether the gene is amplified at DNA level. There are many methods known to a skilled artisan that can be used in the present invention to determine the status of ERRα, ERα, PgR and ErbB2. As an example, the status of ERα and PgR was determined by the ligand binding assays in Example 3 below. ERRα may be expressed as one of the two isoforms, ERRα1 and ERRα2. Unless specifically mentioned, the status of ERRα in the specification and claims refers to the cumulative expression status of both ERRα1 and ERRα2. For example, to assess the ERRα expression status, primers that can amplify both ERRα1 and ERRα2 were used in Example 3 below. When the level of ERRα, ERα or ErbB2 is referred to as high or low in the specification and claims, it is measured against a median level of ERRα, ERα or ErbB2 obtained from breast cancer tissues of different patients. The more the breast cancer tissue samples of different breast cancer patients are used to establish the median level, the more accurate the median level is. Preferably, the median level is obtained from analyzing breast cancer tissues of at least 25 patients assuming an appropriate level of statistical significance can be achieved. Specifically for ErbB2, a high level or positive status can also be a status that is associated with poor prognosis as determined by the various methods described in Dowsett, M., T. Cooke, et al. (2000) "Assessment of HER2 status in breast cancer: why, when and how?" *Eur. J. Cancer* 36(2): 170-6 and Pauletti, G., S. Dandekar, et al. (2000) "Assessment of methods for tissue-based detection of the HER-2/neu alteration in human breast cancer: a direct comparison of fluorescence in situ hybridization and immunohistochemistry" *J. Clin. Oncol.* 18(21): 3651-64, both of which are herein incorporated by reference in their entirety. For example, as described in Dowsett, M., T. Cooke, et al., ErbB2 gene amplification can be considered a high level or positive status for the purpose of the present invention.

In the specification, comments and hypotheses are made on theories as to how ERRα, ERα and ErbB2 are involved in breast cancer. These theories are not intended to limit the invention.

In one aspect, the present invention is a method for determining breast cancer prognosis by analyzing the status of ERRα in the breast cancer tissue. As described in Example 3 below, a high level of ERRα in breast cancer tissue correlates with poor prognosis. This means that after diagnosis, breast cancer patients with high ERRα levels will likely have a shorter survival time than those with low ERRα levels.

In another aspect, the present invention is a method for categorizing breast cancer patients for treatment purposes. The method involves determining the status of ERRα either alone or in conjunction with ERα, PgR and/or ErbB2 in breast cancer tissues. Generally speaking, as described in Example 2 below, ERRα acts as a repressor of ERE-dependent transcription in cells that are ER-positive (e.g., breast cancer cell line MCF-7) and an activator in cells that are ER-negative (e.g., HeLa cells and breast cancer cell line SK-BR-3 (Yang, C., et al., *Cancer Res.* 58:5695, 1998)). In Example 3 described below, ERRα in breast cancer cells is shown to associate with both ER-negative status and PgR-negative status. In these breast cancer cells, ERRα levels are either similar to or higher than ERα levels, while in ER-positive and PgR-positive breast cancer cells, ERRα levels are lower than ERα levels. The term "similar" used in the specification and claims refers to the levels of ERα and ERRα in a particular tumor being within a range where they can effectively compete for binding DNA, or in practical terms, within 2-fold of each other (the ratio of one to the other is from 0.5 to 2). Likewise, when the level of one is referred to as higher or lower than that of the other in this context, we mean that the level is more than 2-fold higher or lower. Thus, when breast cancer cells lack functional ER, as in the cases of ER negative (with PgR positive or negative status) and ER positive/PgR negative cancers, and, the cancer cells have high levels of ERRα, ERRα in these cells is likely to act as an activator of ERE-dependent transcription. Patients with such breast cancer cells are unlikely to respond to hormonal blockade therapy such as tamoxifen therapy. Other therapies for breast cancer should be recommended. Hormonal blockade therapy includes the use of anti-estrogens, aromatase inhibitors and other agents that can block the production or activity of estrogen.

In breast cancer cells that contain functional ER, as in the cases of ERα positive and PgR positive cancers, and have low levels of ERRα, ERRα is likely to act as a repressor of ERE-dependent transcription. Patients with such breast cancer cells are likely to respond to hormonal blockade therapy such as tamoxifen therapy.

When the breast cancer of a patient has an ERRα level that is similar to or higher than the ERα level, the patient is unlikely to respond to hormonal blockade therapy. Other therapies for breast cancer should be considered.

In Example 3 described below, ERRα level in breast cancer cells correlates with ErbB2 level. We hypothesize that ERRα is a downstream target of ErbB2. When the breast cancer cells of a patient have a high ErbB2 level and a high ERRα level, the patient is not likely to respond to hormonal blockade therapy but is likely to respond to ErbB2-based therapy. ErbB2-based therapy includes the use of agents that either directly inhibit ErbB2 activity (anti-ErbB2 antibodies such as Herceptin and ErbB2-specific kinase inhibitors) or indirectly inhibit ErbB2 activity through heterodimerization with other ErbB members. For instance, anti-EGFR antibodies or Irressa, an EGFR kinase inhibitor, can also block ErbB2 activity. The latter does it via the formation of EGFR-ErbB2 heterodimers. When the breast cancer cells of a patient have a high ErbB2 level and a low ERRα level, the patient is not likely to respond to ErbB2-based therapy. It is questionable whether such a patient will respond to hormonal blockade therapy and hormonal blockade therapy remains an option. However, breast cancer therapies other than ErbB2-based therapy and hormonal blockade therapy should be seriously considered as well.

In another aspect, the present invention is a method of treating breast cancer by modulating ERRα activity. As described above, ERRα modulates ERE-dependent transcription. In addition, ERRα modulates transcription of at least some genes that are estrogen responsive and/or implicated in breast cancer such as pS2 (Lu, D., et al., *Cancer Res.* 61: 6755-6761, 2001), aromatase (Vanacker, J. M., et al., *Cell Growth Differ.* 9:1007-1014, 1998.), osteopontin (Bonnelye, E., et al., *Mol Endocrinol.* 11:905-916, 1997; Vanacker, J. et al., *Cell Growth Differ.* 9:1007-1014, 1998.) and lactoferrin (Yang, N., et al., *J Biol Chem.* 271:5795-5804, 1996; Zhang, Z. and Teng, C. T., *J Biol Chem.* 275:20837-20846, 2000). Thus, ERRα likely plays important roles in at least some breast cancers by modulating or substituting for ER-dependent activities.

The method of the present invention for treating breast cancer first involves determining whether ERRα is an activator or a repressor of ERE-dependent transcription in the cancer cells of a breast cancer patient. If ERRα is an activator, the breast cancer is treated by decreasing ERRα activity in breast cancer cells. If ERRα is a repressor, the breast cancer is treated by increasing ERRα activity in breast cancer cells.

Whether ERRα is an activator or a repressor of ERE-dependent transcription can be determined depending upon the presence of functional ER or the level of ERRα relative to ERα in the breast cancer. As described above, ERRα acts as a repressor of ERE-dependent transcription in cells that are ER-positive and an activator in cells that are ER-negative. In breast cancer cells, increased ERRα levels associate with ER-negative status and PgR-negative status. In these breast cancer cells, the ERRα expression level is either similar to or higher than the ERα expression level while in ER-positive and PgR-positive breast cancer cells, the ERRα level is lower than the ERα level. Accordingly, when the ERRα level is higher than the ERα level or when the ERRα level is high in ER-negative cancer cells, ERRα acts as an activator. When ERRα level is low in a functional ER-positive cancer cells, ERRα acts as a repressor. Expression levels of ErbB2 may also be used to determine whether ERRα is an activator or repressor. In breast cancer cells, high levels of ErbB2 associated with high levels of ERRα and associated with low levels of ERα. Thus, in ErbB2-positive breast cancers, ERRα is likely an activator of transcription.

In addition, whether ERRα is an activator or a repressor of ERE-dependent transcription can be determined by reporter gene assays. An ERE-based reporter plasmid can be divered in the absence and presence of an ERRα expression plasmid into the breast cancer cells of a patient and the reporter gene's expression level can be measured. Decreased or increased levels of the reporter gene (or an ERRα target gene) in the presence of the ERRα expression plasmid relative to its absence would indicate that ERRα is a repressor or activator of ERE-dependent transcription, respectively. The breast cancer cells can be biopsied from the patient and transfected with the DNA plasmid ex vivo. An example of the reporter gene assays is described in the Example 2 below.

Other methods known in the art can also be used to determine whether ERRα is an activator or a repressor of ERE-dependent transcription.

The ERRα activity in breast cancer cells can be modulated by modulating ERRα protein levels in the cells. For example, an antisense oligonucleotide can be used to inhibit the expression of ERRα. Other agents that can modulate ERRα expression can be identified by exposing a goupe of cells that express ERRα to a test agent and compairing the ERRα expression in these cells at the mRNA level or at the protein level to control cells that are not exposed to the agent. ERRα expression can also be measured indirectly by using reporter plasmids whose expression is altered by ERRα.

In addition, the ERRα activity in breast cancer cells can be modulated via gene therapy by introduction of exogenous variant ERRα proteins with altered activities (dominant-negative ERRα). In Example 2 below, a mutant form of ERRα incabable of activating transcription (ERRα1$_{L413a/L418A}$) was transfected into MCF-7 cells and repressed ERE-dependent transcription better than wild-type ERRα. Therefore, such a mutant ERRα can be used to specifically inhibit endogenous ERRα transcriptional activity as well as ER-mediated ERE-dependent activity.

One can also use an ERRα agonist or antagonist to modulate ERRα activity. The synthetic estrogen diethylstilbestrol is an ERRα antagonist. Other ERRα agonists or antagonists can be screened by exposing ERRα to a test agent and determining whether the test agent binds to ERRα. There are many ways that this can be done. For example, a test agent can be labeled and ERRα can be exposed to the test agent, washed and purified. If the label is detected on the purified ERRα, then the test agent has bound to ERRα. Once a test agent is determined to be capable of binding to ERRα, whether the agent can activate or inhibit ERRα activity can be determined. For example, a reporter for ERRα activity can be introduced into host cells along with an ERRα expression plasmid. The cells can then be exposed to the test agent and the ERRα activity in these cells can be compared to that of control cells that are not exposed to the agent. As an example, a system for analyzing ERRα activity as a regulator of ERE-dependent transcription, either as a repressor or activator, is described in Example 2 below.

In a more general manner, cells that carry a reporter for ERRα activity can be used directly to screen for agents that can modulate ERRα activity by exposing the cells to a test agent and comparing the ERRα activity in these cells to control cells that are not exposed to the agent.

ERRα activity can also be inhibited by an ERRα antibody (either monoclonal or polyclonal), which can be readily generated by a skilled artisan. Encapsulating liposomes or other similar technology can be used to deliver anti-ERRα antibodies into cells. Alternatively, recombinant DNAs expressing an anti-ERRα antibody (such as in the form of a single-chain antibody fragment) can be introduced into cells via gene therapy methodologies.

In another aspect, the present invention is a method of identifying human candidates for further breast cancer examination by screening for mutations in ERRα against a reference ERRα sequence or by screening for an aberrantly spliced mRNA variant of ERRα. For example, the National Center for Biotechnology Information (NCBI) Reference Sequence entry for ERRα, NM_004451, can serve as a reference ERRα sequence. As mentioned above, ERRα likely plays important roles in human breast cancer. A mutation in ERRα or the existence of an aberrantly spliced mRNA variant of ERRα may predispose a human being to breast cancer. Accordingly, an individual who carries a mutated ERRα or an aberrantly spliced mRNA variant of ERRα should be monitored closely for breast cancer development.

The invention will be more fully understood upon consideration of the following non-limiting examples.

EXAMPLE 1

We (see Johnston, S. D., Ph.D. Thesis, Activation and repression of the SV40 late promoter, University of Wisconsin-Madison, 1996; Johnston, S. D., et al., supra, 1997, see below) and others (Yang, N., et al., *J. Biol. Chem.* 271-5795-5804, 1996) have found that a 53-kD protein, called ERRα1, is a major isoform expressed in vivo from the ERRα gene. Using this biologically relevant, non-chimeric, recombinant human ERRα1 protein, we demonstrate here that ERRα protein can, indeed, bind with high-affinity the DNA binding site containing 5'-TCAAGGTCA-3'. We also report the development of in vitro and in vivo functional assays for ERRα activity. Lastly, binding sites for ERRα are identified in cellular promoters, some of which contain functional estrogen-response elements (EREs) and exhibit altered expression in some breast cancers, and ERRα is shown to bind directly ERα. We predict that ERRα can play roles in the response of some genes to estrogen via protein-protein interactions with ER or competition with ER for binding to EREs and regulating transcription.

Materials and Methods

Oligonucleotides and recombinant plasmids: Oligonucleotides were synthesized by Integrated DNA Technologies (Coralville, Iowa) or GIBCO BRL Life Technologies (Gaithersburg, Md.). Complementary strands were annealed by heating to 95° C. for 5 minutes and cooling to room temperature over 2 hours. Annealed oligonucleotides were purified with a non-denaturing 15% polyacrylamide gel (Sambrook, J., et al., Molecular cloning: A laboratory manual, 2nd ed., Cold Spring Harbor Laboratory Press, Cold Spring Harbor, N.Y., 1989). Plasmid pRSV-ER-hERRα directs the expression of a fusion protein consisting of the first 44 amino acids of ERα and all but the first 38 amino acid residues of the previously published ERRα sequence constructed from putatively overlapping cDNA clones (Zuo, F., and Mertz, J. E., supra, 1995). "Full-length" ERRα cDNA was RT-PCR-amplified out of HeLa cell mRNA and inserted in the KpnI-to-HindIII sites of pSP72 (Promega) to generate pSP72-hERRα. Plasmid pSP72-hERRα1 was generated by PCR-amplification of a portion of the "full-length" ERRα coding sequence (using the 5' primer AGCGCC ATGGCCAGCCAGGTGGTGGGCATT (SEQ ID NO:1), with the translation start codon for ERRα1 (underlined) and ligation back into NcoI- and XmaI-cut pSP72-hERRα. Plasmid pGEX-hERRα1 was constructed similarly. The plasmids directing the expression of GST COUP-TF1 and GST-βglobin1-123 have been described previously (Johnston, S. D., et al., *J. Virol.* 70:1191-1202, 1996). The NaeI fragment of the ERRα cDNA was cloned into a pGEX-2T vector (Pharmacia) to generate pGEX-hERRα1$_{17-329}$ The plasmid pGEX-ER was constructed by subcloning the ERα-encoding EcoRI fragment of pHEGO, a gift of P. Chambon (Tora, L., et al., *EMBO J.* 8:1981-1986, 1989), into pGEX. Plasmids pGEX-TFIIB and phIIB (Ha, I., et al., *Nature* 352:689-695, 1991) were gifts from D. Reinberg. Plasmid pRSV-hERRα1 was generated by subcloning the sequences coding for ERRα1 from pGEX-hERRα1 into pRSV-0+, a derivative of pRSV-0 (Zuo, F., and Mertz, J. E., supra, 1995) containing a functional SV40 origin of DNA replication.

Cell culture and transfections: CV-1PD cells and COS cells were grown in Dulbecco's modified Eagle's medium (DMEM) supplemented with 5% and 10% fetal bovine serum (FBS), respectively. HeLa S3 cells were grown in RPMI-1640 with 2 mM glutamine and 10% FBS. All media were supplemented with penicillin and streptomycin. Co-transfections were performed by a modification of the DEAE-dextran/chloroquine procedure as described (Good, P. J., et al., *J. Virol.* 62:563-571, 1988) or the calcium phosphate co-precipitation method. SV40 viral sequences were excised from the plasmid-cloning vector and ligated to form monomer circles before transfection.

Recombinant proteins and antiserum: Recombinant GST-fusion proteins were purified essentially as described (Johnston, S. D., et al., supra, 1996). HeLa cell nuclear extract was prepared as previously described (Wiley, S. R., et al., supra, 1993; Dignam, J. D., et al., *Methods Enzymol.* 101: 582-598, 1983). In vitro transcribed and translated ("TNT") proteins were synthesized with a rabbit reticulocyte lysate (Promega) and [$^{35}$S]-methionine and cysteine (Tran$^{35}$S Label; ICN) following the manufacturer's suggested protocol. Recombinant ERα and ERRα1 were synthesized in COS cells transfected with plasmids encoding these proteins. A polyclonal antiserum was raised in a New Zealand white rabbit against GST-ERRα1$_{17-329}$. Molecular mass determination was performed with Combithek (Boehringer Mannheim) and Mark 12 (Novex) calibration proteins as standards.

Metabolic labeling and immunoprecipitation: Cells were metabolically labeled when approximately 80% confluent by incubation for 4 hours with medium containing [$^{35}$S]-methionine and -cysteine (250 mCi Tran$^{35}$S Label; ICN) as described (Johnston, S. D., supra, 1996). Protein lysates were prepared (Johnston, S. D., supra, 1996) and were pre-cleared by incubation for 1 hour with protein A-agarose (Santa Cruz Biotech). The resulting supernatant was incubated for 1 hour on ice with 1 ml of anti-GST-ERRα1$_{17-329}$ serum or preimmune serum from the same animal. Afterward, protein A-agarose was added and the lysate was incubated for 1 hour at 4° C. The beads were washed three times and the proteins were eluted by boiling in 2×SDS loading buffer. The radiolabeled proteins were separated in a 10% SDS-PAGE gel and detected by fluorography.

S1 nuclease mapping and primer extension analysis: Total cellular RNA was prepared by lysis of the cells in SDS and treatment with Proteinase K. Nucleic acids were extracted and DNA was degraded by treatment with DNase I (Zuo, F., supra, 1995). Poly(A)+ HeLa S3 RNA was prepared with an mRNA Separator kit (Clontech). The S1 nuclease mapping probe consisted of the PvuII-to-HpaI fragment of pSP72-hERRα (FIG. 1); it was gel-purified and end-labeled with [γ-$^{32}$P]ATP using T4 polynucleotide kinase (Ausubel, F. M., et al., "Current Protocols in Molecular Biology," John Wiley and Sons, Inc, New York, N.Y., 1994). The hybridization and S1 nuclease digestion reactions were performed essentially as described (Hertz, G., and Mertz, J. E., *Virology* 163:579-590, 1988). The resulting protected fragments were separated by electrophoresis through a 7M urea, 5% polyacrylamide gel.

Primer extension analyses were performed essentially as described (Good, P. J., et al., supra, 1988) using the 5'-end labeled oligonucleotide 5'-GCGTCTAGAGATGTA-GAGAGGCTCAATGCCCACCACC-3' (SEQ ID NO:2) as primer (FIG. 1). The resulting DNAs were resolved in a 7 M urea, 8% polyacrylamide gel.

Quantitative gel-mobility-shift assays: DNA binding was assayed in 20 μl of a buffer containing 10 mM HEPES (pH 7.5), 2.5 mM MgCl$_2$, 50 μM EDTA, 1 mM dithiothreitol, 6% glycerol and 100 ng/μl of poly(dI-dC)·poly(dI-dC). Competition binding assays included unlabeled competitor oligonucleotide as well. 250 pg of 5'-end-labeled, double-stranded oligonucleotide (approximately 5×10$^4$ cpm) was incubated with approximately 0.85 ng of GST-ERRα1 or GST-βglobin1-123. Supershift assays contained 1 μl of a 1:10 dilution of whole antiserum. All components were mixed prior to the addition of protein. The final mixtures were incubated on ice for 15 minutes, followed by 25° C. for 15 minutes prior to separation by electrophoresis at 4° C. for 2 hours through a non-denaturing 4% polyacrylamide gel at 160 volts. Quantitation was performed with a PhosphorImager (Molecular Dynamics). The relative affinities of different sequences for binding by the protein were determined from the moles of unlabeled competitor oligonucleotide needed to reduce the fraction of probe shifted to 50%.

For assays involving ERα, 1-2 μl of whole cell extract containing ERα (500-700 ng protein) were incubated on ice for 15 minutes in a reaction mixture containing 20 mM HEPES (pH 7.4), 1 mM DTT, 100 mM NaCl, 10% glycerol (v/v), 100 μg/ml BSA, 4 μg poly(dI-dC)·(dI-dC) in 16 μl. Radiolabeled probe DNA (20,000-50,000 cpm, 0.2-0.5 ng) was added and incubated for 20 minutes at room temperature. The samples were loaded directly on a pre-run 4% acrylamide (39:1 acrylamide/bis-acrylamide) non-denaturing gel with 0.5×TBE as the running buffer. The gels were run in the cold room for 2 hours at 180 V and dried onto filter paper.

Footprinting: The probes used in the DNase I footprinting assays were PCR-amplified DNA corresponding to SV40 nt 272-446. Sense and anti-sense probes were created by 5'-end-labeling one of the PCR primers. The PCR products were gel-purified before use. Approximately 30 ng of GST-ERRα1 was incubated 20 minutes at room temperature with 3-5×10$^5$ cpm of the probe in 50 mM HEPES (pH 7.6), 6 mM MgCl$_2$, 500 μM EDTA, 20% glycerol, 8% polyethylene glycol and 0.1 mg/ml poly(dI-dC)·poly(dI-dC). One μl of a 1:50 dilution of DNase I was added and the incubation was continued for 1 minute. The reactions were electrophoresed through a non-denaturing 4% polyacrylamide gel. The protein-DNA complexes and unbound DNA were visualized by autoradiography and excised and eluted from the gel. The DNAs were purified by phenol:chloroform extraction and ethanol precipitation. Equal counts from the unbound and bound complexes were loaded onto a 7M urea, 6% denaturing polyacrylamide gel. After electrophoresis, the gel was dried and exposed to x-ray film.

Hydroxyl radical footprinting was performed essentially as described by Tullius and Dombroski (Tullius, T. D., and Dombroski, B. A., *Proc. Natl. Acad. Sci. USA* 83:5469-5473, 1986). The probes were synthesized by PCR-amplification from an SV40 mutant, pm322C, containing an ERRα binding site only at +55 (Wiley, S. R., et al., supra, 1993). Approximately 1×10$^7$ cpm of this probe was cleaved prior to use in the footprinting reactions. Thereafter, the DNAs were treated essentially as described above.

Cell-free transcription: Cell-free transcription assays were performed as described (Wiley, S. R., et al., supra, 1993; Zuo, F., and Mertz, J. E., supra, 1995). In brief, 200 ng of circular, plasmid SV40 DNA as template was incubated for 15 minutes at 4° C. with approximately 37 ng of the indicated fusion protein, followed by 15 minutes at 25° C. before addition of the nuclear extract. The resulting SV40 transcripts were analyzed by primer extension (Zuo, F., and Mertz, J. E., supra, 1995; Good, P. J., et al., supra, 1988) with synthetic oligonucleotides corresponding to SV40 nt 5178-5201 and nt 446-422 serving as primers for the detection of the early and late RNAs, respectively.

Binding assays: Protein-protein associations were assayed essentially as described (Johnston, S. D., et al., supra, 1996). Briefly, bacterial lysate containing approximately 4 pmol of the GST fusion protein was thawed on ice and mixed with GSH-Sepharose at 4° C. for at least 30 minutes. The beads were washed twice at 4° C. with 500 μl NETN buffer, resuspended in 50 μl NETN buffer, mixed at 4° C. for at least 1 hour with the test protein (typically in 0.2-2 μl of reticulocyte lysate), and washed three times at 4° C. with NETN buffer. The bound proteins were eluted from the beads by boiling in SDS loading buffer and resolved by SDS-PAGE. For the experiment shown in FIG. 9B, the lysates were treated with 50 mg/ml ethidium bromide before use in this binding assay as described (Lai, J.-S., and Herr, W., supra, 1992). The gels were stained with Coomassie brilliant blue, destained, equilibrated in water and treated with 1M salicylic acid for 30 minutes before being dried and exposed to x-ray film.

Results

Human ERRα1: The original sequence of human ERRα cDNA was deduced from putatively overlapping cDNA clones (Giguère, V., et al., supra, 1988). It encodes a 521-amino acid protein with an apparent molecular mass of 63 kDa by SDS-PAGE (Johnston, S. D., supra, 1996). We failed by pulse-labeling/immunoprecipitation and immunoblotting techniques to find a protein of this size in any of numerous natural sources that cross-reacted with our human ERRα-specific antiserum; instead, we identified a faster-migrating protein (Johnston, S. D., supra, 1996; see below). We hypothesized that this naturally existing protein is an isoform encoded by the ERRα gene in which translation initiates at the second methionine codon, corresponding to amino acid residue 98 in the published sequence (see FIG. 1). This product of the human ERRα gene is named ERRα1.

Figure 3:
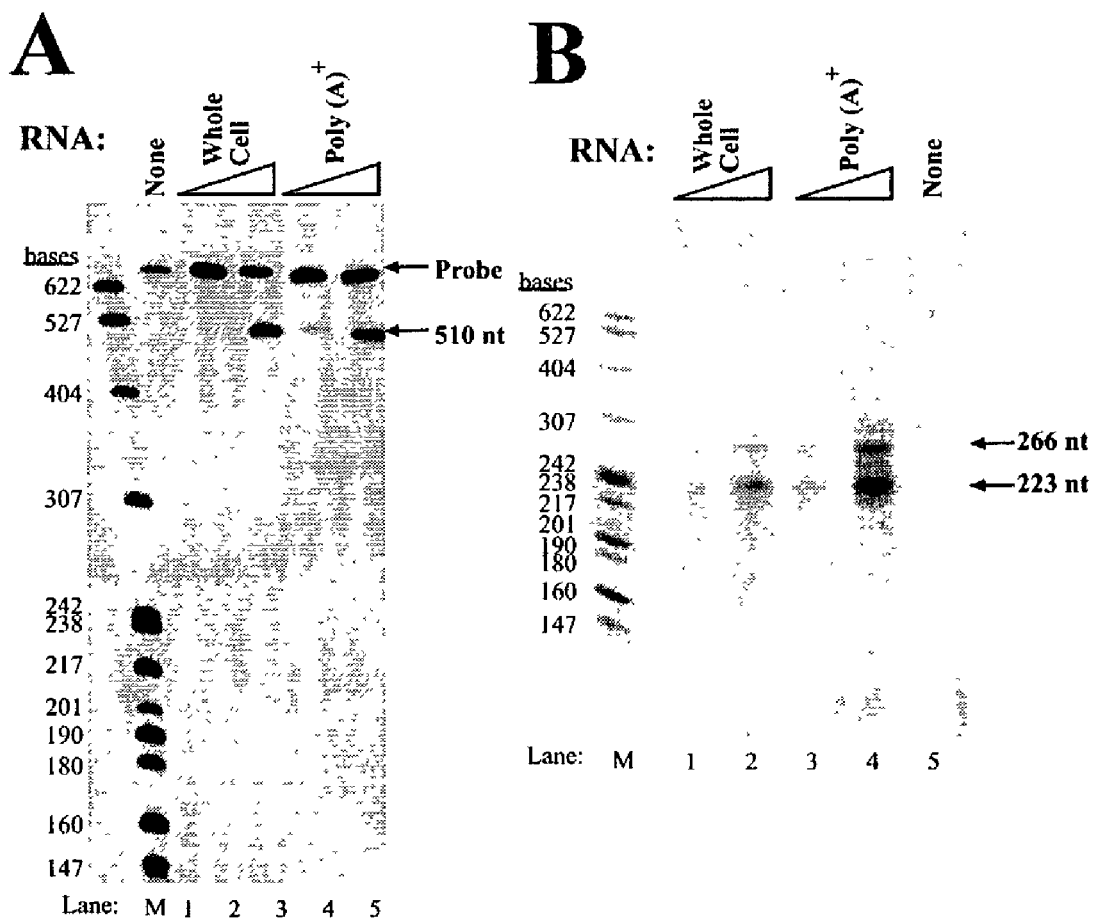
FIGS. 3A and B are radiographic images of electrophoretic gels displaying the major species of ERRα mRNA present in HeLa cells.
FIG. 3B depicts primer extension analysis of ERRα mRNA using the probe shown in FIG. 1A.

FIG. 1A is a schematic diagram of human ERRα1. Human ERRα1 is the same as human ERR1 described by Giguère, et al. (Giguère, V., et al., supra, 1988), except for lacking the first 97 amino acids and having corrections in the amino acid sequence from the one originally reported (Yang, N., et al., supra, 1996 reports the corrected sequence. Yang, et al. is incorporated by reference as if fully set forth herein). The positions of the DNA binding domain (DBD) and ligand binding domain (LBD) are indicated, as are the percentages of amino acid identity between human ERRα1 and human ERRα for each of these domains. Structures of the probes used in the experiments presented in FIG. 3 are shown at the bottom; the 5'-ends correspond to the regions encoding the amino acid residues of ERRα1 and the wavy line indicates sequences discontinuous with the ERRα cDNA.

To test this hypothesis, a polyclonal antiserum against amino acid residues 17-329 of ERRα1 was used in immunoblotting experiments to compare the ERRα proteins present in a HeLa cell nuclear extract with ERRα1 produced by in vitro transcription and translation in a rabbit reticulocyte lysate ("TNT").

FIG. 2 demonstrates the size of human ERRα1 in human cells. FIG. 2(A) represents proteins present in a HeLa cell nuclear extract (lane 3) and synthesized from a human ERRα1 cDNA clone by in vitro transcription and translation ("TNT") (lane 2) that were detected by immunoblotting with an antiserum directed against GST-ERRα1$_{117-329}$. The TNT control (lane 1) was unprogrammed reticulocyte lysate. FIG. 2(B) represents HeLa cells that were metabolically labeled with [$^{35}$S]-methionine and -cysteine for 4 hours before being washed and lysed. Radiolabeled proteins were immunoprecipitated with a pre-immune serum (lane 1) or a GST-ERRα1$_{117-329}$ antiserum (lane 2) and detected by fluorography. The molecular mass markers used here had been conjugated to a colored moiety and, thus, were not precise determinants of molecular mass.

The predominant protein found in each sample co-migrated (FIG. 2A). Careful measurements of its mobility indicated that its apparent molecular mass is 53 kDa (data not shown). A second, less abundant, 58-kDa protein that reacted with our antiserum was also observed in variable quantities in some preparations of HeLa cell nuclear extract (data not shown).

The sizes of the in vivo-synthesized human ERRα1 proteins were also determined by metabolic labeling of HeLa cells with [$^{35}$S] methionine and cysteine, followed by immunoprecipitation. Again, a 53-kDa protein was identified (FIG. 2B); no larger protein was ever observed. This 53 kDa protein was also observed in eight other mammalian cell lines derived from a variety of tissues (CV-1PD, MCF7, T47D, Hs1, Hs181, RL95-2, HepG2, and αE6/E7-2) (Johnston, S. D., supra, 1996) and was found to have a half-life of 10-12 hours (Johnston, S. D., supra, 1996). Thus, we conclude that ERRα1 corresponds to the authentic, major isoform synthesized from the ERRα gene in vivo.

To confirm this finding, we also analyzed the location of the 5'-ends of endogenous ERRα mRNAs present in human HeLa cells by S1 nuclease mapping with the probe shown in FIG. 1. FIG. 3 is a photograph of an electrophoretic gel displaying the major species of ERRα mRNA present in HeLa cells encodes ERRα1, not "full-length" ERRα. FIG. 3(A) depicts S1 nuclease mapping analysis of ERRα mRNAs. The structures of the 5'-ends of the ERRα mRNAs accumulated in HeLa cells were analyzed by S1 nuclease mapping with the probe shown in FIG. 1A. The reaction mixtures contained no RNA (lane 1), 9 μg whole cell RNA (lane 2), 54 μg whole cell RNA (lane 3), 0.6 μg poly (A)+ RNA (lane 4), or 5.8 μg poly (A)+ RNA (lane 5). M, MspI-cut pBR322 DNA. FIG. 3(B) depicts primer extension analysis of human ERRα mRNA. A synthetic oligonucleotide, 5'-end-labeled 48 nt 3' of the ERRα1 initiation codon, was hybridized with the RNA and extended with AMV reverse transcriptase. The products were resolved by denaturing polyacrylamide gel electrophoresis and visualized by autoradiography. Samples contained either 12 μg whole cell RNA (lane 1), 60 μg whole cell RNA (lane 2), 3.6 μg poly (A)+ RNA (lane 3), 18 μg poly (A)+ RNA (lane 4), or no RNA (lane 5). M, MspI-cut pBR322 DNA.

Whereas RNA that could encode "full-length" ERRα would be expected to protect 634 nt of this probe, we observed a protected fragment only 510 nt in length (FIG. 3A). Thus, most of the ERRα mRNA accumulated in HeLa cells was discontinuous with the deduced ERRα sequence described by Giguère, et al. (Giguère, V., et al., supra, 1988) at approximately nt +180 relative to the AUG codon presumed to be used for the synthesis of "full-length" ERRα.

To determine whether this discontinuity corresponded to the true 5'-end of the mRNA or a splice site, we also examined the structure of the 5'-end of the RNA by primer extension analysis using a primer that could hybridize to the RNA just 3' of the AUG codon presumed to be used for the synthesis of ERRα1 (FIG. 1): two major bands, 223 and 266 nt in length, were observed (FIG. 3B). The 223-nt band corresponded well with the major 5'-end identified by S1 nuclease mapping. It also corresponded to the 5'-end of a ERRα1 cDNA isolated by Yang, et al. (Yang, N., et al., supra, 1996) from a human endometrium carcinoma cell line. Thus, it is highly likely that this is the location of the 5'-end of the major species of ERRα mRNA that accumulates in at least some human cell lines. Because the first AUG codon in this mRNA is the codon present at the amino-terminus of ERRα1, this mRNA likely encodes ERRα1 protein, but cannot encode "full-length" ERRα. The minor, 266-nt band observed by primer extension analysis also cannot correspond to an mRNA encoding "full-length" ERRα. Thus, we conclude that the major, ERRα-encoded protein which accumulates in HeLa cells is probably identical in primary structure to the ERRα1 protein depicted in FIG. 1A. However, other isoforms synthesized from the human ERRα gene may also exist in minor quantities (e.g. ERRα2; see FIG. 1B) or in different tissues or times during development.

Figure 4:
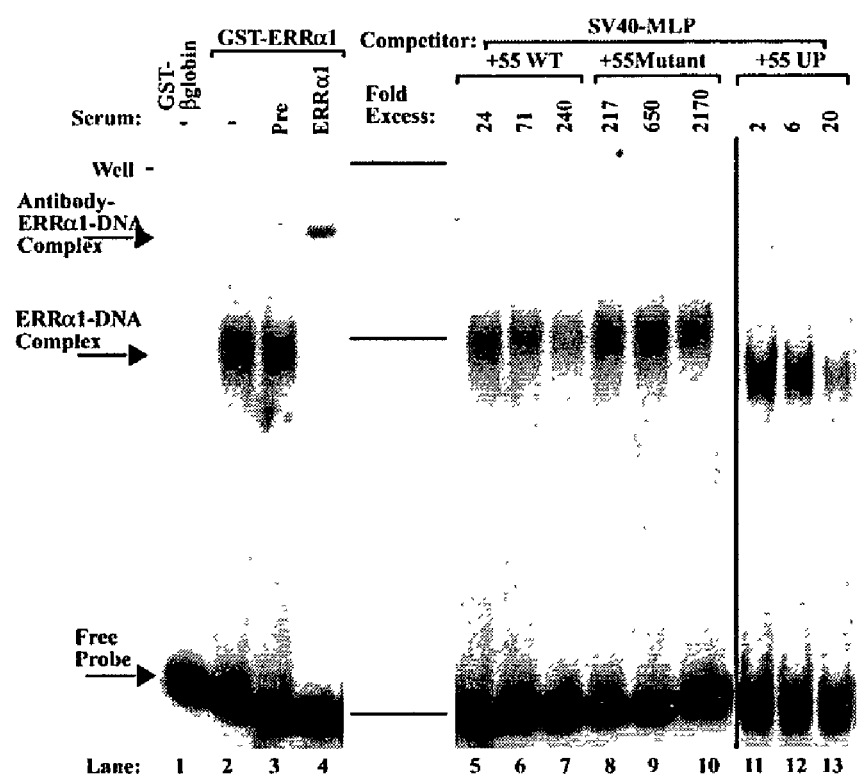
FIG. 4 is a radiographic image of gel-mobility-shift assays showing sequence-specific binding of recombinant ERRα1 protein.

DNA binding by ERRα: Because ERRα was initially cloned on the basis of amino acid similarity with ERα, the DNA sequence(s) it binds was unknown. We, therefore, investigated the DNA binding properties of ERRα. Since Wilson, et al. (Wilson, T. E., et al., supra, 1993) hypothesized that ERRα might bind a DNA sequence similar to the one bound by SF-1, we first looked for binding by a gel-mobility-shift assay with a probe consisting of a double-stranded synthetic oligonucleotide containing the high-affinity SF-1 binding site sequence, 5'-TCAAGGTCA-3'. FIG. 4 is a photograph of gel-mobility-shift assays showing sequence-specific binding of recombinant human ERRα1 protein. Bacterially expressed GST-βglobin$_{1-123}$ (lane 1) and GST-ERRα1 (lanes 2-13) were incubated with radioactive, double-stranded SF-1 oligonucleotide as a probe. A pre-immune (lane 3) or polyclonal anti-GST-ERRα1$_{17-329}$ (lane 4) serum was added to some of the binding reactions before the addition of recombinant protein. Lanes 5-13 show quantitative, competition gel-mobility-shift assays in which the indicated molar fold excesses of the indicated unlabeled, double-stranded oligonucleotides were included in the reactions as competitors. The sequences of one strand of each of these oligonucleotides are shown in FIG. 5.

GST-ERRα1 was, indeed, found to bind this SF-1 probe (FIG. 4, lane 2). Incubation with our polyclonal anti-ERRα serum resulted in both the supershifting of a portion of this ERRα-DNA complex and the prevention of the formation of another portion of it (FIG. 4, lane 4 vs. 3). Thus, we conclude that ERRα binds specifically to the high-affinity binding site of SF-1.

To better understand the range of DNA sequences recognized by ERRα, we tested the ability of ERRα to bind to sequences from a variety of promoters, including many hormone response elements (HREs). Because prior work from our laboratory indicated that ERRα probably binds to two sites in the SV40-MLP, the +1 and +55 sites (Wiley, S. R., et al., supra, 1993; Zuo, F., and Mertz, J. E., supra, 1995), we tested the affinity of ERRα for these sites relative to the SF-1 site using a quantitative, competition gel-mobility-shift assay (FIG. 4, lanes 5-13): an oligonucleotide corresponding to the +55 site of the wild-type (WT) SV40-MLP competed moderately well (lanes 5-7); one corresponding to a mutant that binds IBP-s better that WT competed very well (lanes 11-13); and one corresponding to a mutant that fails to bind IBP-s did not compete (lanes 8-10) (summarized in FIG. 5).

Multiple sequences from a variety of cellular promoters were tested likewise (Johnston, S. D., supra, 1996; data not shown), including ones known to function as EREs since the DBDs of ERRα and ERα have 70amino acid identity (Giguère, V., et al., supra, 1988; Yang, N., et al., supra, 1996). These data are summarized in FIG. 5. FIG. 5 tabulates relative affinities of ERRα for DNA sequences from a variety of cellular and viral promoters. Quantitative, competition gel-mobility-shift assays were performed as described in the legend to FIG. 4 with double-stranded oligonucleotides corresponding to the sequences shown in the third column of the table serving as the unlabeled competitors. The fourth column indicates the affinities of ERRα for the competitor sequences relative to the SF-1 probe; these values were determined experimentally from the fold molar excess of competitor oligonucleotide needed to reduce by 50% the fraction of probe shifted. The second column indicates the cases in which these sequences are known from the scientific literature to contain functional estrogen-response elements. N.d.=not determined. The complete sequence of the lactoferrin oligonucleotide is reported as the FP1 sequence in Yang, et al. (Yang, N., et al., supra, 1996).

Some of the EREs tested (e.g., prolactin D, vitellogenin) did, indeed, bind ERRα with moderately high relative affinities (see also below). Thus, some EREs contain binding sites for ERRα.

By comparing the sequences that bound ERRα well with those that bound it poorly or not at all, we deduced that a high-affinity, consensus DNA-binding site for ERRα is 5' TCAAGGTCA-3'. However, some of the oligonucleotides containing this consensus sequence (e.g., P450 scc) did not bind ERRα well; thus, bases beyond the 9-bp consensus sequence also affect the binding affinity.

Figure 6:
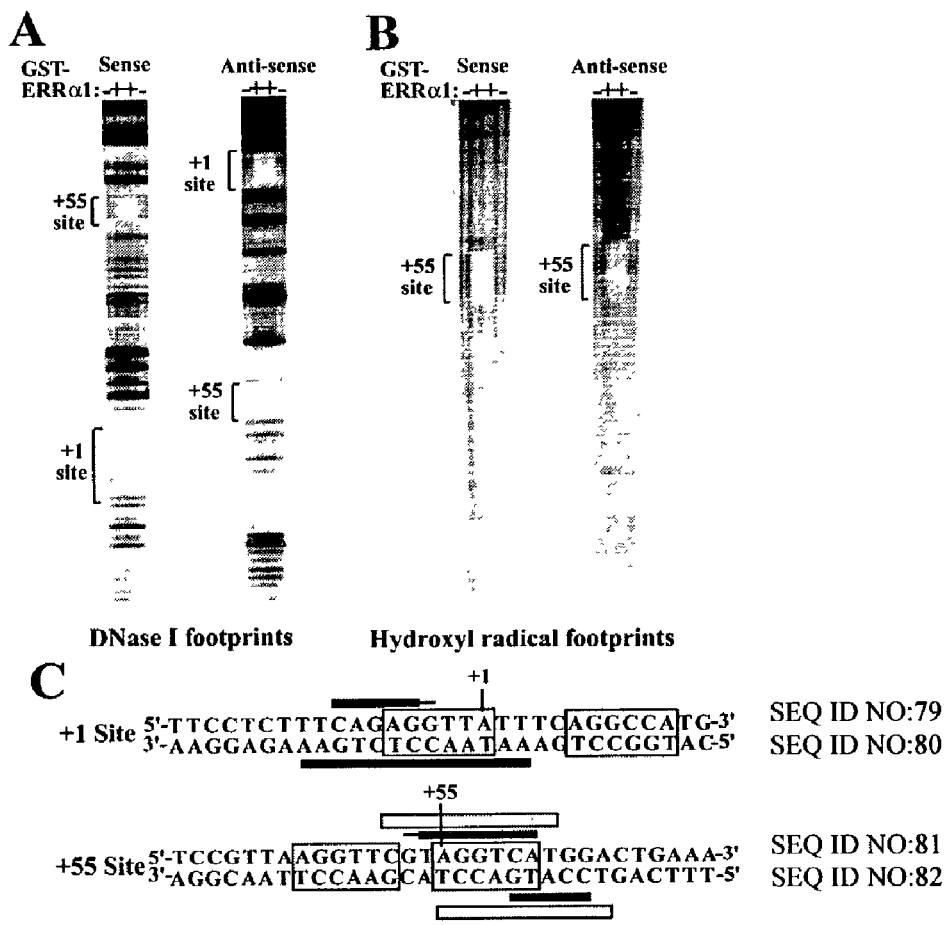
FIGS. 6A and B are radiographic images that demonstrate that ERRα binds to the extended half-site sequences present in the SV40-MLP.
FIG. 6B is a set of autoradiograms of hydroxyl radical footprints of GST-ERRα1 bound to the +55 site of the SV40-MLP in isolation from other ERRα-binding sites.
FIG. 6C summarizes the nucleotides of the SV40-MLP protected by ERRα as determined from the data in panels A and B.

ERRα binds extended hormone response element (HRE) half-sites. Footprinting assays were performed of GST-ERRα1 bound to the major late promoter region of wild-type SV40 DNA. Consistent with the data summarized in FIG. 5, GST-ERRα1 was found to strongly protect from digestion by DNase I the +1 and +55 sites present in the SV40-MLP (FIG. 6A). FIG. 6 demonstrates that ERRα binds the extended HRE half-site sequences present in the SV40-MLP. FIG. 6(A): Autoradiograms of DNase I footprints of GST-ERRα1 bound to the +1 and +55 sites of the SV40-MLP. Outermost lanes, no protein; interior lanes, GST-ERRα1. FIG. 6(B): Autoradiograms of hydroxyl radical footprints of GST-ERRα1 bound to the +55 site of the SV40-MLP in isolation from other ERRα-binding sites. FIG. 6(C): Summary of the nucleotides of the SV40-MLP protected by ERRα as determined from the data in panels A and B. The thick and thin solid bars indicate complete and partial protection, respectively, from digestion with DNase I. The stippled bars indicate nucleotides in the +55 site necessary for binding by ERRα as determined by the hydroxyl radical footprint analysis. The boxed bases are the core half-site sequences present in the +1 and +55 sites (Wiley, S. R., et al., supra, 1993).

Within each of these protected regions are two half-site sequences, either or both of which could potentially be recognized by ERRα. The exact bases protected were determined by comparison with dideoxy sequencing reactions of the probe DNA that were co-electrophoresed next to the footprinting reactions (data not shown) (summarized in FIG. 6C, solid bars). At each site, only one of the two half-sites was covered by ERRα. Therefore, ERRα1 can bind to a single half-site sequence.

Higher resolution mapping of the ERRα binding site was done using a hydroxyl radical footprinting technique with a probe made from an SV40 mutant, pm322C, which is defective in the +1 site (Wiley, S. R., et al., supra, 1993) and, thus, contains only the +55 site. As is shown in FIG. 6B (summarized in FIG. 6C, stippled bars), the nucleotides within and directly adjacent to only one of the two +55 site half site sequences present in the probe DNA were necessary for the binding of GST-ERRα1. Footprint analyses with probe DNAs containing mutations in the unprotected half-site sequences present in the +1 and +55 regions of the SV40-MLP (Wiley, S. R., et al., supra, 1993; data not shown) confirmed that these unprotected half-site sequences do not contribute to the binding of ERRα.. Thus, we conclude that ERRU can bind to extended half-site sequences.

Figure 7:
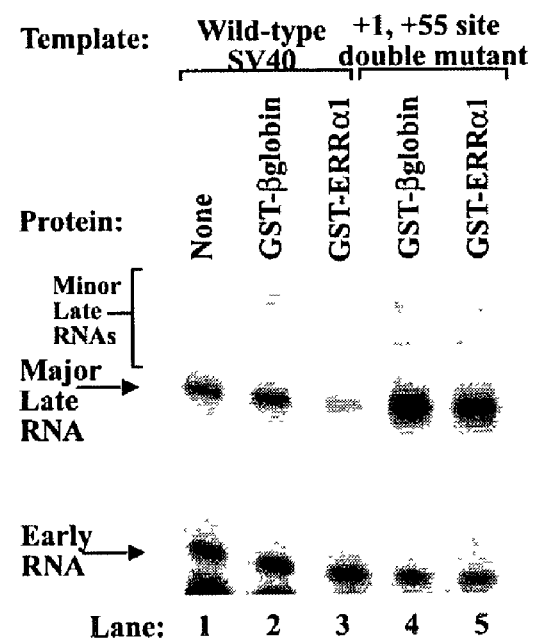
FIG. 7 is a radiographic image of an electrophoretic gel demonstrating that GST-ERRα1 sequence-specifically represses transcription from the SV40-MLP and minor late promoters in a cell-free system.

ERRα sequence-specifically inhibits transcription from the SV40 late promoter: Previous data indicated that a component(s) of IBP-s sequence-specifically repressed transcription from the SV40-MLP in a cell-free system made from HeLa cell nuclear extract (Wiley, S. R., et al., supra, 1993). To confirm that ERRα has this biochemical activity, this assay was repeated with recombinant ERRα1 protein (FIG. 7). FIG. 7 is a photograph of GST-ERRα1 sequence-specifically repressing transcription from the SV40-MLP and minor late promoters in a cell-free system. Approximately 37 ng of purified GST-βglobin (lanes 2 and 4) or GST-ERRα1 (lanes 3 and 5) were incubated with wild-type SV40 DNA or a double mutant defective in binding of ERRα to both the +1 and +55 sites of the SV40 genome (see FIG. 5 for wild-type and mutant sequences and relative binding affinities). A HeLa cell nuclear extract was used to transcribe both the early and late promoters of SV40 present on the same template DNA. Transcripts were detected by primer extension and quantified with a PhosphorImager (Molecular Dynamics).

Addition of GST-ERRα1 reproducibly decreased transcription approximately 3-fold from the wild-type SV40-MLP, but had no effect on transcription from the SV40 early promoter present on the same template DNA (FIG. 7, lane 3 vs. 1 and 2). Transcription from the minor late promoters was also inhibited. When the template contained point mutations in the +1 and +55 ERRα binding sites of SV40, the basal level of transcription from the SV40-MLP and minor late promoters increased as a result of the relief from repression by members of the superfamily present in the HeLa cell nuclear extract. Transcription was also not significantly affected by the addition of GST-ERRα1 (FIG. 7, lanes 4 and 5). These data indicate clearly and definitively that ERRα can, indeed, repress transcription from the SV40-MLP in vitro in a site- and sequence-specific manner. Furthermore, the fact that the SV40 early promoter present in the same reactions was unaffected by ERRα indicates that the repression was not a trivial consequence of squelching—e.g., the binding of a limiting amount of the transcription factor TFIIB.

Figure 8:
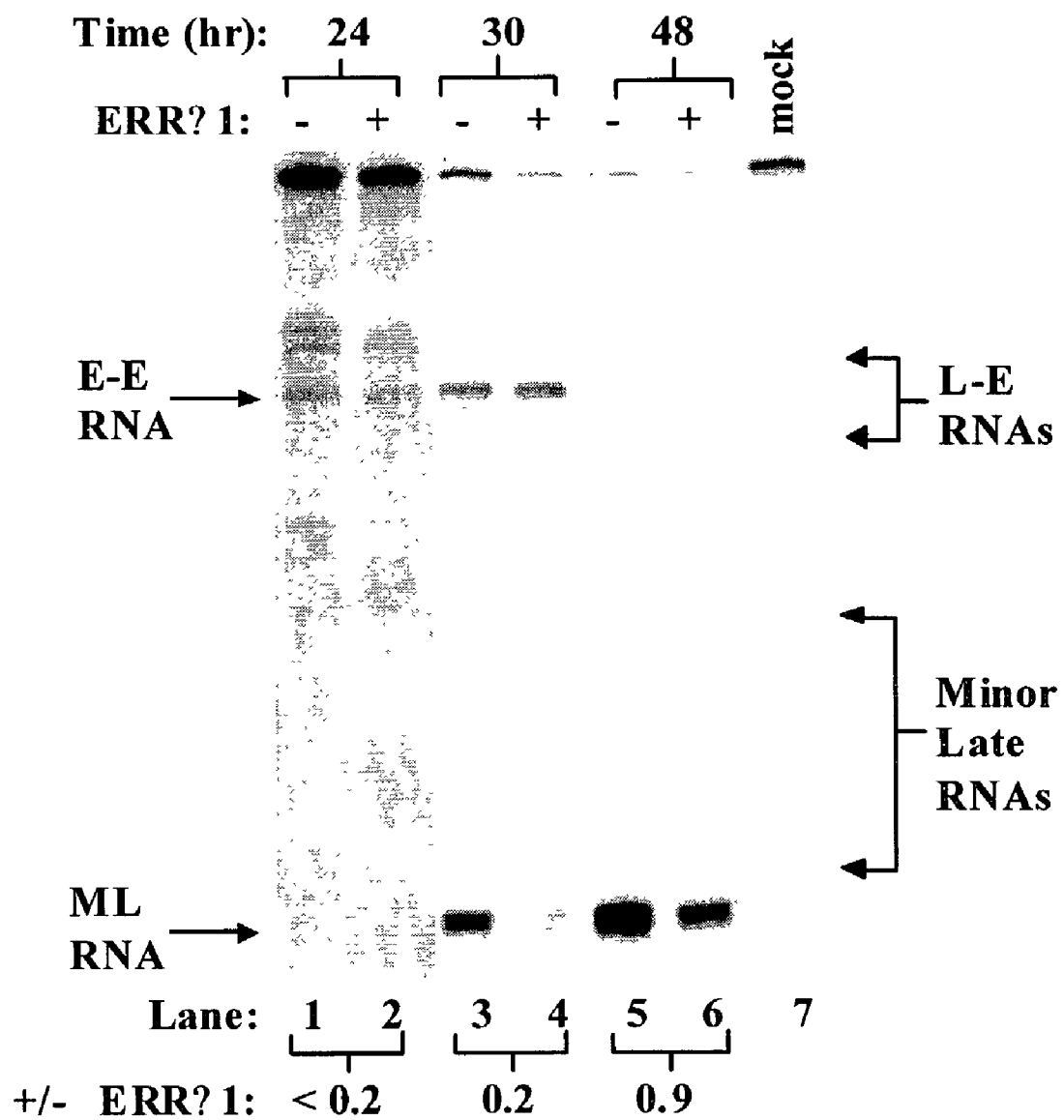
FIG. 8 is a radiographic image of an electrophoretic gel demonstrating that ERRα represses transcription from the SV40 late promoter in vivo.

Zuo and Mertz previously reported that an ERα-ERRα chimeric protein can repress transcription from the SV40-MLP in vivo. They also showed that either COUP-TF1 or TRα1/RXRα can repress transcription from the SV40 late promoter at early times during the lytic cycle of infection of CV-1 cells when viral DNA template copy number is low, but not at late times when viral DNA template copy number is high. To show definitively that this repression activity can also be encoded by ERRα, CV-1P cells were co-transfected with wild-type SV40 and pRSV-ERRα1, a plasmid encoding wild-type ERRα1 and containing and SV40 origin of replication (FIG. 8, lanes 2, 4, and 6). As a control, cells were transfected in parallel with wild-type SV40 and pRSV-0⁺, the empty vector of pRSV-hERRα1 (FIG. 8, lanes 1, 3, and 5).

FIG. 8 is a radiographic image of an electrophoretic gel demonstrating the ERRα represses transcription from the SV40 late promoter in vivo. CV-1P cells were cotransfected with wild-type SV40 DNA (1.2 µg per 10-cm dish) and 0.5 µg pRSV-hERRα1, an expression plasmid encoding ERRα1 (lanes 2, 4, and 6), or pRSV-0⁺, its empty parental plasmid (lanes 1, 3, and 5). The cells were incubated at 37° C. for the indicated times after transfection. Afterward, whole-cell RNA was purified and analyzed by quantitative S1 nuclease mapping with the SV40-specific probe described previously. The relative amounts of SV40 major late (ML) RNA accumulated in the cells were quantified with a PhosphorImager™ and internally normalized to the amounts of SV40 early (E-E) RNA present in the same samples. The numbers at the bottom indicate the ratios of SV40 major late-to-early RNA accumulated by the indicated times post transfection in the presence vs. absence of the ERRα1-expressing plasmid; these data are means from two experiments similar to the one shown here and varied by at most 20%. Lanes 1 and 2, 3 and 4, and 5-7 contained RNA from one-fifth, one-tenth, and one-twentieth of a 10 cm dish of cells, respectively. The arrows indicate the DNAs protected by each of the indicated viral RNA species, with L-E RNAs being SV40-specific RNAs synthesized from the early promoter only at late times after transfection. The exposure time for lanes 1 and 2 was 3-fold longer than for lanes 3-7.

As expected, overexpression of ERRα resulted in a decreased rate of accumulation of the SV40 late, but not early mRNAs until late times after transfection (e.g., 48 hours), a time at which the exogenous as well as endogenous ERRα and other IBP-s have been titrated out as a consequence of viral DNA replication to high template copy number. Therefore, we conclude that ERRα can, indeed, repress transcription from the SV40-MLP both in vitro and in vivo in a sequence-specific manner by binding to extended half-site sequences present in the DNA.

Figure 9:
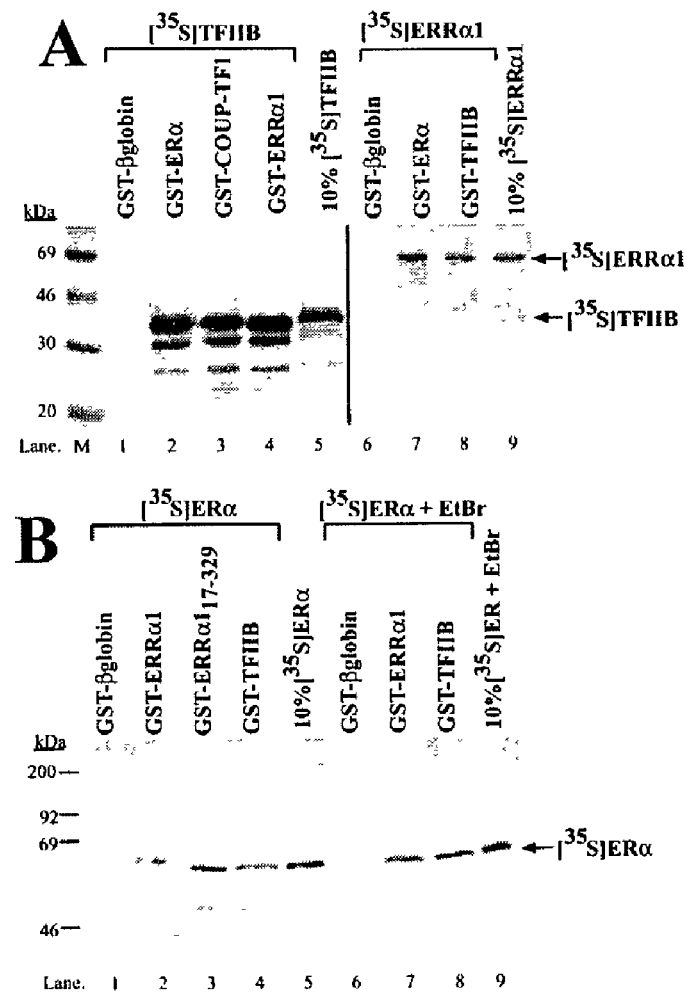
FIGS. 9A and B are radiographic images of electrophoretic gels demonstrating that ERRα associates in vitro with TFIIB and ERα.
FIG. 9B is the reciprocal experiment in which ERα was retained by GST-ERRα1.

ERRα interactions: Many members of the steroid/thyroid hormone receptor superfamily are known to associate functionally with TFIIB (reviewed in ref. Tsai M.-J., and O'Malley, B. W., Annu. Rev. Biochem. 63:451-486, 1994). Therefore, we sought evidence for a similar protein interaction of ERRα with TFIIB. Fusion proteins bound to glutathione-Sepharose were incubated with [$^{35}$S]-labeled proteins synthesized in a rabbit reticulocyte lysate. The affinity resin was washed and specifically retained proteins were eluted by denaturation, resolved by SDS PAGE, and detected by fluorography. In this in vitro system, TFIIB was retained by GST ERRα1 as well as it was retained by GST-COUP-TF1 or GST-ERα (FIG. 9A, lanes 1-4). FIG. 9 is a photograph of an electrophoretic gel demonstrating that ERRα associates in vitro with TFIIB and ERα. The indicated GST-fusion protein was bound to glutathione-Sepharose and incubated with [$^{35}$S]-labeled protein produced by in vitro transcription and translation in a rabbit reticulocyte lysate. After washing, retained proteins were eluted by denaturation and separated by SDS-PAGE. The resulting fluorograms are shown here. In lanes 6-9 of panel B, the crude bacterial lysates and the in vitro translation mixtures were pre-incubated with ethidium bromide (50 μg/ml) to disrupt protein-DNA associations and cleared by centrifugation before being used in the binding assays. Lanes 5 and 9 of panels A and B were loaded with 10% of the indicated proteins added to the binding reactions.

In a reciprocal experiment, labeled ERRα1 was specifically retained by GST-TFIIB (FIG. 9A, lanes 6 vs. 8). To eliminate the possibility that these interactions were mediated by a third protein present in the reticulocyte lysate, this experiment was also performed with proteins synthesized solely in *E. coli* and assayed by immunoblotting: once again, recombinant TFIIB was efficiently retained by GST-ERRα1 (Johnston, S. D., supra, 1996). Thus, we conclude that TFIIB directly associates with ERRα in vitro even in the absence of eukaryotic-specific post-translational modifications.

Yang, et al. (Yang, N., et al., supra, 1996) showed using a far Western assay that GST-ERRα1 appears to interact with a fragment of ERα fused to GST. We performed a series of in vitro protein-protein binding assays as described above. ERRα1 was retained by GST-ERα as well as it was retained by GST-TFIIB (FIG. 9A, lanes 6-8). In a reciprocal experiment, labeled ERα was efficiently retained by GST-ERRα1 (FIG. 9B, lanes 1-4). To insure that these findings were truly a result of protein-protein interactions rather than concurrent binding to DNA fragments present in the protein preparations, this experiment was repeated in the presence of ethidium bromide, a chemical which disrupts protein-DNA interactions because it distorts the structure of the DNA: the presence of ethidium bromide did not significantly affect the retention of ERα by GST-ERRα1 (FIG. 9B, lanes 6-8 vs. 1-4). To confirm that the ERRα/ERα protein-protein interaction was direct rather than via a third protein present in the lysates, the GST-fusion protein binding experiment was also performed with purified, recombinant ERα: ERα still bound to ERRα1 as efficiently as it did to TFIIB (Johnston, S. D., supra, 1996). Therefore, we conclude that ERRα and ERα can directly interact in vitro.

Preliminary experiments were performed to map the regions of ERRα that interact with ERα. Deletion mutants of ERRα1 were tested for their ability to bind ERα (FIG. 10). The [$^{35}$S] methionine-labeled ERα protein was synthesized in a rabbit reticulocyte lysate. The GST fusion proteins, containing the amino acids of ERRα1 indicated, were synthesized in *E. coli* and purified using glutathione-Sepharose. Binding assays were performed as described in FIG. 9. B, ERα was found to bind most well the full-length protein (ERRα1 amino acids 1-423), and small deletions from the C-terminus of ERRα (ERRα1 amino acids 1-376) significantly reduced binding of ERα. However, moderate amounts of ERα still bound to ERRα's DBD (amino acids 1-173); FIG. 10B). Thus, ERα-ERRα protein-protein interactions mediated through the C-terminus of ERRα may allow these receptors to cross-modulate each other's activites, and/or allow these receptors to interact while bound to different response elements from the same promoter.

Relative binding of ERRα, ERα and COUP-TF1 to several EREs: We have shown that ERRα binds to known estrogen-response elements (see FIG. 5). In an attempt to compare the relative binding affinities of ERRα to that of ERα on any given ERE, we performed gel-mobility-shift assays as follows. The indicated radiolabeled double-stranded DNAs (EREs) were incubated with whole-cell extracts prepared from COS cells transfected with plasmids encoding the indicated receptor. The sequences of the vitellogenin (Vit) (lanes 2-4, FIG. 11) and prolactin D (Prol D) (lanes, 11-13, FIG. 11) probes are shown in FIG. 5. The sequences of the synthetic direct repeat element (DRE) (lanes 4-6, FIG. 11) and the pS2 (lanes 8-10, FIG. 11) probes were 5'-CCTGCAAGGT-CACGGAGGTCACCCCG-3' (SEQ ID NO:3) and 5'-CCT-GCAAGGTCACGGTGGCCACCCG-3' (SEQ ID NO:4), respectively.

Figure 11:
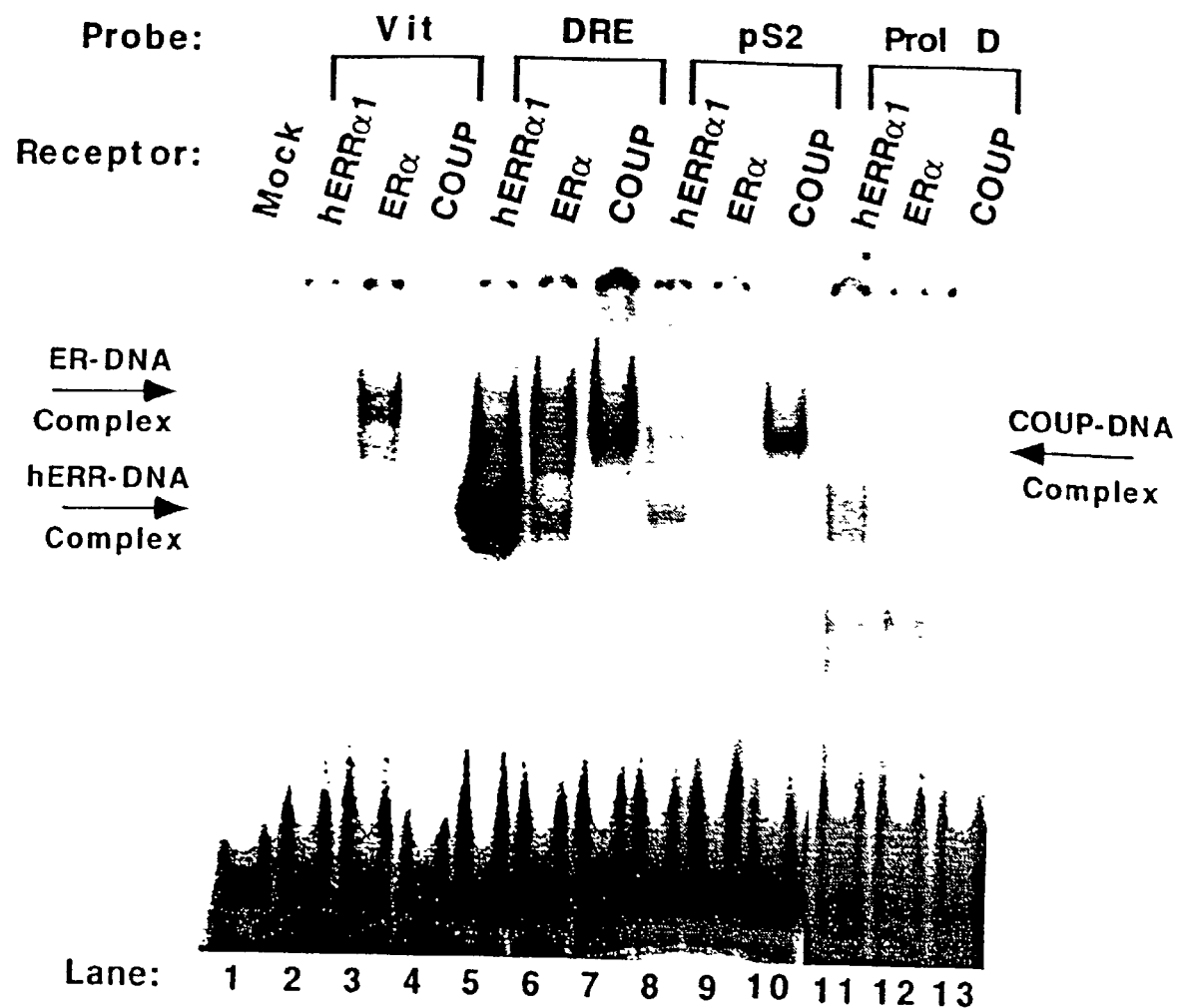
FIG. 11 is a radiographic image of an electrophoretic gel demonstrating that ERRα binds to some naturally occurring estrogen-responsive elements with higher affinity than does ERα, including the ERE of the pS2 gene, overexpression of which correlates with malignant breast cancer.

Not surprisingly, the different EREs were found to bind each of the receptors with different relative affinities. For example, ERRα bound the ERE of the promoter of the pS2 gene with a higher affinity than did ERα (FIG. 11, lane 8 versus 9). On the other hand, ERα bound to the vitellogenin ERE more efficiently than did ERRα, while COUP-TF1 failed to recognized this palindromic ERE at all (FIG. 11, lanes 2-4). The pS2 gene was cloned from a human breast cancer cell line, is subject to transcriptional activation upon the addition of estradiol to culture, and is frequently overexpressed in breast cancers (Berry, M., et al., *PNAS* 86:1218-1222, 1989. Thus, alterations in the amount or activity of ERRα in a cell may relate to some estrogen-involved malignancies. Given that ERRα2 is identical to ERRα1 in the DNA binding domain (FIG. 1B), it probably has a similar sequence specificity and, thus, may also relate to some estrogen-involved malignancies when altered.

Mutually exclusive binding of ERα and ERRα: To determine whether ERRα can compete with ERα for binding to some EREs, we performed gel-mobility-shift assays using the radiolabeled vitellogenin ERE double-stranded DNA as a probe and whole-cell extracts of COS cells transfected with the receptor proteins. Upon addition of increasing amounts of ERRα1, an increase in the amount of ERRα1-DNA complex was observed along with an approximately five-fold decrease in the amount of the ERα-DNA complex. In addition, no heterodimer-DNA complex was observed. Thus, ERRα can compete with ERα for binding to the vitellogenin ERE in a mutually exclusive manner.

In summary, we conclude that ERRα can probably affect the expression of some estrogen-responsive genes by competing with ERα for binding to EREs present in the promoters of these genes. Given this finding, we expect that changes in the amounts or activities of ERRα within a cell would likely lead to alterations in the expression of many estrogen-responsive genes and, thus, lead to changes in cells that could play roles in malignancies.

Discussion

We identified here the protein, ERRα1, that corresponds to the major mRNA (FIG. 3) and protein (FIG. 2) products synthesized in vivo from the ERRα gene. Using recombinant protein, we identified DNA binding sites in a variety of promoters (FIGS. 5 and 11) and found that the highest affinity sites contain the extended half-site sequence 5'-TCAAG-GTCA-3'. Footprinting analysis confirmed that ERRα can bind this DNA sequence (FIG. 6). In addition, we showed that ERRα is capable of modulating transcription through its binding sites both in vitro (FIG. 7) and in vivo (FIG. 8). These are the first functional assays of ERRα. They may prove useful as the basis for a screen for ligands to ERRα. We also showed that ERRα1 interacts in vitro with ERα and TFIIB (FIG. 9); the interaction with ERα occurs via ERRα's C-terminus (FIG. 10). Furthermore, ERRα binds with higher affinity than ERα to the ERE of the pS2 gene, a gene frequently overexpressed in breast cancer (FIG. 11) and competes with ERα for binding to some EREs. Thus, we predict that ERRα may modify the estrogen-responsiveness of some genes, including ones involved in some cancers. Furthermore, since ERRα2 conains the entire ERRα1 sequence plus additional N-terminal residues (FIG. 1B), we predict that ERRα2 may also modify the estrogen responsiveness of some genes, including ones involved in some cancers.

The ERRα1 protein: We and others (Yang, N., et al., supra, 1996) have failed to find evidence for a protein encoded by the ERRα cDNA described by Giguère, et al. (Giguère, V., et al., supra, 1988). We detected, instead, an mRNA (FIG. 3) with a 5'-end located 3' of the site needed to encode ERRα. This mRNA has the potential to code for a smaller ERRα protein which we named ERRα1. Its existence in vivo was confirmed by immunoblotting and immunoprecipitation experiments (FIG. 2). The structure of the mRNA identified here is in agreement with the genomic structure of the ERRα gene (Shi, et al., *Genomics* 44(1):52-60, 1997, incorporated by reference as if fully set forth herein). ERRα1 is a protein of approximately 53 kDa; however, other isoforms of ERRα may exist as well (e.g., ERRα2). ERRα1 is probably the same protein as the larger of two ERRα isoforms recently described by Yang, et al. (Yang, N., supra, 1996). We failed to detect the smaller, 42-kDa protein that Yang, et al. (Yang, N., supra, 1996) found by immunoblotting. This discrepancy is likely due to the use of different ERRα-specific antisera.

The ERRα binding site: A high-affinity ERRα binding site was determined to be the extended half-site sequence, 5'-TCAAGGTCA-3' (FIG. 5). This finding is in agreement with the prediction of Wilson, et al. (Wilson, T. E, et al., supra, 1993) made on the basis of the sequence similarity of the proximal A box of ERRα to SF-1. We also confirmed that the FP1 sequence of the human lactoferrin promoter is a strong ERRα binding site (FIG. 5; Yang, N., supra, 1996). Significant sequence variability in the 5' extension of the consensus half-site sequence is tolerated by ERRα. Most notably, the SV40 +55 UP mutant and the prolactin D sites each have a single base difference from the consensus 5'-extension, but were found to bind ERRα very well (FIG. 5). Indeed, many sequences that do not contain the 5'-TCA-3' extension were bound by ERRα at moderate levels. For example, the vitellogenin ERE, which contains two consensus half-sites (5'-AGGTCA-3') without an upstream 5'-TCA-3', was bound at reasonable levels by ERRα (FIG. 5).

Sequences outside of the 9-bp extended half-site also appear to play a role in determining a site's strength. For example, the SF-1, CYP1A2-1 and P450 scc oligonucleotides each contain a perfect consensus extended half-site, but their relative affinities varied more than 60-fold (FIG. 5). This finding is in agreement with the observation that ERRα contacts at least one base outside of the extended half-site (Yang, N., supra, 1996). On the other hand, the integrity of the core half-site sequence is clearly necessary, as mutations in the core of the vitellogenin ERE and SV40 +1 and +55 sites led to a complete loss of binding (FIG. 5).

ERRα was initially cloned on the basis of its sequence, rather than its function. Therefore, genes regulated by ERRα are largely unknown. The data from the quantitative, competition gel-mobility-shift assays (summarized in FIG. 5 and Table 3) indicated several promoters that may be regulated by ERRα. Also, binding sites other than the strongest binding sites may be true physiological targets. For example, the SV40-MLP contains two moderate-strength binding sites (FIG. 5), yet was repressed by ERRα in vitro (FIG. 7) and in vivo (FIG. 8) up to 10-fold. The physiologic importance of these ERRα binding sites awaits additional experiments.

Many sequences are recognized by multiple members of the steroid/thyroid hormone receptor superfamily: Many of the DNA sequences that have been shown here to be bound by ERRα are already known to bind other members of the steroid/thyroid hormone receptor superfamily. The highest affinity binding site we found is identical to an oligonucleotide that is strongly bound by SF-1 (Wilson, T. E, et al., supra, 1993). Additionally, the vitellogenin ERE (Klein-Hitpaβ, L., et al., supra, 1986), the prolactin D sequence (Murdoch, F. E., et al., supra, 1995; Somasekhar, M. B., and Gorski, J., *Gene* 69:13-21, 1988), and the creatine kinase B sequence (Wu-Peng, X. S., et al., supra, 1992) are all known to be bound by ERα and mediate transcriptional induction by estrogens. The SV40 +1 and +55 sites are functionally bound by COUP-TF1, COUP-TF2, and TRα1/RXRα (Zuo, F., and Mertz, J. E., supra, 1995; Zuo, F., Ph.D. Thesis. Regulation of the SV40 late promoter by members of the steroid/thyroid hormone receptor superfamily. University of Wisconsin-Madison, 1995) as well as by ERRα (FIGS. 7 and 8). In this latter case, any of these superfamily members can repress transcription from the SV40-MLP. Thus, ERRα can bind to sequences that are also recognized by other members of the superfamily. The meaning of overlapping binding specificity remains unclear.

COUP-TFs have been shown to repress transactivation by many members of the steroid/thyroid hormone receptor superfamily (Qiu, Y., et al., *Endocrinol. Metab.* 5:234-239, 1994). COUP-TFs can repress by multiple mechanisms, including competition for DNA binding sites (Cooney, A. J., et al., *J. Biol. Chem.* 268:4152-4160, 1993; Liu, Y., et al., *Mol. Cell. Biol.* 13:1836-1846, 1993). Because ERRα binds to several functional EREs (FIG. 5, Table 3 in Example 4), it may function in a similar manner to COUP-TFs by acting as a general repressor of estrogen-regulated genes in the absence of liganded ERs. In the presence of estrogen or an increase in the molar ratio of ER to ERRα, activated ER may displace ERRα, allowing for both true activation and anti-repression of the target genes. Data presented in Example 2 further explore the mechanisms of ERRα-mediated down-modulation and illustrate that this factor also contains a repressor domain. ERRα has also been demonstrated to contain a transactivation domain (Lydon, J. P., et al., supra, 1992). Thus, it is likely that ERRα can transcriptionally activate targets in some contexts. In the case of the lactoferrin promoter, the ERRα binding site is necessary for maximal transactivation by ERα acting through a weak, downstream ERE (Yang, N., et al., supra, 1996). Because most members of the steroid/thyroid hormone receptor superfamily are not ubiquitously expressed, the ability of some sites to be bound by several members of the superfamily may effectively increase the number of tissues in which an element is recognized. Finally, there may be additional requirements for receptor binding to these promoter sites that are not fully reproduced in these in vitro systems.

In summary, we have shown here that a major isoform of the ERRα gene is ERRα1. We have characterized high-affinity binding sites for ERRα, shown that ERRα can bind some EREs with higher affinity than does ERα and compete with ERα for binding to some EREs, and developed the first functional assays for ERRα activity. Furthermore, because this receptor binds both ERα and EREs, we propose that ERRα1

EXAMPLE 2

Estrogen-related Receptor α Actively Antagonizes Estrogen Receptor-regulated Transcription in MCF-7 Mammary Cells Abstract The estrogen-related receptor α (ERRα) is an orphan member of the nuclear receptor superfamily. We show that the major isoform of the human ERRα gene, ERRα1, can sequence-specifically bind a consensus palindromic estrogen response element (ERE) and directly compete with estrogen receptor α (ERα) for binding. ERRα activates or represses ERE-regulated transcription in a cell type-dependent manner, repressing in ER-positive MCF-7 cells while activating in ER-negative HeLa cells. Thus, ERRα can function both as a modulator of estrogen responsiveness and as an estrogen-independent activator. Repression likely occurs in the absence of exogenous ligand since charcoal treatment of the serum had no effect on silencing activity. Mutational analysis revealed that repression is not simply the result of competition between ER and ERRα for binding to the DNA. Rather, it also requires the presence of sequences within the carboxyl-terminal E/F domain of ERRα. Thus, ERRα can function as either an active repressor or a constitutive activator of ERE-dependent transcription. We hypothesize that ERRα can play a critical role in the etiology of some breast cancers, thereby providing a novel therapeutic target in their treatment.

Introduction

Figure 12:
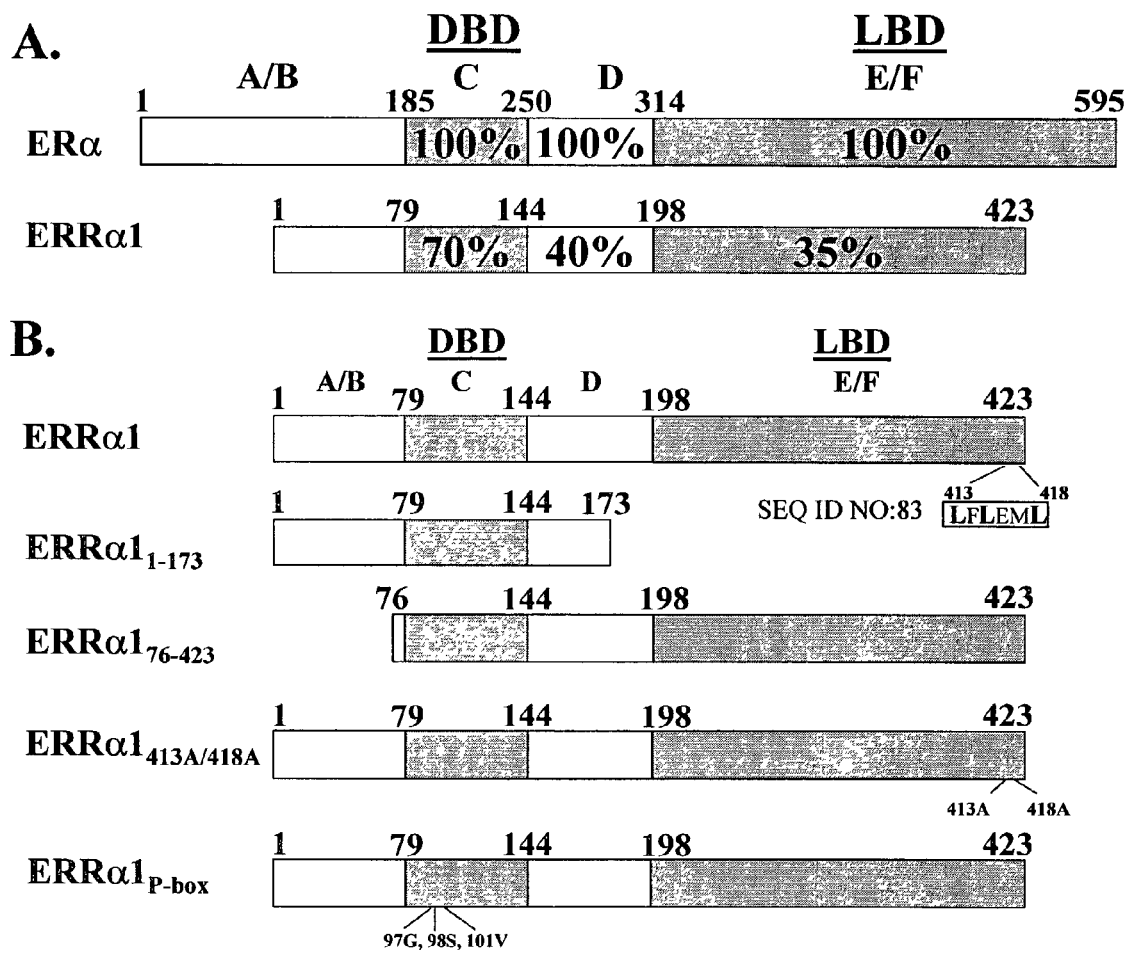
FIG. 12 is a schematic representation of ER and ERR family members. A, comparison of the sequence similarity between human ERα and human ERRα1. The letters A-F indicate the domains typically found in NRs. DBD and LBD denote the DNA binding and ligand binding domains, respectively. The numbers refer to the amino acid residues. The percentages indicate the amino acid sequence similarity between the corresponding domains of the two proteins, with ERα sequences set at 100%. B, structures of the variants of ERRα1 studied here. Amino acid substitution mutations are indicated at the sites of the numbered residues.
Figure 13:
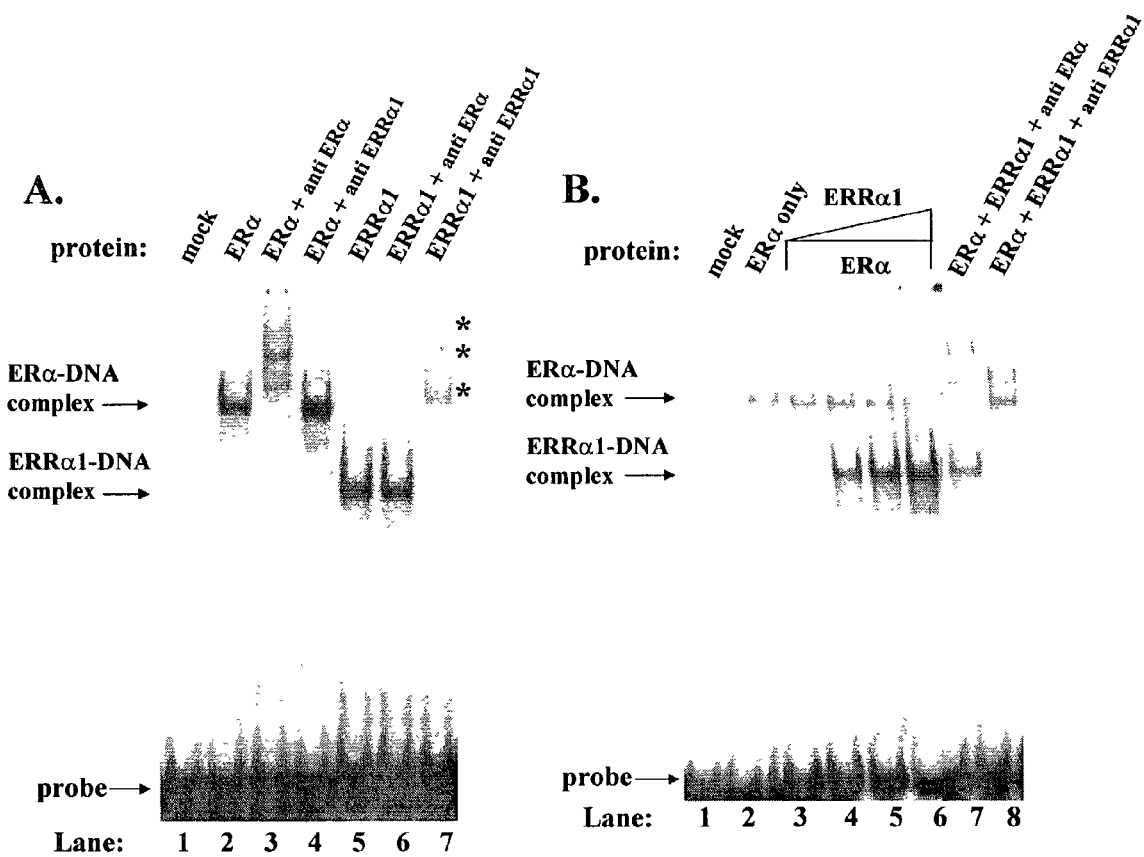
FIG. 13 shows binding of ERRα to a consensus ERE and its ability to exclude ERα from binding DNA. A, both ERRα1 and ERα bind efficiently to an ERE. Approximately 5 µg of whole-cell extract obtained from COS-M6 cells overexpressing ERRα1 or ERα was incubated with the radiolabeled, double-stranded oligonucleotide corresponding to the sequence 5'-TAAGCTT<u>AGGTCA</u>CAG<u>TGACCT</u>AAGCTTA-3' (ERE core half-site sequences are underlined). The protein-DNA complexes were separated by electrophoresis in a native 5% polyacrylamide gel. Lane 1, probe alone; lane 2, ERα-containing extract; lane 5, ERRα1-containing extract; lanes 3, ERα-containing extract plus the ERα-specific antibody H222; lane 4, ERα-containing extract plus an ERRα1-specific polyclonal antiserum (11); lane 6, ERRα1-containing extract plus ERα-specific antibody H222; lane 7, ERRα1-containing extract plus ERRα1-specific polyclonal antiserum. The arrows indicate the specific DNA-protein complexes and free probe DNA. The asterisk denotes antibody-supershifted complexes. B, ERα and ERRα1 compete for binding to the ERE. The radiolabeled ERE probe was incubated with a constant amount of whole-cell extract containing ERα by itself (lane 2) or with increasing amounts of whole-cell extract containing ERRα1 (lanes 3-6). Lanes 7 and 8 contained 2.5 µg of ERα-containing extract plus 2.5 µg of ERRα1-containing extract preincubated with ERα-specific antibody or hERRα1-specific polyclonal antiserum, respectively.

The nuclear receptor (NR) superfamily is comprised of hundreds of transcription factors that regulate a vast array of genes and physiological responses (1-9). Most nuclear receptors share a similar structural organization (FIG. 12A). The amino-terminal A/B domain can function as a hormone-independent activator of transcription. The highly conserved C domain contains the DNA binding domain (DBD) that confers sequence-specific DNA binding activity. A hinge region, called the D domain, bridges the C domain with the carboxyl-terminal E/F domain that includes the receptor-specific ligand binding domain (LBD) of the protein. The binding of appropriate ligands results in conformation changes leading to alterations in the transcriptional properties of the receptor, including the exposure of a transcriptional activation region within the carboxyl end. Although many nuclear receptor superfamily members bind known ligands (e.g., steroids, retinoids, thyroid hormones), some, termed orphan receptors, share significant sequence similarity in their LBDs with their ligand binding family members but lack as-yet known naturally occurring ligands (7-10)

Among the first orphan receptors identified were the estrogen-related receptors ERRα and ERRβ (officially named NR3B1 and NR3B2, respectively) (10). They were cloned by low stringency screening of cDNA libraries with probes corresponding to the DBD of estrogen receptor α (ERα) (10). Subsequently, ERRα1 was identified as the major isoform present in HeLa cells (FIG. 12A) (11, 12). The DBD of human ERRα shares 70% amino acid similarity with the DBD of human ERα; the LBD shares 35% amino acid identity. A third member of the ERR family, ERRγ (NR3B3), has also been identified (13-15). These three ERRs are closely related by sequence similarity but encoded by different genes.

Despite sequence similarity with ERs in the LBD, the ERRs do not bind 17β-estradiol (11, 15, 16), and the identification of naturally occurring ligands for ERR family members has remained elusive. Vanacker et al. (17) reported that a serum component removable by treatment with charcoal regulates ERRα-dependent transcription. However, remaining unclear is whether this factor(s) acts directly by binding to ERRα or indirectly through a signal transduction pathway. Yang and Chen (18) found that the pesticides toxaphene and chlordane decrease the activity of ERRα, whereas others reported that ERRs can constitutively interact with co-activators independent of any ligand (19-23). Interestingly, the synthetic estrogen diethylstilbestrol has been shown to antagonize the activation function of ERR family members by disrupting ERRα interactions with coactivators (22, 23); 4-hydroxytamoxifen acts likewise, but only with ERRγ, not ERRα (24). Thus, ligands appear to affect the activities of ERRs, but via non-classical mechanisms.

The ERRs also differ somewhat from the ERs in their binding site specificities. They recognize estrogen response elements (EREs) (11, 25-29); however, ERRα binds with even higher affinity to the consensus steroidogenic factor-1 response element-extended half-site sequence 5'-TCAAGGTCA-3' (11, 27, 26). Interestingly, the sequence 5'-TAAAGGTCA-3' is also recognized by ERRα but not by steroidogenic factor-1 (17). Therefore, some genes likely contain estrogen-related receptor response elements regulated only by ERR family members. Thus, ERR family members likely signal via cross-talk with other nuclear receptors through common binding sites as well as ERR-specific genes via ERR-binding sites.

The ERR family members have been shown to function in numerous cell types as transcriptional activators of promoters containing EREs, steroidogenic factor-1 response elements, and ER response elements (16-31). Nevertheless, we found that ERRα repressed rather than activated transcription in ER-negative CV-1 cells when it binds sites within the late promoter of SV40 (11, 32). Thus, ERRs likely modulate gene expression via several mechanisms.

To better understand the multiple activities of ERRα, we investigated here the effects of ERRα on expression from an ERE-regulated promoter in ER-positive versus ER-negative cells. We show that ERRα can function as either a repressor or activator of ERE-mediated transcription in a cell type-dependent manner. The mechanism of repression involves interactions with cellular corepressor(s) as well as binding to the ERE. We propose ERRα likely plays roles in the etiology of some breast cancers and the progression from an ER-dependent to ER-independent state.

Materials and Methods

Plasmids: All plasmid DNAs were constructed by standard recombinant DNA techniques. Plasmid p3xERE-TK-luc, a gift from V. C. Jordan, contains three tandem copies of the palindromic ERE sequence 5'-TAAGCTT<u>AGGTCACAGTGACCT</u>AAGCTTA-3' (SEQ ID NO:9), placed upstream of a minimal herpes simplex thymidine kinase (TK) promoter (nucleotides −109 to +52 relative to the transcriptional start site of the TK promoter), directing expression of the luciferase coding sequence (33). The ERE-negative control plasmid, pTK-luc, was generated from p3xERE-TK-luc by cleavage at the two HindIII sites directly surrounding the three EREs and ligation.

Plasmid pcDNA3.1-hERRα1 encodes wild-type human ERRα1 expressed from the cytomegalovirus promoter. It was constructed by reverse transcription-PCR amplification of ERRα mRNA isolated from normal human mammary gland RNA (CLONTECH, Palo Alto, Calif.) followed by PCR-based cloning of the coding region into pcDNA3.1/V5-His (Invitrogen). To ensure efficient initiation and termination of translation of the ERRα open reading frame, the cloning was performed using the primers 5'-gacttcGCCACC ATGAGCAGCCAGGTGGTGGTGCATTGA-3' (SEQ ID NO:10) (lowercase letters indicate an EcoRI site, underlined letters indicate the translation initiation codon, and bold letters indicate bases altered to optimize translation initiation while maintaining coding of the wild-type ERRα1 protein) and 5'-ggatccTCAGTCCATCATGGCCTCGAGCAt-3' (SEQ ID NO:11) (lowercase letters indicate a BamHI site, and underlined letters indicate the translation termination codon). DNA sequence analysis confirmed that the protein encoded by this plasmid corresponds to the wild-type ERRα1 referenced in GenBank entry NM-004451.

Plasmids pcDNA3.1-hERRα1$_{1-173}$, pcDNA3.1-hERRα1$_{76-423}$, pcDNA3.1-hERRα1$_{L413A/L418A}$, and pcDNA3.1-hERRα1$_{P-box}$ encode mutant variants of ERRα1 (FIG. 12B). They were constructed by PCR-based methods with pcDNA3.1-hERRα1 as the starting template. For pcDNA3.1-hERRα1$_{1-173}$ and pcDNA3.1-hERRα1$_{L413A/L418A}$, the primers used for the termination codon-containing plasmids were, respectively, 5'-ggatcc TCACGGGAAGGGCAGTGGGTCCA-3' (SEQ ID NO:12) and 5'-ggatccTCAGTCCATCATGGCCTCGGCCATCTC CAAGAACGCCTTGTGCATGGGCACCTTGC-3' (SEQ ID NO:13) (bold letters indicate bases altered to change leucine codons to alanine). Likewise, pcDNA3.1-hERRα1$_{76-423}$ was constructed using 5'-gaattcGCCACCATGAAGCGC CTCTGCCTGGTCT-3' (SEQ ID NO:14) for the initiation codon-containing primer.

Plasmid pcDNA3.1-hERRα1$_{P-box}$ contains three amino acid substitution mutations (E97G/A98S/A101V) within the predicted P-box of the ERRα1 DNA binding domain that abrogate the ability of the protein to bind DNA. It was constructed by PCR amplification of the open reading frame of ERRα1 in two directly abutting fragments corresponding to the amino and carboxyl termini of the protein. The ERRα1$_{P-box}$ amino-terminal fragment was amplified using as primers the wild-type translation initiation codon-containing primer and 5'-phosphate-GGACCCACAGGATGCCACAC-CATAGTGGTA-3' (SEQ ID NO:15). The ERRα1$_{P-box}$ carboxyl-terminal fragment was amplified using as primers the wild-type translation termination codon-containing primer and 5'-phosphate-TGCAAAGTCTTCTTCAAGAGGAC-CATCCA-3' (SEQ ID NO:16). The resulting PCR products were digested with EcoRI and BamHI, respectively, ligated together, and re-amplified using the wild-type initiation and termination codon-containing primers to produce the full-length ERRα1$_{P-box}$ mutant.

Cells: The ER-positive, human mammary carcinoma MCF-7 cell line was cultured in RPMI 1640 medium supplemented with 10% fetal bovine serum (FBS), 6 ng of insulin/ml, 3 μg of glutamine/ml, and 100 units of penicillin and streptomycin/ml. The ER-negative, human cervical HeLa cell line and the monkey kidney COS-M6 cell line were cultured in Dulbecco's modified Eagle's medium supplemented with 10% FBS and 100 units of penicillin and streptomycin/ml. When cells were cultured in estrogen-free medium, referred to here as stripped medium, dextran-coated charcoal-treated FBS (34) replaced whole FBS and phenol red-free RPMI 1640 replaced RPMI 1640.

Transient Transfections and Luciferase Assays: To assess the role ERRα plays in regulating transcription of an ERE-containing promoter, MCF-7 or HeLa cells grown in 12-well tissue culture plates were co-transfected in parallel with 0.5 μg of pTK-luc versus p3xERE-TK-luc along with the indicated amounts of the empty cloning vector pcDNA3.1, the ERRα1 expression plasmid pcDNA3.1-hERRα1, or mutant variants thereof. Transfections were performed with the aid of the TransIT LT1 transfection reagent (PanVera, Madison, Wis.) as previously described (35). To examine the effects of ER ligands, cells were maintained in stripped medium for 48 h before transfection and the addition of 17β-estradiol (E$_2$) (Sigma) or the pure anti-estrogen ICI-182,780 (Astra Zeneca, London, UK) dissolved in ethanol and diluted in medium to obtain the indicated concentrations. Cells were harvested 48 h post-transfection, and lysates were assayed for luciferase activity normalized to protein concentration as previously described (36).

Ectrophoretic Mobility Shift Assays (EMSAs): EMSAs were performed essentially as described by Reese et al. (37) using whole-cell extracts prepared as described previously (35). Briefly, whole-cell extracts obtained from five 10-mm dishes of COS-M6 cells that had been transfected 48 h previously with 3 μg/dish of the desired expression plasmid served as the source of NRs. Transfections were performed with the aid of the TransIT LT1 transfection reagent as previously described (35). The radiolabeled double-stranded synthetic oligonucleotide 5'-TAAGCTTAGGTCACAGT-GACCTAAGCTTA-3' (SEQ ID NO:9) served as the ERE probe. One to five μl of extract (10-100 μg of protein) was preincubated on ice for 20 min in a 16-μl reaction mixture containing 20 mM HEPES (pH 7.4), 1 mM dithiothreitol, 100 mM NaCl, 10% glycerol (v/v), 3 μg of BSA, and 4 μg of poly(dI-dC). Radiolabeled probe (about 1.0 ng) was added, and the mixture was incubated for 15 min at room temperature. The samples were loaded directly onto a 5% non-denaturing polyacrylamide gel with 0.5×Tris-buffered EDTA as running buffer and electrophoresed at 200 V for 2 h at 4° C. Immunoshift assays were performed by the addition of the indicated antiserum at the preincubation step. The ERα-specific antiserum was the monoclonal antibody H222 (kindly provided by Dr. Geoffrey Greene). The ERRα-specific antiserum was the previously described polyclonal one raised in rabbits against glutathione S-transferase GST-ERRα1$_{17-329}$ (11).

Western Blots: To determine whether the NRs were efficiently and correctly expressed, 5-10 μg of whole-cell extract containing the overexpressed NR were resolved by SDS, 12% PAGE. The proteins in the gel were electroblotted onto a nitrocellulose membrane. The membranes were probed with a rabbit polyclonal antiserum raised against GST-ERRα1 (11) followed by anti-rabbit IgG peroxidase (1:1000 dilution). The retained antibodies were detected by enhanced chemiluminescence.

Results

Figure 15:
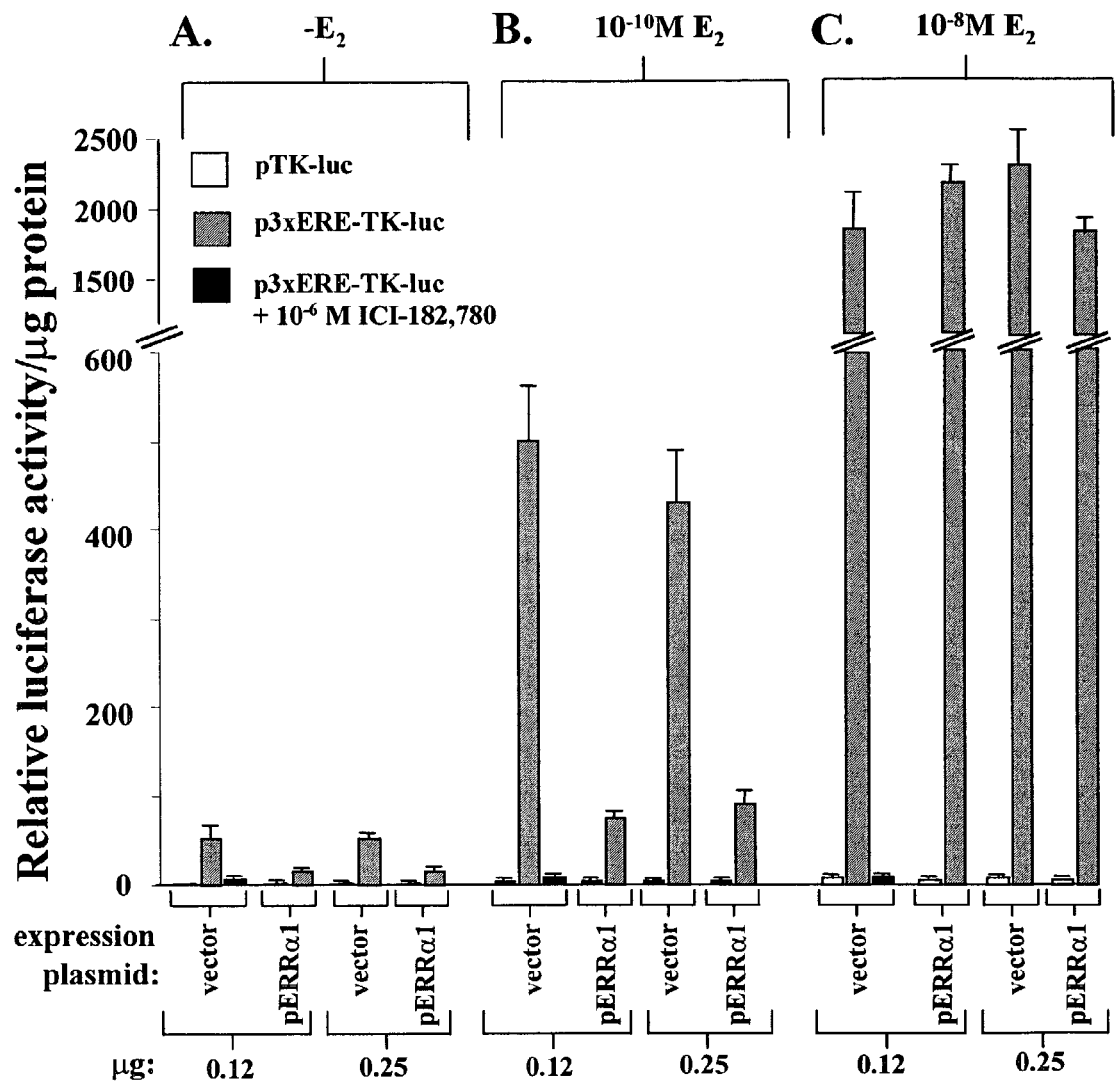
FIG. 15 shows that ERRα down-modulates estrogen responsiveness. MCF-7 cells were co-transfected in parallel with 0.5 μg of pTK-luc or p3xERE-TK-luc and 0.12 or 0.25 μg of pcDNA3.1-hERRα1 or its empty parental vector pcDNA3.1. The cells were subsequently incubated for 48 h in medium supplemented with charcoal-stripped FBS only (A) plus $1\times10^{-10}$ M 17β-estradiol (B) or plus $1\times10^{-8}$ M 17β-estradiol (C) before being harvested and assayed for luciferase activity. The data are presented relative to the activity observed in the cells co-transfected with pTK-luc and 0.12 μg of vector pcDNA3.1 and maintained in medium supplemented with charcoal-stripped FBS only. They are the means plus S.E. of data obtained from three separate experiments. The black bars represent data from cells incubated in the presence of $1\times10^{-6}$ M of the anti-estrogen ICI-182,780.

Competition between ERRα and ERα for Binding an ERE: Johnston et al. (11) and others (12) showed previously that ERRα can bind to some naturally occurring EREs. To test whether ERRα recognizes the palindromic ERE sequence, 5'-TAAGCTTAGGTCACAGTGACCTAAGCTTA-3' (SEQ ID NO:9), EMSAs were performed using whole-cell extracts obtained from COS-M6 cells that contained overexpressed ERα or ERRα1 as protein source and a radiolabeled, double-stranded synthetic oligonucleotide that contained the palindromic ERE sequence as probe. As shown in FIG. 15, both ERα and ERRα bound to this synthetic ERE. ERα generated a protein-DNA complex that was immunoshifted with the ERα-specific antibody H222 but not with the ERRα-specific antiserum. ERRα also bound the ERE, generating a single protein-DNA complex that migrated faster than the ERα-DNA complex and was immunoshifted with the ERRα-specific antibody but not with the ERα-specific antiserum. Thus, both ERα and ERRα can bind this palindromic sequence.

To determine whether the binding of ERRα and ERα to this ERE is mutually exclusive, cooperative, or competitive, EMSAs were performed with a constant amount of ERα plus various amounts of ERRα1 mixed together in the same binding reaction. As shown in FIG. 15, the addition of increasing amounts of ERRα1 yielded an increase in the amount of ERRα1-DNA complex along with a corresponding decrease in the amount of ERα-DNA complex. Similar results were obtained when this competition experiment was performed with extracts of COS-M6 cells that had been co-transfected with various molar ratios of the ERα- and ERRα-expressing plasmids. Thus, the binding of ERRα and ERα to this palindromic ERE is mutually exclusive, with ERRα effectively competing with ERα for binding when present in sufficient amounts.

Figure 14:
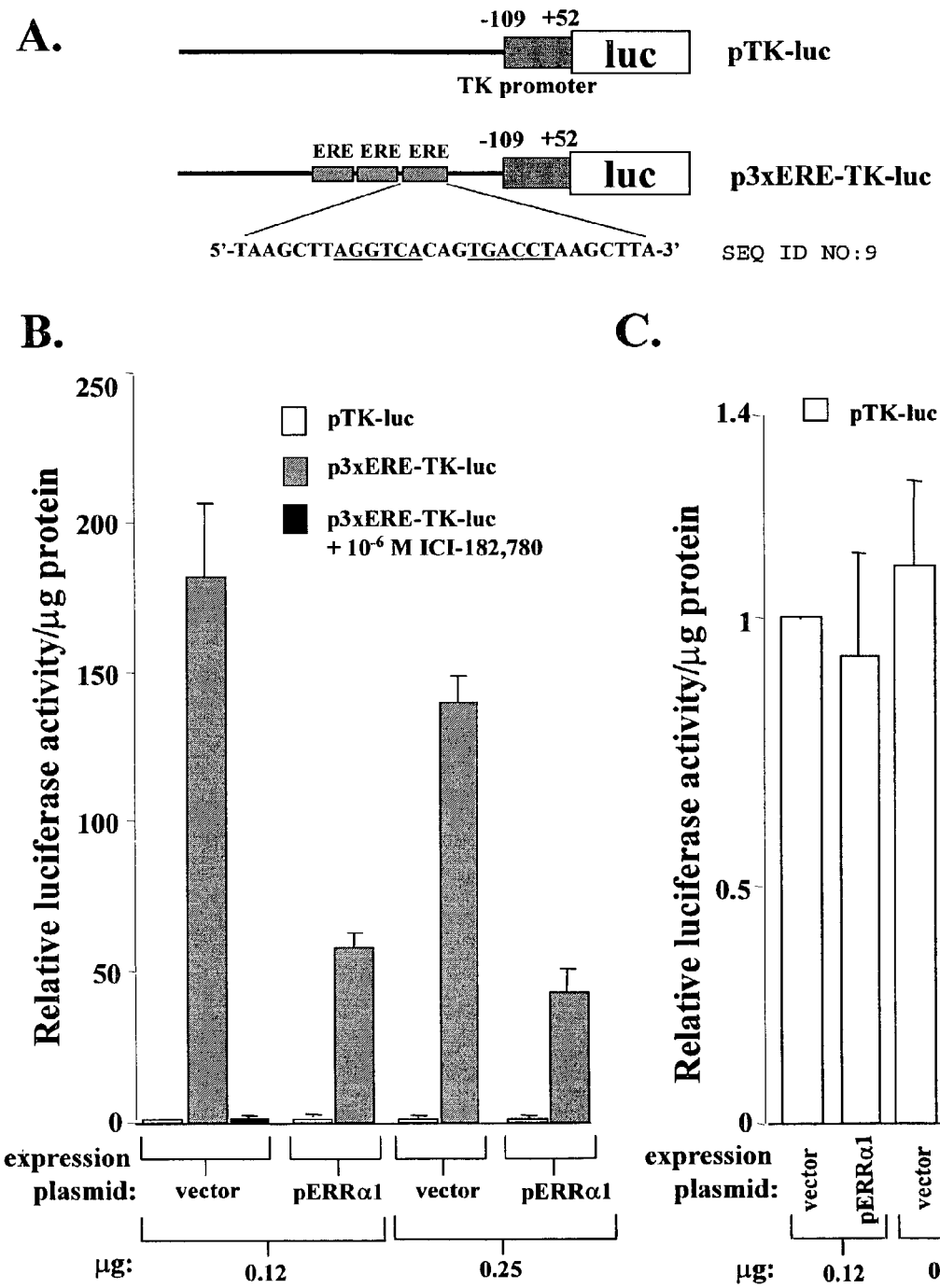
FIG. 14 shows down-modulation of ERE-dependent, ER-stimulated transcription by ERRα in MCF-7 cells. A, schematic representations of the pTK-luc and p3xERE-TK-luc reporter plasmids. Plasmid pTK-luc contains a minimal TK promoter, indicated by the shaded box, located immediately upstream of luciferase-encoding sequences, indicated by the open box. The numbers indicate nucleotides relative to the transcription initiation site. Plasmid p3xERE-TK-luc is identical in sequence to plasmid pTK-luc except for the insertion of three tandem copies of the consensus palindromic ERE sequence 5'-TAAGCTT<u>AGGTCA</u>CAG<u>TGACCT</u>AAGCTTA-3', indicated by the hatched boxes. B, ERRα down-modulates ER-stimulated transcription in MCF-7 cells. MCF-7 cells were co-transfected in parallel with 0.5 µg of pTK-luc or p3xERE-TK-luc and 0.12 or 0.25 µg of pcDNA3.1-hERRα1 or its empty parental vector pcDNA3.1. After incubation for 48 h in medium containing FBS, the cells were harvested and assayed for luciferase activity, with normalization to the protein concentration of each extract. The data are presented relative to the activity observed in the cells co-transfected with pTK-luc and 0.12 µg of vector pcDNA3.1. They represent the means plus S.E. from three separate experiments. The black bar represents data obtained from cells incubated in the presence of $1\times10^{-6}$ M anti-estrogen ICI-182,780. C, ERRα does not affect transcription of ERE-negative pTK-luc in MCF-7 cells. The data are taken from panel B but with the ordinate greatly expanded.

ERRα Represses Transcription in MCF-7 Cells: Because ERRα can interfere with the binding of ERα to this ERE, might it affect estrogen-responsive transcription? To answer this question, we co-transfected ERα-positive mammary MCF-7 cells in parallel with p3xERE-TK-luc, a reporter plasmid containing three tandem copies of this ERE (FIG. 14A) or the ERE-negative control plasmid, pTK-luc, together with 0.12 or 0.25 μg of the ERRα1 expression plasmid, pcDNA3.1-hERRα1, or the empty parental expression plasmid, pcDNA3.1. After incubation for 48 h in medium containing whole FBS, the cells were harvested and assayed for luciferase activity. The presence of the EREs conferred an about 150-fold increase in transcriptional activity above the level observed in the cells transfected with the ERE-negative reporter plasmid (FIG. 14B). This ERE-dependent activity was extremely sensitive to treatment with the anti-estrogen ICI-182,780, indicating the activation is dependent upon ER and the presence of estrogens in the FBS (FIG. 14B). Overexpression of ERRα repressed this ERE-dependent transcriptional activity about 3-4-fold (FIG. 14B; see also FIG. 18B) while exhibiting little if any effect on expression of the control pTK-luc reporter plasmid (FIGS. 14, B and C). Thus, ERRα inhibits the estrogen-responsive activation of transcription from this ERE-containing promoter in this ER-positive MCF-7 cell line.

ERRα Modulates Estrogen-responsiveness in MCF-7 Cells: To directly examine the effect of ERRα on the response to estrogen, MCF-7 cells were cultured in medium containing estrogen-free charcoal-stripped FBS and cotransfected as described above but in the absence or presence of $E_2$. In the absence of exogenous $E_2$, p3xERE-TK-luc was expressed at an approximately 50-fold higher level than pTK-luc, activity that was largely ablated by treatment with the anti-estrogen ICI-182,780 (FIG. 15A). Once again, overexpression of ERRα repressed ERE-dependent transcription approximately 3-fold while having little if any effect on transcription of the control reporter (FIG. 15A).

The addition of $1\times10^{-10}$ M $E_2$, a physiological concentration, to the medium dramatically induced transcriptional activity of the ERE-containing reporter plasmid approximately 10-fold above the level observed in the absence of exogenous $E_2$ (FIG. 15, B versus A). Consistent with this induction being mediated by ER, it was completely eliminated by incubation of the cells with the anti-estrogen ICI-182,780 (FIG. 15B). Strikingly, overexpression of ERRα inhibited this $E_2$-mediated activation of transcription from the ERE-containing promoter 3-5-fold, while, again, having little if any affect on expression of the ERE-negative control, pTK-luc (FIG. 15B).

Lastly, when the co-transfected cells were incubated with $1\times10^{-8}$ M $E_2$, a non-physiological concentration, ERE-dependent transcription was stimulated an additional 3-fold over the level of activity observed with $10^{-10}$ M $E_2$ to a level approximately 30-fold above the activity observed in the absence of exogenous $E_2$ (FIG. 15C). Again, this activity was extremely sensitive to treatment with the anti-estrogen ICI-182,780 (FIG. 15C), consistent with high concentrations of $E_2$ generating high levels of liganded, active ER. However, overexpression of ERRα no longer inhibited this $E_2$-mediated activation of transcription from p3x ERE-TK-luc (FIG. 15C). Thus, we conclude that ERRα can modulate estrogen responsiveness when its concentration relative to $E_2$-occupied ERα is sufficient to allow effective competition for binding to the ERE.

ERRα Represses Transcription by an Active Mechanism: What is the mechanism by which ERRα inhibits ER-mediated transcriptional activation? One possibility is that it simply competes with ERα for mutually exclusive binding to EREs, thereby blocking binding of the transcriptional activator. Alternatively, ERRα may contain a regulatory domain(s) as well as a DNA binding domain that plays an active role in modulating transcription from ERE-containing promoters.

Figure 16:
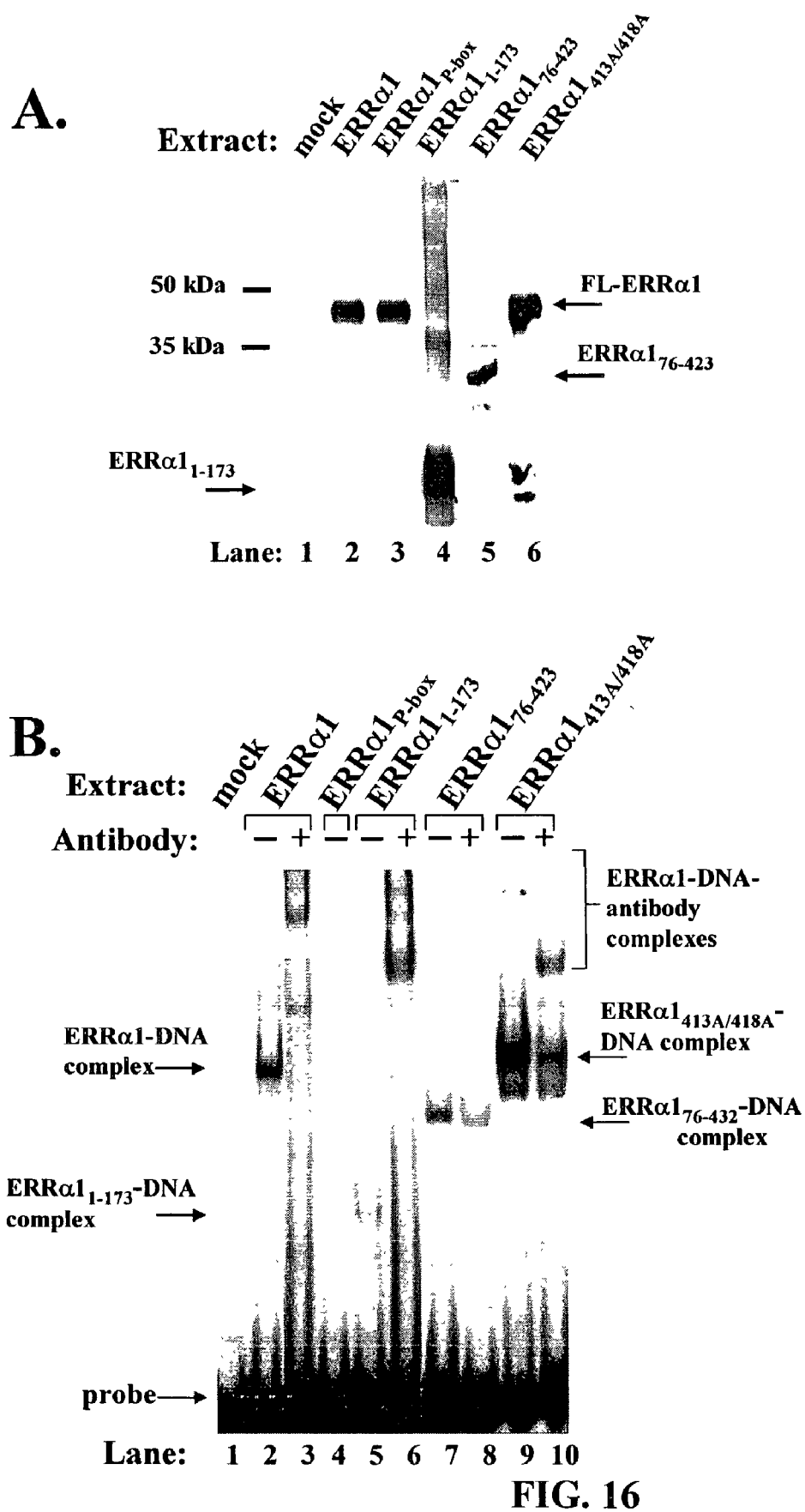
FIG. 16 shows DNA binding properties of variants of ERRα1. A, immunoblot of wild-type and variants of ERRα1 expressed in COS-M6 cells. Whole-cell extracts were prepared from COS-M6 cells transfected with the indicated expression plasmids. Five to 10 μg of whole-cell extract was analyzed for ERRα1-cross-reacting material by SDS-PAGE and immunoblotting as described under "Materials and Methods" in Example 2. Lane 1, pcDNA3.1; lane 2, pcDNA3.1-hERRα1; lane 3, pcDNA3.1-hERRα1$_{P\text{-}box}$; lane 4, pcDNA3.1-hERRα1$_{1\text{-}173}$; lane 5, pcDNA3.1-hERRα1$_{76\text{-}423}$ (15 to 30 μg); and lane 6, pcDNA3.1-hERRα1$_{413A/418A}$. FL, full-length B, EMSAs showing DNA binding activities of wild type and variants of ERRα1 to the palindromic ERE. Approximately 5 μg of protein from whole-cell extracts analyzed in panel A was incubated with the radiolabeled ERE probe as described in the legend to FIG. 13. The protein-DNA complexes were separated by electrophoresis in a native 5% polyacrylamide gel. To identify the DNA-protein complexes, the extracts were incubated with an ERRα1-specific antiserum before the addition of the probe in lanes 3, 6, 8, and 10. The arrows show the locations of the specific DNA-protein complexes and the free probe.
Figure 17:
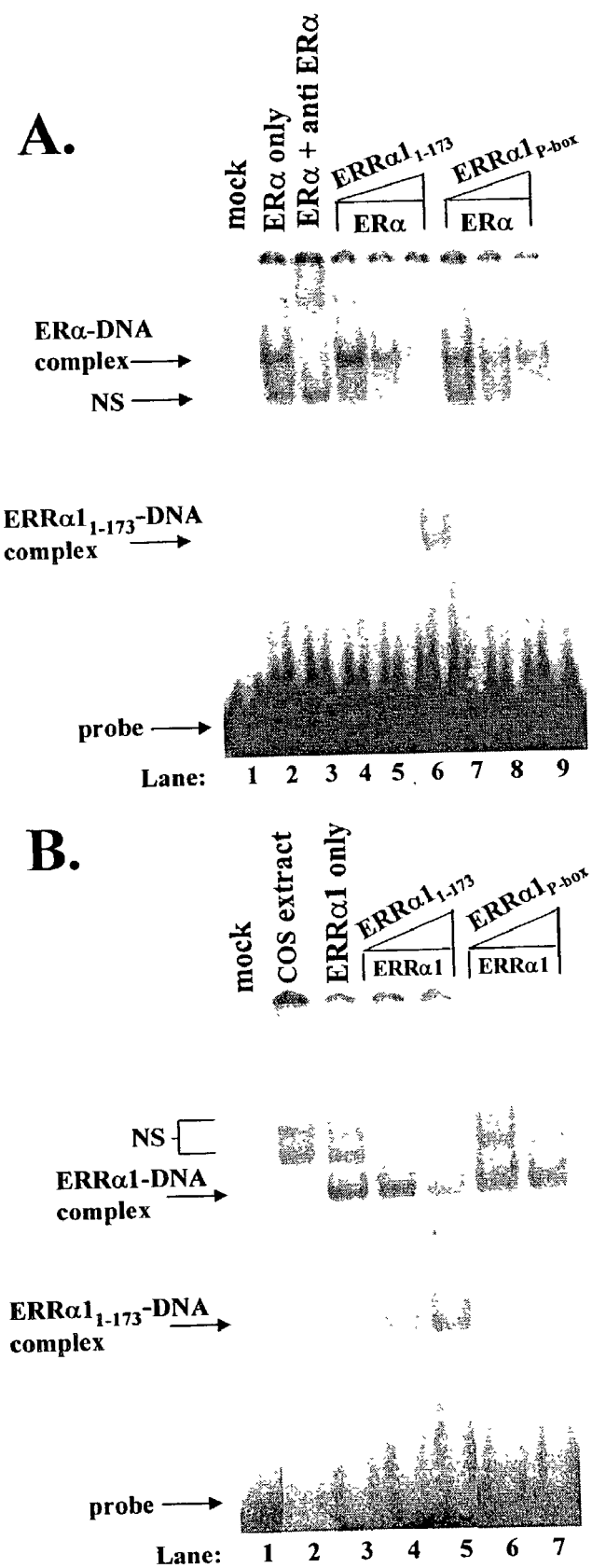
FIG. 17 shows competition between ERRα1 variants and ERα or ERRα1 for binding to the palindromic consensus ERE. A, ERRα1$_{1\text{-}173}$, but not ERRα1$_{P\text{-}box}$, competes with ERα for binding to the ERE. The radiolabeled ERE probe was incubated with a constant amount of whole-cell extract expressing ERα alone (lane 2) or together with increasing amounts of whole-cell extract containing overexpressed ERRα1$_{1\text{-}173}$ (lanes 4-6) or ERRα1$_{P\text{-}box}$ (lanes 7-9). Lane 1, probe alone; lane 3, extract was preincubated with the ERα-specific antibody, H222. The arrows indicate the specific and nonspecific (NS) DNA complexes and free probe. B, ERRα1$_{1\text{-}173}$, but not ERRα1$_{P\text{-}box}$, competes with wild-type ERRα1 for binding to the ERE. Experiments were performed as described in panel A above but with a constant amount of whole-cell extract containing overexpressed wild-type ERRα1 in place of ERα.

To distinguish between these two hypotheses, we constructed several variants of pcDNA3.1-hERRα1 (FIG. 12B) and determined their DNA binding and transcriptional activities. Plasmid pcDNA3.1-hERRα$1_{1-173}$ encodes a carboxyl-terminal-deleted variant of full-length ERRα1 that retains the amino-terminal A/B and DNA binding domains but lacks the E/F domains. Thus, ERRα$1_{1-173}$ is unable to bind putative ligands, ligand-dependent coactivator complexes, and, possibly, corepressor complexes. Immunoblotting with an antiserum specific for ERRα indicated that ERRα$1_{1-173}$ was expressed at levels comparable with, if not higher than full-length ERRα1 (FIG. 16A). EMSAs indicated that ERRα$1_{1-173}$ forms a protein-DNA complex with the palindromic ERE that can be immunoshifted with the ERRα-specific antiserum (FIG. 16B). Most importantly, ERRα$1_{1-173}$ efficiently competed for binding to this ERE with both ERα (FIG. 17A) and full-length ERRα1 (FIG. 17B). Therefore, synthesis of ERRα$_{11-173}$ in MCF-7 cells would also be predicted to result in inhibition of ER-mediated transcription if repression were caused simply by passive binding of ERRα to the ERE. However, contrary to the result observed with full-length ERRα1 (FIGS. 14B and 18B), overexpression of ERRα$1_{1-173}$ failed to repress transcription of either pTK-luc (FIG. 18A) or p3xERE-TK-luc (FIG. 18B); rather, it slightly enhanced transcription of p3xERE-TK-luc (FIG. 15B).

A second variant examined was ERRα$1_{76-423}$. This amino-terminal-deleted variant of ERRα1 lacks the A/B domain but retains the entire ligand and DNA binding domains (FIG. 12B). Immunoblots indicated that ERRα$1_{76-423}$ appeared to accumulate in transfected cells to somewhat lower levels than full-length ERRα1 (FIG. 16A). It is unclear whether the ERRα$1_{76-423}$ variant protein lacks some of the epitopes recognized by the polyclonal ERRα-specific antiserum used here, thus resulting in it being detected at lower efficiency, or that it actually accumulated to lower levels because of differences in rates of synthesis or stability. Regardless, sufficient quantities of protein accumulated for studies of DNA binding and transcriptional activity. As expected, ERRα$1_{76-423}$ was found both to bind to the palindromic ERE (FIG. 16B) and to repress transcription of p3xERE-TK-luc approximately 2-3-fold (FIG. 18B). Thus, although both ERRα$1_{76-423}$ and ERRα$1_{1-173}$ bind to the ERE, only ERRα$1_{76-423}$ represses ERE-dependent transcription. Therefore, a domain(s) of ERRα mapping within the carboxyl-terminal region of the protein in addition to its DNA binding domain is required for repression. These findings support an active model of transcriptional repression in which ERRα represses transcription by recruiting cellular corepressor(s) to the promoter.

As is true for most NRs, ERRα contains a coactivator binding motif or NR box. The ERRα1 NR box, located between amino acids 413 and 418, is comprised of the sequence LXLXXL (SEQ ID NO:17). This sequence differs slightly from the consensus NR box motif, LXLXXL (38-42) (SEQ ID NO:17). To examine the effect of inactivation of this coactivator binding motif on transcriptional activity, we constructed pcDNA3.1-hERRα1$_{413A/418A}$. The ERRα1 variant encoded by this plasmid contains alanine substitution mutations in place of the leucine residues at amino acids 413 and 418. Immunoblots indicated that ERRα1$_{413A/418A}$ efficiently accumulated in transfected cells (FIG. 16A). EMSAs showed that it specifically bound the palindromic ERE (FIG. 16B). Interestingly, ERRα1$_{413A/418A}$ repressed ERE-dependent transcription more efficiently than did full-length ERRα1, i.e. approximately 5-8-fold versus 3-4-fold, respectively (FIG. 18B). Somewhat surprisingly, ERRα1$_{413A/418A}$ up-regulated ERE-independent or TK-luc transcription approximately 2-fold (FIG. 18A), likely the result of sequestration by overexpressed ERRα1$_{413A/418A}$ of corepressors utilized by this control promoter. Thus, the repressive effect of ERRα1$_{413A/418A}$ on ERE-dependent transcription was 10-16-fold if normalized to the control. Quite likely, ERRα contains both corepressor and coactivator binding domains, with these domains acting in concert to determine the overall effect of ERRα on transcription. Thus, inactivation of the coactivator binding NR box motif potentiates repression by ERRα.

Last, we constructed pcDNA3.1-hERRα1$_{P-box}$. This plasmid encodes a variant of ERRα1 containing three amino acid substitution mutations within the DNA binding domain (FIG. 12B). ERRα1$_{P-box}$ accumulated to normal levels in transfected cells (FIG. 16A). As expected, it was incapable of binding to the palindromic ERE (FIG. 16B). ERRα1$_{P-box}$ also failed to interfere with the binding of either ERα (FIG. 17A) or wild-type ERRα1 to the palindromic ERE (FIG. 17B). Most interestingly, overexpression of ERRα1$_{P-box}$ led to a 2-3-fold induction of ERE-dependent transcription (FIG. 18) rather than repression or no effect. Induction could not have been a consequence of sequestration of endogenous ERRα away from the ERE via protein-protein interactions since ERRα1$_{P-box}$ did not interfere with binding of wild-type ERRα1 to the ERE. Rather, ERRα1$_{P-box}$ likely sequestered cellular corepressors away from DNA-bound endogenous ERRα, thereby relieving repression. These findings provide further support for the hypothesis that ERRα probably functions as a repressor of E$_2$-stimulated, ERE-dependent transcription via an active mechanism.

Figure 18:
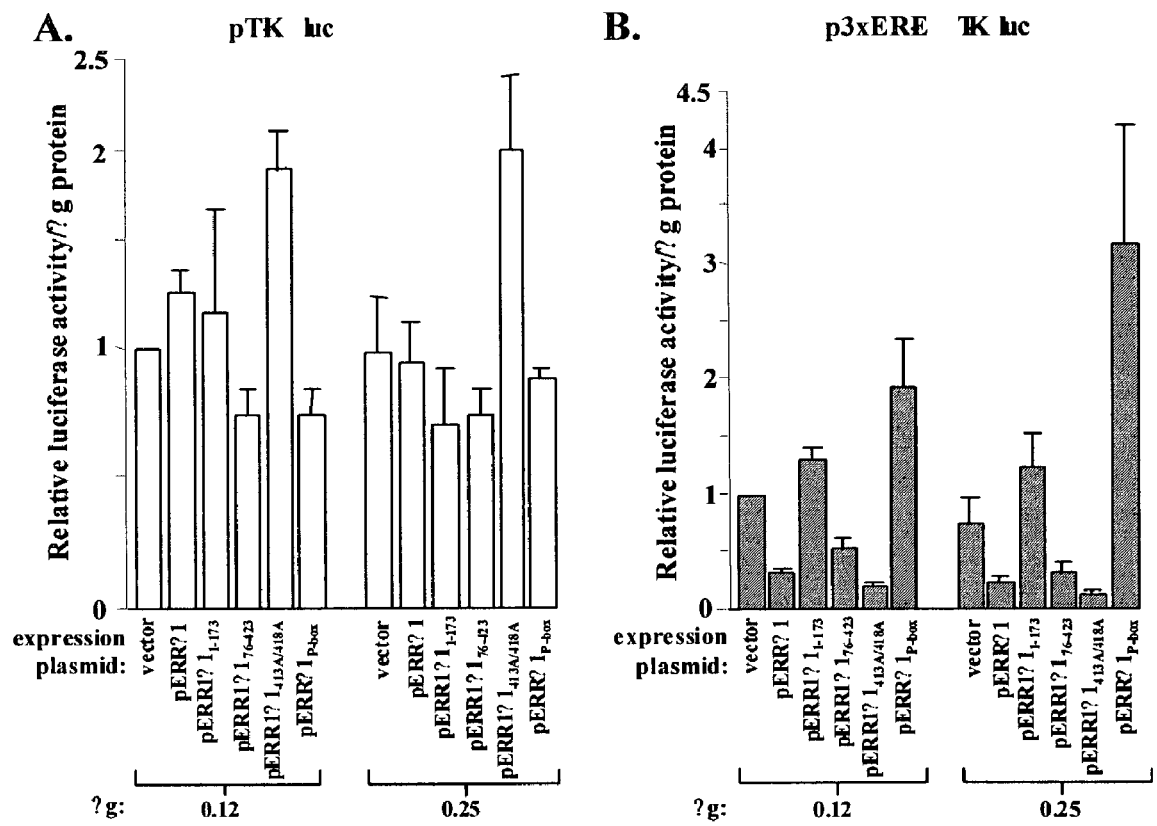
FIG. 18 shows that ERRα represses transcription by an active silencing mechanism. MCF-7 cells were co-transfected with 0.5 μg of (A) pTK-luc or (B) p3xERE-TK-luc and 0.12 μg or 0.25 μg of the empty vector pcDNA3.1, pcDNA3.1-hERRα1, pcDNA3.1-hERRα1$_{1\text{-}173}$, pcDNA3.1-hERRα1$_{76\text{-}423}$, pcDNA3.1-hERRα1$_{413A/418A}$, or pcDNA3.1-hERRα1$_{P\text{-}box}$. After incubation for 48 h in medium containing whole FBS, the cells were harvested, and luciferase activity was determined with normalization to the protein concentration of each extract. The data are presented in panel A relative to the activity observed with pTK-luc plus 0.12 μg of pcDNA3.1; they are presented in panel B relative to the activity observed with p3xERE-TK-luc plus 0.12 μg pcDNA3.1. All data shown represent means plus the S.E. from three separate experiments, each performed in triplicate.
Figure 19:
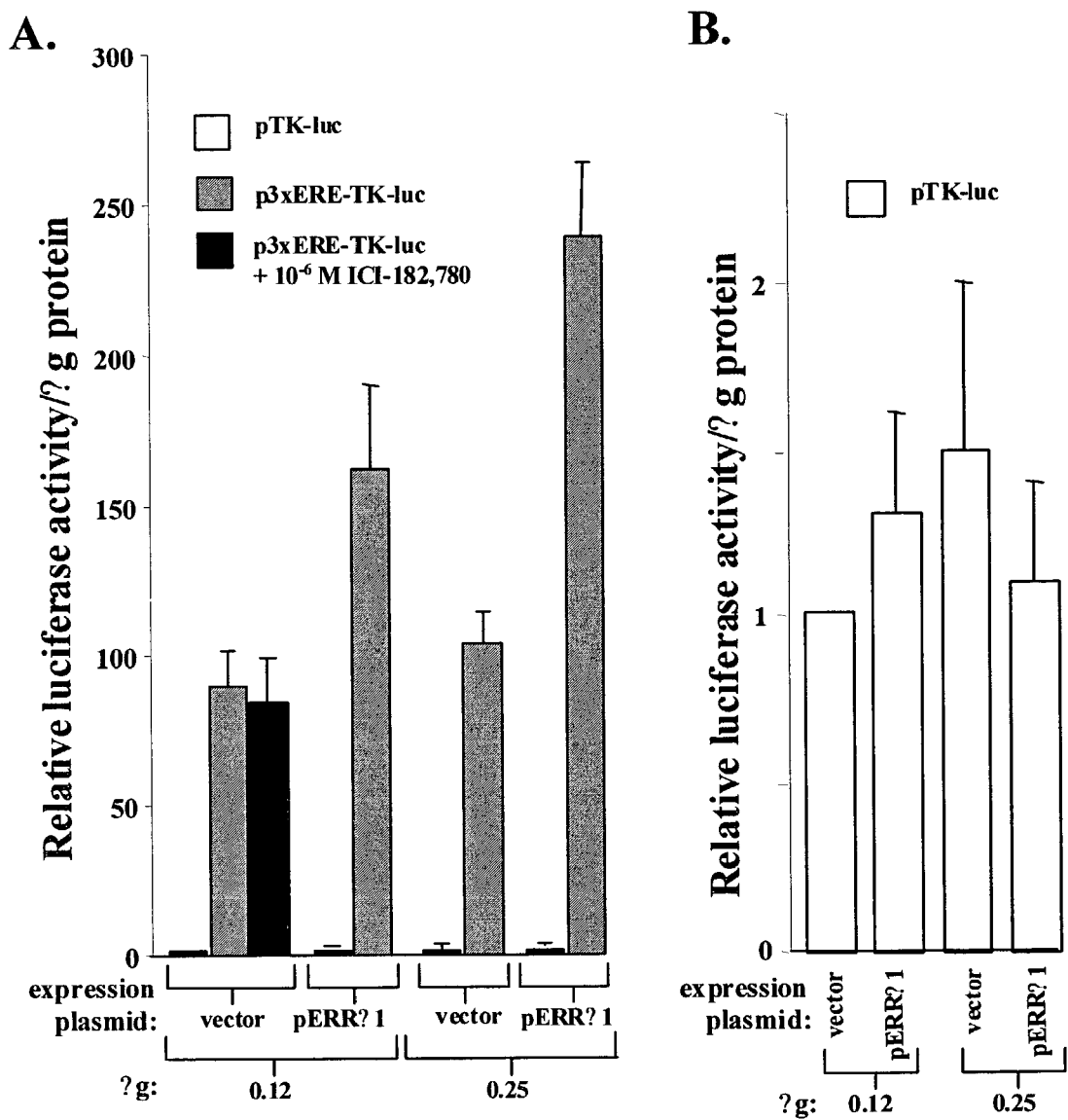
FIG. 19 shows that ERRα activates rather than represses ERE-dependent transcription in HeLa cells. Experimental details are identical to the ones described in FIG. 14, except that ER-negative HeLa cells were used in place of ER-positive MCF-7 cells. The data in panels A and B are presented in the same format as in FIG. 14, panels B and C, respectively.

ERRα Activates Transcription in HeLa Cells: Our finding that ERRα represses transcription from an ERE-controlled promoter was somewhat surprising since most reports in the literature conclude that ERR family members function as transcriptional activators of ERE-dependent transcription (17-31). To determine whether the transcriptional repression observed here was dependent upon the cell line, we repeated the cotransfection experiments as described above except using ER-negative HeLa cells in place of ER-positive MCF-7 cells (FIG. 19). Contrary to the results obtained in MCF-7 cells (FIGS. 14B and 18B), overexpression of ERRα in HeLa cells resulted in a 2.5-fold activation of transcription from the p3xERE-TK-luc reporter plasmid (FIG. 19A). A similar level of ERE-dependent activation was also observed in CV-1 and COS-M6 cells, other ER-negative cell lines. Thus, ERRα is a constitutive, estrogen-independent activator of transcription in these ER-negative cell lines. We conclude that ERRα can function as either a repressor or activator of ERE-dependent transcription in a cell type-specific manner.

Also noteworthy is the fact that the transcriptional activity of the ERE-containing p3xERE-TK-luc plasmid was already approximately 100-fold higher than that of its matched ERE-negative control plasmid, pTK-luc, even in the absence of overexpressed ERRα1 (FIG. 19, A versus B). Unlike in MCF-7 cells (FIG. 14B), in HeLa cells this ERE-dependent activity was completely insensitive to the anti-estrogen ICI-182780 (FIG. 19A) and, therefore, not mediated by ERs. Because HeLa cells contain high endogenous levels of ERRα (Ref. 32, data not shown), we conclude that endogenous ERRα, not ERα, likely mediated this high ERE-dependent transcriptional activity in these cells. Furthermore, the only modest induction observed in HeLa cells with overexpressed ERRα1 was likely due to the already abundant presence of endogenous ERRα. Thus, we conclude that ERRα is a strong constitutive activator of ERE-dependent transcription in HeLa cells.

Discussion

We examined here the transcriptional properties of ERRα when it acts via binding an ERE. We showed that ERRα directly competes with ERα for binding to a consensus palindromic ERE and down-modulates the transcriptional response to estrogen in an ERE-dependent manner in MCF-7 cells (FIGS. 14 and 15). Using variants of ERRα1, we further showed that repression is not simply the result of ERRα interfering with the binding of ERα to DNA; rather, it occurs via an active mechanism. Interestingly, ERRα functions as an activator rather than a repressor of this same promoter via its EREs in ER-negative HeLa cells (FIG. 19). Thus, ERRα operates as an active repressor or activator of ERE-dependent transcription based upon other properties of the cell.

Down-modulation of Estrogen Response by ERRα: What is the mechanism by which overexpression of ERRα1 in ER-positive MCF-7 cells leads to antagonism of the response of an ERE-containing promoter to estrogens? We showed that ERRα competes with ERα for binding to the consensus palindromic ERE. We hypothesize that estrogen responsiveness is governed by the percentage of EREs occupied by ERα, with ERE occupancy determined by the relative concentrations of E$_2$-activated ERα and ERRα in the cell. MCF-7 cells contain high endogenous levels of ERα (33) that exist in a ligand-activated complex when E$_2$ is present. In this case, most EREs are bound by ligand-activated ERα, and expression of the reporter gene is high (FIG. 15C). On the other hand, when ERRα is overexpressed and there is little ligand-activated ERα present, most EREs are bound by ERRα, and expression of the reporter gene is low (FIG. 15A). In this way, expression of the ERE-containing promoter is regulated by cross-talk between these two nuclear receptors. Thus, the level of expression of an ERE-dependent gene depends in part upon the relative amounts of ERRα and ligand-activated ERα in the cell.

Mechanism of Repression by ERRα: Previously, Burbach et al. (43) showed that COUP-TF1 represses estrogen-dependent stimulation of the oxytocin gene by simply competing with ERα for binding to an ERE. However, based upon analysis of variants of ERRα, we conclude here that repression by ERRα involves, instead, an active silencing mechanism. First, ERRα1$_{1-173}$ retains its DNA binding activity (Ref. 21; results section in this Example), yet failed to repress transcription (FIG. 18). Thus, simply blocking the binding of ERα is not sufficient for ERRα to repress ERE-mediated transcription. Second, ERRα1$_{76-423}$, a variant lacking the amino-terminal domain but retaining both the DNA binding and carboxyl-terminal domains repressed transcription as well as full-length ERRα1 (FIG. 18). Therefore, in addition to the DNA binding domain, a region within the carboxyl terminus is required for ERRα to repress E$_2$-stimulated, ERE-dependent transcription. Third, ERRα1$_{413A/418A}$, a variant containing mutations only within the LXLXXL (SEQ ID NO:17) coactivator binding NR box motif, repressed E$_2$-stimulated, ERE-dependent transcription more efficiently than did wild-type ERRα1 (FIG. 18). We interpret this latter result to indicate that ablation of the NR box disrupts the balance of ERRα-bound co-regulators, thereby allowing any putative corepressor bound to ERRα to act more effectively. Last, ERRα1$_{P-box}$, a variant whose DNA binding activity was abrogated but coregulator binding domains were left intact, specifically up-regulated rather than antagonized ERE-dependent transcription (FIG. 18). This latter finding is likely a consequence of repression domains present within ERRα1$_{P-box}$ competing with endogenous wild-type ERRα for binding cellular corepressors, thereby preventing endogenous ERE-bound ERRα from antagonizing transcription. Furthermore, ERRα can function as an active repressor even in the absence of ERα. For example, we have found that ERRα represses SV40 late gene expression in ER-negative CV-1 cells both from the natural ERRα response elements overlapping the transcription initiation site of the SV40 major late promoter (11) and when this ERRα response element is relocated to 50 bp upstream of the transcription initiation site. Taken together with previous findings of others (20), these results provide evidence that ERRα contains both repression and activation domains. We have also shown elsewhere (44) that silencing mediator for retinoid and thyroid hormone receptors (SMRT) is one of the corepressors that can bind ERRα, binding within the hinge region of ERRα. Additional experiments will be needed to identify the corepressors of ERRα and to definitively map their sites of binding.

Contrary to our findings with ERRα1$_{1-173}$, Zhang and Teng (21) reported that the amino-terminal region of ERRα1 contains repressor activity. However, they assayed the effects of Gal4DBD-ERRα1 chimeras on expression of a Gal4 reporter rather than non-chimeric variants of ERRα1 binding via the ERRα DNA binding domain to an ERE. Whether these differences in experimental design can account for the seemingly contradictory conclusion is not yet clear.

ERRα has also been shown to bind ERα directly (11). Thus, alternative, non-mutually exclusive hypotheses to explain the ability of ERRα to down-modulate ERE-dependent transcription include (i) ERRα forming true heterodimers with ERα that can bind EREs and (ii) ERRα interacting with ERα in ways that abrogates the ability of ERα to bind EREs. However, we failed to observe ERα-ERRα heterodimeric complexes in either the experiments presented here or EMSAs performed using whole-cell extracts obtained from COS-M6 cells co-transfected with the ERα and ERRα expression plasmids. Moreover, the presence of ERRα1$_{P-box}$ failed to interfere with the binding of ERα to DNA. Taken collectively, these data indicate that ERRα likely functions as a repressor independently of any ability to bind ERα.

Activation of Transcription by ERRα: Confirming prior reports (17-31), we have also observed that ERRα can activate transcription from an ERE-regulated promoter (FIG. 19). We show here for the first time that whether ERRα functions as a repressor or activator of a specific promoter can depend upon the cell type (FIG. 14 versus 19). What factors determine the activity of ERRα? Several possibilities exist. First, the activities of ERRα might be ligand-dependent. Previous reports appear to be contradictory as to the existence of an exogenous activating ligand. One indicated that transcriptional activation by ERRα depends upon a component present in serum (17). Others claimed that ERRs are not activated by naturally occurring ligands (19, 20). In the experiments reported here, the same serum was present in the medium in which the HeLa and MCF-7 cells were cultured; nevertheless, ERRα exhibited markedly different activities in these cell types (FIG. 14 versus 19). Thus, if an activating ligand of ERRα exists in FBS, it probably does not exclusively determine the activity of ERRα. Furthermore, we found that charcoal-dextran treatment of the serum did not affect the silencing activity of ERRα (FIG. 15A), supporting the notion that ERRα functions as a repressor independently of an exogenous ligand. One alternative possibility is that various cell types may or may not endogenously synthesize the putative ligand of ERRα, thereby determining the transcriptional properties of ERRα in those cells. Second, the differences in transcriptional activity observed here might be a reflection of differences in the co-regulators present in these cell types. Third, by analogy with ERα (45-48), the phosphorylation state of ERRα may affect its functional activities. Indeed, Sladek et al. (26) showed that murine ERRα can be phosphorylated in vivo. Likewise, we have found that human ERRα1 can be phosphorylated in vitro by MAP kinase.

Model for ERRα Modulation of Estrogen Responsiveness: Based upon the data presented here, we postulate that ERRα plays key roles in the regulation of estrogen-responsive genes by efficiently binding EREs (Ref. 11; data not shown), leading either to modulation of the response to estrogens or functional substitution for ERα as a constitutive activator of ERE-dependent transcription. Furthermore, the cellular concentrations of ERα and ERRα, together with the differential transcriptional properties of ERRα, determine the transcriptional response of an ERE-regulated promoter. For example, when the concentrations of both ERα and ERRα are low or the level of the repressor form of ERRα is high, an ERE-dependent gene is expressed at intermediate or low levels (FIG. 20, rows 1 and 2, respectively). Low and high concentrations of the repressor form of ERRα relative to high amounts of active ERα complex yield intermediate or high ERE-dependent gene expression (FIG. 20, rows 3 and 4, respectively). Last, in the absence of active ERα, the activator form of ERRα can constitutively activate ERE-dependent transcription (FIG. 20, rows 5 and 6).

Both estrogens acting through ERs and kinase signaling pathways contribute to the initiation and progression of some breast cancers. Because ERRα plays multiple roles in regulation of ERE-dependent transcription (FIG. 20), we hypothesis that the functionality of ERRα, possibly modulated by kinase signaling events, leads to the development or progression of some breast cancers. We propose that the silencing activity of ERRα tightly regulates estrogen responsiveness in normal breast cells (FIG. 20, rows 1 and 2). Some cancerous cells attain very high levels of ERα, thereby maximizing the mitogenic affects of estrogen (FIG. 20, rows 3 and 4). In addition, some breast cancers present as ER-negative (49-51) or develop resistance to hormonal treatment (52). Under either of these circumstances, ERRα may functionally substitute for ERα if it is in an active form, thereby constitutively activating ERE-regulated transcription (FIG. 20, rows 5 and 6). Thus, the conversion of ERRα from a repressor to an activator by a mechanism(s) yet to be determined may be a critical step in the progression to a hormone-independent phenotype.

References

1. Evans, R. M. (1988) Science 240, 889-895.
2. Beato, M. (1989) Cell 56, 335-344.
3. Truss, M., and Beato, M. (1993) Endocr. Rev. 14, 459-479.
4. Tsai, M. J., and O'Malley, B. W. (1994) Annu. Rev. Biochem. 63, 451-486.
5. Mangelsdorf, D. J., Thummel, C., Beato, M., Herrlich, P., Schultz, G., Umesomo, K., Blumberg, B., Kastner, P., Mark, M., and Chambon, P. (1995) Cell 83, 835-839.
6. Beato, M., Herrlich, P., and Schülz, G. (1995) Cell 83, 851-857.
7. Enmark, E., and Gustafsson, J-. G. (1996) Mol. Endocrinol. 10, 1293-1307.
8. Blumberg, B., and Evans, R. M. (1998) Genes Dev. 12, 3149-3155.
9. Kliewer, S. A., Lehmann, J. M., and Willson, T. M. (1999) Science 284, 757-760.
10. Giguère, V., Yang, N., Segui, P., and Evans, R. M. (1988) Nature 331, 91-94.
11. Johnston, S. D., Liu, X., Zuo, F., Eisenbraun, T. L., Wiley, S. R., Kraus, R. J., and Mertz, J. E. (1997) Mol. Endocrinol. 11, 342-352.
12. Shigeta, H., Zuo, W., Yang, N., DiAugustine, R., and Teng, C. T. (1997) J. Mol. Endocrinol. 19, 299-309.
13. Chen, F., Zhang, Q., McDonald, T., Davidoff, M. J., Bailey, W., Bai, C., Liu, Q., and Caskey, C. T. (1999) Gene 228, 101-109.
14. Hong, H., Yang, L., and Stallcup, M. R. (1999) J. Biol. Chem. 274, 22618-22626.
15. Heard, D. J., Norby, P. L., Holloway, J., and Vissing, H. (2000) Mol. Endocrinol. 14, 382-392.
16. Vanacker, J.-M., Pettersson, K., Gustafsson, J.-. G., and Laudet, V. (1999) EMBO J. 18, 4270-4279.
17. Vanacker, J., M., Bonnelye, E., Chopin-Delannoy, S., Delmarre, C., Cavailles, V., and Laudet, V. (1999) Mol. Endocrinol. 13, 764-773.
18. Yang, C., and Chen, S. (1999) Cancer Res. 59, 4519-4524.
19. Xie, W., Hong, H., Yang, N. N., Lin, R. J., Simon, C. M., Stallcup, M. R., and Evans, R. M. (1999) Mol. Endocrinol. 13, 2151-2162.
20. Zhang, Z., and Teng, C. T. (2000) J. Biol. Chem. 275, 20837-20846.
21. Zhang, Z., and Teng, C. T. (2001) Mol. Cell. Endocrinol. 172, 223-233.
22. Tremblay, G. B., Kunath, T., Bergeron, D., Lapointe, L., Champigny, L., Bader, J.-A., Rossant, J., and Giguère, V. (2001) Genes Dev. 15, 833-838.
23. Lu, D., Kiriyama, Y., Lee, K. Y., and Giguère, V. (2001) Cancer Res. 61, 6755-6761.
24. Coward, P., Lee, D., Hull, M. V., and Lehmann, J. M. (2001) Proc. Natl. Acad. Sci. U. S. A. 98, 8880-8884.
25. Yang, N., Shigeta, H., Shi, H., and Teng, C. T. (1996) J. Biol. Chem. 271, 5795-5804.
26. Sladek, R., Bader, J.-A., and Giguère, V. (1997) Mol. Cell. Biol. 17, 5400-5409.
27. Bonnelye, E., Vanacker, J. M., Spruyt, N., Alric, S., Fournier, B., Desbiens, X., and Laudet, V. (1997) Mech. Dev. 65, 71-85.
28. Bonnelye, E., Vanacker, J.-M., Dittmar, T., Begue, A., Desbiens, X., Denhardt, D. T., Aubin, J. E., Laudet, V., and Fournier, B. (1997) Mol. Endocrinol. 11, 905-916.
29. Yang, C., Zhou, D., and Chen, S. (1998) Cancer Res. 58, 5695-5700.
30. Vega, R. B, and Kelley, D. P. (1997) J. Biol. Chem. 272, 31693-31699.
31. Vanacker, J.-M., Delmarre, C., Guo, X., and Laudet, V. (1998) Cell Growth Differ. 9, 1007-1014.
32. Wiley, S. R., Kraus, R. J., Zuo, F., Murray, E. E., Loritz, K., and Mertz, J. E. (1993) Genes Dev. 7, 2206-2219.
33. Catherino, W. H., and Jordan, V. C. (1995) Cancer Lett. 92, 39-47.
34. Katzenellenbogen, J. A., Johnson, H. J., Jr., and Meyers, H. N. (1973) Biochemistry 12, 4085-4092.
35. Kraus, R. J., Shadley, L., and Mertz, J. E. (2001) Virology 287, 89-104.
36. Kraus, R. J., Mirocha, S. J., Stephany, H. M., Puchalski, J. R., and Mertz, J. E. (2001) J. Virol. 75, 867-877.
37. Reese, J. C., and Katzenellenbogen, B. S. (1991) Nucleic Acids Res. 19, 6595-6602.
38. Torchia, J., Glass, C., and Rosenfeld, M. G. (1998) Curr. Opin. Cell Biol. 10, 373-383.
39. Perlmann, T., and Evans, R. M. (1997) Cell 90, 391-397.
40. Horwitz, K. B., Jackson, T. A., Bain, D. L., Richer, J. K., Takimoto, G. S., and Tung, L. (1996) Mol. Endocrinol. 10, 1167-1177.
41. Chen, J. D., and Li, H. (1998) Crit. Rev. Eukaryotic Gene Expression 8, 169-190
42. Jenster, G. (1998) Mol. Cell. Endocrinol. 143, 1-7.
43. Burbach, J. P. H., Lopes da Silva, S., Cox, J. J., Adan, R. A. H., Cooney, A. J., Tsai, M., and Tsai, S. Y. (1994) J. Biol. Chem. 269, 15046-15053.
44. O'Reilley, G. H. (2000) Regulation of the SV40 Late Promoter by Nuclear Receptors and Large T Antigen,. Ph.D. thesis, University of Wisconsin-Madison
45. Kato, S., Endoh, H., Masuhiro, Y., Kitamoto, T., Uchiyama, S., Sasaki, H., Masushige, S., Gotoh, Y., Nishida, E., Kawashima, H., Metzger, D., and Chambon, P. (1995) Science 270, 1491-1494.
46. Bunone, G., Briand, P. A., Miksicek, R. J., and Picard, D. (1996) EMBO J. 15, 2174-2183.
47. Joel, P. B., Smith, J., Sturgill, T. W., Fisher, T. L., Blenis, J., and Lannigan, D. A. (1998) Mol. Cell. Biol. 18, 1978-1984.
48. Joel, P. B., Traish, A. M., and Lannigan, D. A. (1998) J. Biol. Chem. 273, 13317-13323.
49. Knight, W. A., Livingston, R. B, Gregory, E. J., and McGuire, W. L. (1977) Cancer Res. 37, 4669-4671.
50. Allegra, J. C., Lippman, M. E., Thompson, E. B., Simon, R., Barlock, A., Green, L., Huff, K. K., Do, H. M. T., Aitken, S. C., and Warren, R. (1980) Eur. J. Cancer 16, 323-331.
51. Clark, G. M., and McGuire, W. L. (1983) Breast Cancer Res. Treat. Suppl: S3, 69-72
52. Murphy, C. S., and Jordan, V. C. (1990) Receptor 1-2, 65-81.

EXAMPLE 3

Estrogen-related Receptor α and Estrogen-related Receptor γ Associate with Unfavorable and Favorable Biomarkers, Respectively, in Human Breast Cancer Abstract The importance of estrogen-related receptors (ERRs) in human breast cancer was assessed by comparing their mRNA profiles with established clinicopathologic indicators and mRNA profiles of estrogen receptors (ERs) and ErbB family members. Using real-time quantitative polymerase chain reaction assays, mRNA levels of ERα, ERβ, EGFR (epidermal growth factor receptor), ErbB2, ErbB3, ErbB4, ERRα, ERRβ, and ERRγ were determined in unselected primary breast tumors (n=38) and normal mammary epithelial cells (MECs) enriched from reduction mammoplasties (n=9). ERRα showed potential as a biomarker of unfavorable clinical outcome and, possibly, hormonal insensitivity. ERRα mRNA was expressed at levels greater than or equivalent to ERα mRNA in 24% of unselected breast tumors, and generally at higher levels than ERα in the PgR-negative tumor subgroup (1-way ANOVA with repeated measures, P=0.030). Increased ERRα levels associated with ER-negative (Fisher's exact, P=0.003) and PgR-negative tumor status (Fisher's exact, P=0.006; Kruskal-Wallis ANOVA, P=0.021). ERRα levels also correlated with expression of ErbB2 (Spearman's rho, P=0.005; cluster analysis), an indicator of aggressive tumor behavior. Thus, ERRα was the most abundant nuclear receptor in a subset of tumors that tended to lack functional ERα and expressed ErbB2 at high levels. Consequently, ERRα may potentiate constitutive transcription of estrogen response element-containing genes independently of ERα and antiestrogens in ErbB2-positive tumors. ERRβ's potential as a biomarker remains unclear: it showed a direct relationship with ERβ (Spearman's rho, P=0.0002; cluster analysis) and inversely correlated with S-phase fraction (Spearman's rho, P=0.026). Unlike ERRα, ERRγ showed potential as a biomarker of favorable clinical course and, possibly, hormonal sensitivity. ERRγ was overexpressed in 75% of the tumors, resulting in the median ERRγ level being elevated in breast tumors compared to normal MECs (Kruskal-Wallis ANOVA, P=0.001). ERRγ overexpression associated with the hormonally responsive phenotype, ER- and PgR-positive status (Fisher's exact, P=0.054 and P=0.045, respectively; cluster analysis). Additionally, ERRγ expression correlated with levels of ErbB4 (Spearman's rho, P=0.052, cluster analysis), a likely indicator of preferred clinical course, and associated with diploid-typed tumors (Fisher's exact, P=0.042). Hence, determination of the status of ERRα and ERRγ may be of significant benefit in the treatment of breast cancer, potentially by predicting the efficacy of hormonal and ErbB2-based therapies. Moreover, ERRα and ERRγ are candidate targets for therapeutic development.

Introduction

Breast cancer afflicts one in eight women in the United States over their lifetime (1). ERα (NR3A1, (2)) mediates estrogen responsiveness (reviewed in (3)) and plays crucial roles in the etiology of breast cancer (reviewed in (4)). It has been developed into the single most important genetic biomarker and target for breast cancer therapy. ERα is present at detectable levels by ligand-binding and immunohistochemical assays in approximately 75% of clinical breast cancers. Selection of patients with ERα-positive breast tumors increases endocrine-based therapy response rates from about one-third in unselected patients to about one-half in patients with ERα-positive tumors (5). Since expression of PgR is dependent upon ERα activity, further selection of patients with ERα- and PgR-positive tumors enhances the breast cancer hormonal therapy response rate to nearly 80% (5). Although ERβ (NR3A2 (2)) also mediates responses to estrogens (reviewed in (3)), its roles in breast cancer are not as well understood. Reports have linked ERβ expression with low tumor aggressiveness (6) and higher levels of proliferation markers in the absence of ERα (7).

Members of the ErbB family of transmembrane tyrosine kinase receptors have been implicated in the pathogenesis of breast cancer. The members include EGFR (also HER1; ErbB1), ErbB2 (HER2; Neu), ErbB3 (HER3) and ErbB4 (HER4) (reviewed in (8)). ErbB members stimulate signal transduction pathways that involve MAPK. In response to initial binding of EGF-like peptide hormones, ErbB members form homodimers and heterodimers in various combinations to recruit distinct effector proteins [reviewed in (9)]. Although ErbB2 has not been demonstrated to interact directly with peptide hormones, it serves as a common regulatory heterodimer subunit with other ligand-bound ErbB members (reviewed in (10, 11)). Unlike the other ErbB members, ErbB3 lacks intrinsic kinase activity and, therefore, is required to heterodimerize with other ErbB members to participate in signaling (12).

Independent overexpression of either EGFR (reviewed in (13)) or ErbB2 (reviewed in (14)) associates with ER-negative tumor status, indicates aggressive tumor behavior, and predicts poor prognosis. Moreover, patients whose tumors coexpress both EGFR and ErbB2 exhibit a worse outcome than patients with tumors that overexpress only one of these genes (15, 16). Overexpression of ErbB2, most often due to gene amplification, occurs in approximately 15-30% of all breast cancers ((17), reviewed in (14)). Some (18-23), but not all reports (24, 25), have implicated ErbB2 in the development of resistance to antiestrogens.

ErbB2 has been targeted for development of the successful clinical agent Herceptin (trastuzumab), a recombinant humanized monoclonal antibody directed against this receptor's ectodomain (reviewed in (26)). Herceptin has been shown to be a suitable option as a first-line single-agent therapy (27), but will likely prove most beneficial as an adjuvant (28, 29). Clinical trials are currently underway to evaluate the combination of Herceptin with antiestrogens as a rational approach to treating ERα-positive/ErbB2-overexpressing tumors (23). In the near future, Herceptin will also likely be evaluated in combination with the small molecule EGFR tyrosine kinase inhibitor ZD1829 (Iressa), since this ATP-mimetic has been shown to almost completely block transphosphorylation of ErbB2 via heterodimerization with EGFR in intact cells (30) and inhibits the growth of breast cancer cell lines overexpressing both EGFR and ErbB2 (31). Hence, a combination of ZD1829 and Herceptin may be particularly beneficial to those patients whose tumors coexpress EGFR and ErbB2.

The ability of ErbB3 and ErbB4 to predict clinical course is not as clearly recognized as that of EGFR and ErbB2. ErbB3 has been observed at higher levels in breast tumors than normal tissues, showing associations with unfavorable prognostic indicators including ErbB2 expression (32), lymph node-positive status (33), and tumor size. However, it also associated with ERα-positive status, a favorable marker of hormonal sensitivity (34). In stark contrast to ErbB2, higher levels of ErbB4 have been associated with ERα-positive status (34, 35), more differentiated histotypes (36) and a more favorable outcome (16).

Despite the utility of ERs and ErbB members as indicators of clinical course, there remains a great need to identify additional breast cancer biomarkers. A family of potential candidate biomarkers includes the orphan nuclear receptors ERRα (37-39), ERRβ (37, 40), and ERRγ (40-42) (NR3B1, NR3B2, and NR3B3, respectively (2)). These orphan receptors share significant amino acid sequence identity with ERα and ERβ. They also exhibit similar but distinct biochemical and transcriptional activities as the ERs. Each of the ERRs has been demonstrated to bind and activate transcription via consensus palindromic EREs (43-46) in addition to ERREs (39, 42, 44, 47-50), which are composed of an ERE half-site with a 5' extension of 3 base pairs. However, whereas ERs are ligand-activated transcription factors, the ERRs do not bind natural estrogens (37, 51). Instead, the ERRs may serve as constitutive regulators, interacting with transcriptional coactivators in vitro in the absence of ligands (45, 50, 52). Bulky amino acid side chains in the ligand binding pockets of ERRs substitute for the analogous ligand-induced interactions observed in ERα (52, 53). However, the ligand-binding pockets of the ERRs still allow binding of the synthetic estrogen diethylstilbestrol, but as an antagonist because it also disrupts coactivator interactions with ERRs (51). Similarly, the selective estrogen receptor modulator (SERM) 4-hydroxytamoxifen selectively antagonizes ERRγ in cell-based assays (46, 52, 54).

The transcriptional activity of each ERR depends upon the promoter and the particular cell line in which it is assayed as well as the presence of ERs (42-46, 48-51, 53-62). For example, whereas ERRα stimulates ERE-dependent transcription in the absence of ERα in HeLa cells, it down-modulates $E_2$-stimulated transcription in ERα-positive human mammary carcinoma MCF-7 cells via an active mechanism of repression (43). ERRα can also modulate transcription of at least some genes that are estrogen responsive and/or implicated in breast cancer such as pS2 (55), aromatase (59), osteopontin (57, 58) and lactoferrin (56, 61). Thus, the ERRs likely play important roles in at least some breast cancers by modulating or substituting for ER-dependent activities.

We sought to assess the potential utility of ERRs as novel breast cancer biomarkers in the context of ER and ErbB family members and established clinicopathological parameters. Hence, mRNA levels of ERs (ERα, ERβ), ErbB members (EGFR, ErbB2, ErbB3, ErbB4), and ERRs (ERRα, ERRβ, ERRγ) were characterized using real-time Q-PCR assays in a panel of 38 unselected primary breast cancers and 9 normal MEC preparations from mammoplastic reductions. These mRNA profiles were compared to established clinical biomarkers including ER and PgR protein levels determined by ligand-binding assays, as well as S-phase fraction and DNA ploidy determined by flow cytometry. The findings observed here indicate that ERRα and ERRγ may well be useful as negative and positive markers, respectively, of clinical course and, potentially, selection of appropriate therapies.

Materials and Methods

Tissue Sources: Random primary breast cancer samples were obtained from the National Breast Cancer Tissue Resource SPORE at Baylor College of Medicine (Houston, Tex.). Records of previously determined clinicopathologic tumor biomarkers were maintained at the SPORE, including ER-LB (ligand binding) and PgR-LB protein levels measured by the ligand-binding assay, and S-phase fraction and DNA ploidy determined by flow cytometry. The mRNA profiling studies were conducted in a blinded manner regarding these previously determined biomarkers. Mammary tissues from reduction mammoplasties were processed through collagenase digestion and differential centrifugation and filtration steps to isolate normal MECs. These enriched MECs were kindly provided by Dr. Stephen Ethier (University of Michigan-Ann Arbor) and Dr. Michael N. Gould (University of Wisconsin-Madison). The normal MECs were not expanded in culture in an effort to maintain in vivo RNA profiles. All use of human tissues was approved by the University of Wisconsin's Human Subjects Committee.

Real-time Q-PCR Assays: The mRNA abundances of ER, ErbB and ERR family members were determined by real-time Q-PCR assays. As detailed below, amplification of PCR products was continuously monitored by fluorescence facilitated by specific complex formation of SYBR Green I with double-stranded DNA (reviewed in (63)).

Total RNA was isolated from tissues using the Total RNeasy kit (Qiagen; Valencia, Calif.), treated with RNase-free DNase I (Ambion; Austin, Tex.), and again purified with the Total RNeasy kit. cDNA was synthesized by incubation of 10 µg total RNA with SuperScript II reverse transcriptase (Invitrogen Life Technologies; Carlsbad, Calif.) and 50 nmoles each of oligo $dT_{15}VN$ (where V=A, G, or C and N=any nucleotide) and random hexamers as primers in a total reaction volume of 100 µl at 45° C. for 1 h. The same amount of synthesized cDNA was used in each assay to normalize for variability in mRNA integrity and reverse transcriptase efficiency across the tissue samples. Quantitation of cDNA involved trace radiolabeling of a parallel cDNA synthesis reaction carried out in the presence of $[\alpha-^{32}P]dCTP$. Incorporated and total radiolabeled amounts were measured in triplicate by trichloroacetic acid precipitation and scintillation counting. Calculation of the total mass of cDNA synthesized was based upon the molar amount of nucleotides present in the reaction converted to mass and multiplied by the ratio of incorporated-to-total radiolabel. Q-PCR assays involving tissue samples employed 1 ng cDNA as template and were carried out in triplicate.

PCR primer sets were designed to promote efficient amplification by yielding products smaller than 150 bp in length. PCR products were verified by sequence analysis. The PCR primer set sequences and amplicon sizes were as follows: ERα forward primer 5'-GGAGGGCAGGGGTGAA-3' (SEQ ID NO:5) and reverse primer 5'-GGCCAGGCTGTTCTTCT-TAG-3' (SEQ ID NO:6), 100-bp amplicon; ERβ forward primer 5'-TTCCCAGCAATGTCACTAACTT-3' (SEQ ID NO:18) and reverse primer 5'-TTGAGGTTCCGCATA-CAGA-3' (SEQ ID NO:19), 137-bp amplicon; EGFR forward primer 5'-GTGACCGTTTGGGAGTTGATGA-3' (SEQ ID NO:20) and reverse primer 5'-GGCTGAGGGAGGCGT-TCTC-3' (SEQ ID NO:21), 104-bp amplicon; ErbB2 forward primer 5'-GGGAAGAATGGGGTCGTCAAA-3' (SEQ ID NO:22) and reverse primer 5'-CTCCTCCCTGGGGTGT-CAAGT-3' (SEQ ID NO:23), 82-bp amplicon; ErbB3 forward primer 5'-GTGGCACTCAGGGAGCATTTA-3' (SEQ ID NO:24) and reverse primer 5'-TCTGGGACTGGG-GAAAAGG-3' (SEQ ID NO:25), 106-bp amplicon; ErbB4 forward primer 5'-TGCCCTACAGAGCCCCAACTA-3' (SEQ ID NO:26) and reverse primer 5'-GCTTGCG-TAGGGTGCCATTAC-3' (SEQ ID NO:27), 105-bp amplicon; ERRα forward primer 5'-AAAGTGCTGGC-CCATTTCTAT-3' (SEQ ID NO:7) and reverse primer 5'-CCTTGCCTCAGTCCATCAT-3' (SEQ ID NO:8), 100-bp amplicon; ERRβ forward primer 5'-TGCCCTACGACGA-CAA-3' (SEQ ID NO:28) and reverse primer 5'-ACTCCTC-CTTCTCCACCTT-3' (SEQ ID NO:29), 144-bp amplicon; and ERRγ forward primer 5'-GGCCATCAGAACG-GACTTG-3' (SEQ ID NO:30) and reverse primer 5'-GC-CCACTACCTCCCAGGATA-3' (SEQ ID NO:31), 67-bp amplicon. PCR primer sequences were designed using Oligo 5.0 software (National Biosciences; Plymouth, Minn.) and synthesized at the University of Wisconsin-Biotechnology Center (Madison, Wis.).

Serial dilution standard curves of each specific PCR product were included in every experiment and allowed calculation of transcript copy numbers in the unknown samples by regression analysis. The PCR product standards were in the form of ssDNA to better emulate cDNA in the unknown samples. The ssDNA standards were produced by linear amplification, using only the reverse primer (corresponding to the non-coding DNA strand), instead of by exponential amplification with two primers. The amount of each template required for the standard curves was determined in a similar manner as described above by trace radiolabeling with [$\alpha$-$^{32}$P]dCTP incorporation during the PCR amplification process. The mass of PCR product synthesized was converted to copy numbers according to the molecular weight of the specific amplicon's size in base pairs. All standard curves covered eight orders-of-magnitude and were assayed in triplicate.

Q-PCR assays were carried out in a total volume of 20 µl with 10 µl of 0.1 ng/µl cDNA. SYBR Green I (Molecular Probes; Eugene, Oreg.) was diluted in anhydrous DMSO at 1:2,500, then added to the enzyme reaction buffer to obtain a final concentration of 1:50,000 SYBR green I and 5% DMSO. To normalize fluorescence intensity between samples, the enzyme reaction buffer contained 180 nM passive reference dye ROX (Molecular Probes). The final concentrations of the remaining constituents were as follows: 10 mM Tris-HCl (pH 8.3), 50 mM KCl, 2.5 mM $MgCl_2$, 50 µM each dNTP, 500 nM each forward and reverse primer, and 0.025 units per µl HotStar Taq DNA polymerase (Qiagen). The thermal cycling parameters were 1 cycle of 95° C. for 10 min, and 40 cycles of 96° C. denaturation for 15 s followed by 60° C. annealing/extension for 1 min. Q-PCR assays were carried out with an ABI 7700 sequence detection system (Applied Biosystems, Foster City, Calif.).

ER and PgR by Ligand-binding Assays: ER and PgR content of the breast tumors were previously determined in a central laboratory. The standard multipoint, dextran-coated charcoal assay was modified as previously described (64) to incorporate $^{125}$I-labeled estradiol and $^3$H-labeled R5020 in a single assay, allowing the simultaneous determination of both ER and PgR. ER-LB levels greater than or equal to 3 fmol/mg protein were considered positive, and PgR-LB levels greater than or equal to 5 fmol/mg protein were considered positive.

DNA Ploidy and S-phase Fraction by Flow Cytometry: Flow cytometry was performed as previously described to determine DNA ploidy and S-phase fraction (64, 65). S-phase fractions were estimated using the MODFIT program (Verity House Software, Inc., Topsham, Me.). S-phase fractions less than 6% were considered low; S-phase fractions greater than 10% were considered high; and values between 6 and 10% were considered intermediate.

Figure 21:
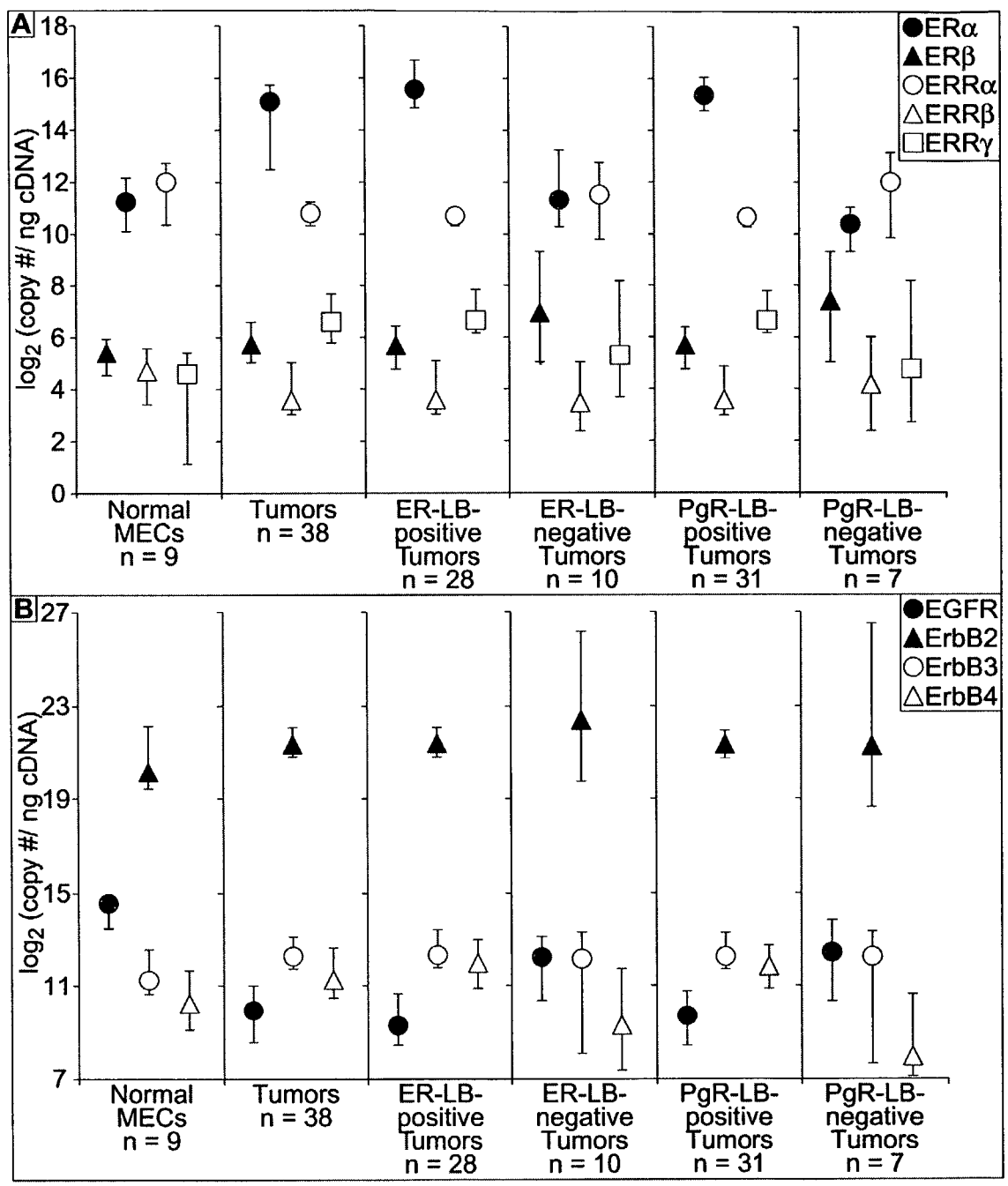
FIG. 21 shows gene expression distributions of ER and ERR family members (A) and ErbB family members (B). Expression levels are depicted as the 95% confidence intervals of the medians of log$_2$-transformed values.
Figure 22:
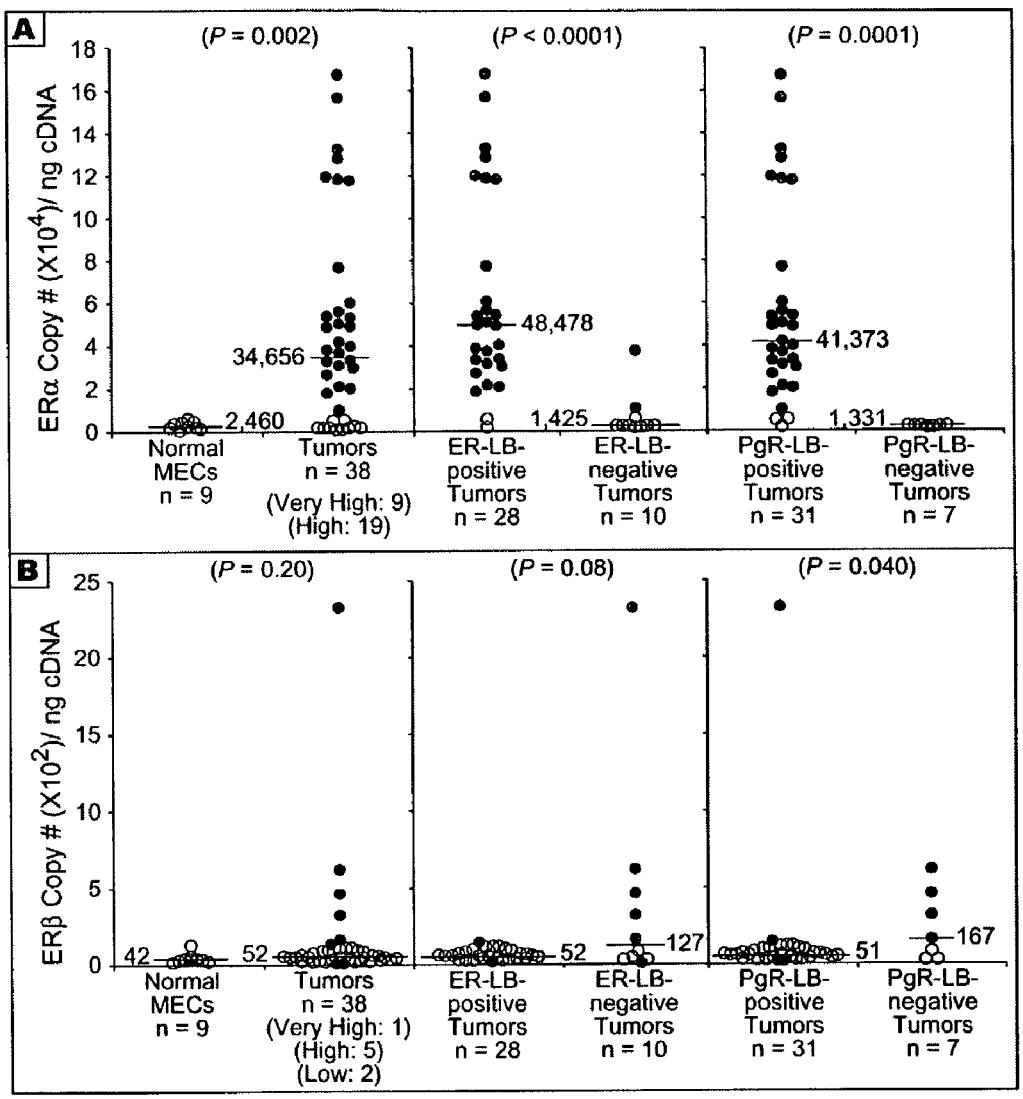
FIG. 22 shows ER family member mRNA levels (A for ERα levels and B for ERβ levels) in normal MECs, breast tumors, and tumors segregated by ER-LB and PgR-LB status. Horizontal bars represent the median values. Solid symbols indicate tumors expressing mRNAs at very high (10-fold above), high (above) and low (below) levels relative to the range of expression observed in normal MECs. Statistical significance was determined by the non-parametric Kruskal-Wallis ANOVA.
Figure 23:
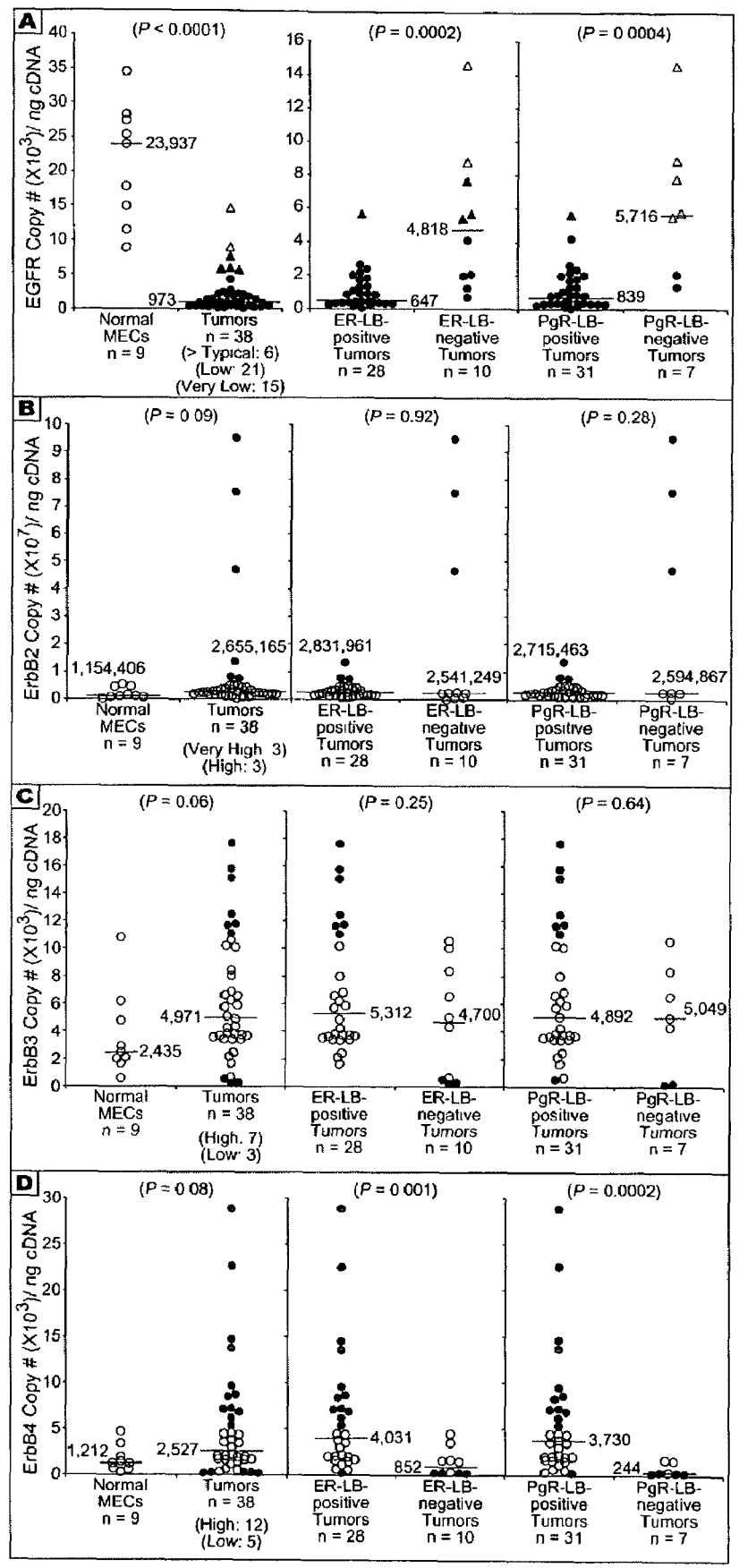
FIG. 23 shows ErbB family member mRNA levels (A for EGFR levels, B for ErbB2 levels, C for ErbB3 levels and D for ErbB4 levels) in normal MECs, breast tumors, and tumors segregated by ligand-binding ER and PgR (ER-LB and PgR-LB) status. Horizontal bars represent the median values. Solid symbols indicate tumors expressing mRNAs at very high (10-fold above), high (above), low (below) and very low (10-fold below) levels relative to the range of expression observed in normal MECs. Triangles indicate tumors expressing atypical mRNA levels relative to the standard deviation surrounding the mean expression level in the tumor group. Statistical significance was determined by the non-parametric Kruskal-Wallis ANOVA.
Figure 24:
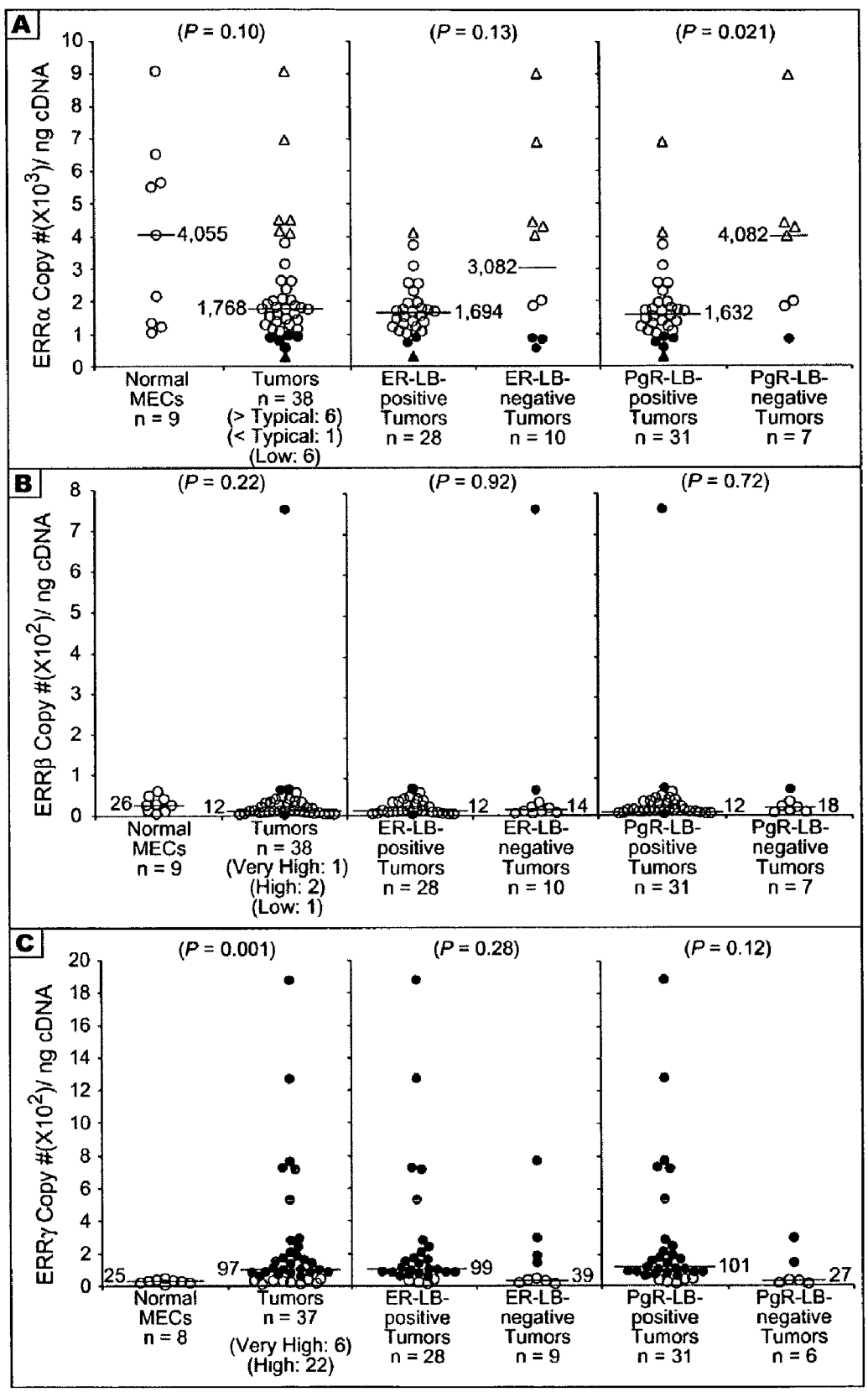
FIG. 24 shows ERR family member mRNA levels (A for ERRα levels, B for ERRβ levels and C for ERRγ levels) in normal MECs, breast tumors, and tumors segregated by ER-LB and PgR-LB status. Horizontal bars represent the median values. Solid symbols indicate tumors expressing mRNAs at very high (10-fold above), high (above), and low (below) levels relative to the range of expression observed in normal MECs. Triangles indicate tumors expressing atypical mRNA levels relative to the standard deviation surrounding the mean expression level in the tumor group. Statistical significance was determined by the non-parametric Kruskal-Wallis ANOVA.
Figure 25:
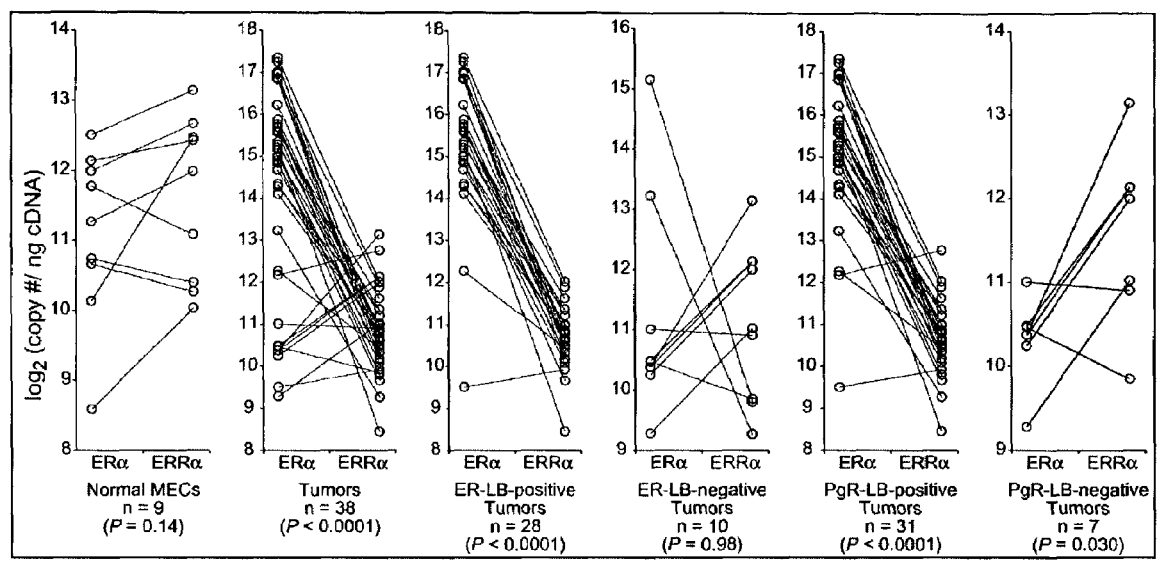
FIG. 25 shows ERα and ERRα mRNA levels within the same tissue sample. Significance was assessed by 1-way ANOVA with repeated measures on log$_2$-transformed values.

Statistics: Differences in abundance among separate mRNA species grouped by biological function were evaluated as independent variables using the 95% confidence intervals of the medians of $\log_2$-transformed values (FIG. 21). Changes in the abundance of a single mRNA species between tissue groups were tested by the non-parametric Kruskal-Wallis ANOVA (FIG. 22, FIG. 23, and FIG. 24). Associations between aberrant mRNA levels and clinicopathological biomarkers in the breast tumors were evaluated by Fisher's exact tests (Table 1). To analyze aberrant tumor expression relative to MECs, high and low expression in the breast tumors was defined as mRNA levels above or below, respectively, the range of expression in the normal MECs. Similarly, very high and very low expression in the tumors was defined as 10-fold above or below, respectively, the range of expression in normal MECs. Additionally, to analyze aberrant tumor expression relative to only other tumors and not MECs in the cases of EGFR and ERR$\alpha$, typical expression was defined as being within a standard deviation and aberrant expression as greater than a standard deviation away from the mean tumor level. Differences in expression between ER$\alpha$ and ERR$\alpha$ mRNA levels within the same tissue sample were assessed by 1-way ANOVA with repeated measures on $\log_2$-transformed data (FIG. 25). To discern whether ER$\alpha$ and ERR$\alpha$ were expressed at approximately equivalent levels within tumors, the ratio of their levels was stratified according to those found in normal MECs; ratios within a standard deviation of the average ratio in normal MECs were defined as equivalent. Pairwise relationships among gene expression levels and clinicopathologic factors were tested by the non-parametric rank correlation method, Spearman's rho analysis (Table 2). Spearman rank correlations involving ER-LB assays, PgR-LB assays, S-phase fraction and DNA ploidy used raw values on continuous scales instead of simple status assessments. All of the analyses described above were performed using SAS version 8.2 from SAS Institute, Inc. (Cary, N.C.).

Gene expression profiles were clustered or organized according to their similarity using the software Cluster and TreeView (written by Michael Eisen, copyrighted by Stanford University 1998-99; (66)). To cluster the profiles, the raw data were first adjusted by $\log_2$ transformation, centered upon the median value, and pre-ordered according to the self-organizing map algorithm incorporated within the software. Cluster analysis was performed by agglomerative hierarchical processing with complete linkage between items using Spearman's rank correlation as the similarity metric. The ordered data table was graphically depicted by colored cells representing gene expression levels: genes whose levels matched median normal MEC levels are colored black (log ratios of 0); genes with elevated expression (increasingly positive log ratios) are colored in increasing intensities of red; genes with decreased expression (increasingly negative log ratios) are colored in increasing intensities of green; and missing values are colored gray.

Results and Discussion

ER$\alpha$ mRNA Levels: ER$\alpha$ exhibited significantly higher mRNA levels than the other evaluated nuclear receptors in 76% (29 of 38) of the tumors, with the median ER$\alpha$ mRNA level approximately 20-fold greater than the next most abundant nuclear receptor (ERR$\alpha$) in steroid receptor-positive tumors (FIG. 21A and FIG. 25). This result exemplifies the critical role ER$\alpha$ plays in the majority of breast cancers. The median ER$\alpha$ mRNA level was 14-fold higher in breast carcinomas compared to normal MECs (Kruskal-Wallis ANOVA, P=0.002; FIG. 22A) and expressed at high or very high levels in 74% (28 of 38) of the breast tumors (FIG. 22A). The median ER$\alpha$ mRNA level was 34-fold greater in ER-LB-positive and 31-fold greater in PgR-LB-positive tumors relative to negative tumors (Kruskal-Wallis ANOVA, P<0.0001 and P=0.0001, respectively; FIG. 22A). Tumors that overexpressed ER$\alpha$ mRNA segregated with ER-LB and PgR-LB-positive status (Fisher's exact, P<0.0001 and P<0.0001, respectively; Table 1). Further, ER$\alpha$ mRNA levels strongly correlated with ER-LB ($\rho_s$=0.86, P<0.0001; Table 2) and PgR-LB protein levels ($\rho_s$=0.68, P<0.0001; Table 2) in the tumors as evaluated using the raw ligand-binding values over a continuous scale. These expected relationships validated the real-time Q-PCR assays and conform well with established findings of others regarding both typical percentage of ER-LB-positive tumors and elevated levels of ER$\alpha$ in these tumors (67).

TABLE 1

Fisher's exact tests for association between aberrant gene expression and clinicopathological features

| MRNA Levels | ER-LB Pos | ER-LB Neg | ER-LB P val | PgR-LB Pos | PgR-LB Neg | PgR-LB P val | S-phase Fraction Low | S-phase Fraction Int | S-phase Fraction High | S-phase Fraction P val | DNA Ploidy Di | DNA Ploidy Aneu | DNA Ploidy P val |
|---|---|---|---|---|---|---|---|---|---|---|---|---|---|
| ERα | | | | | | | | | | | | | |
| Normal | 2 | 8 | | 3 | 7 | | 5 | 1 | 4 | | 6 | 4 | |
| High | 17 | 2 | | 19 | 0 | | 11 | 3 | 4 | | 10 | 9 | |
| Very High | 9 | 0 | <0.0001 | 9 | 0 | <0.0001 | 5 | 1 | 3 | 0.88 | 4 | 5 | 0.91 |
| ERβ | | | | | | | | | | | | | |
| Low | 1 | 1 | | 2 | 0 | | 1 | 0 | 0 | | 2 | 0 | |
| Normal | 26 | 4 | | 27 | 3 | | 18 | 4 | 8 | | 15 | 15 | |
| High | 1 | 4 | | 1 | 4 | | 1 | 1 | 3 | | 2 | 3 | |
| Very High | 0 | 1 | 0.002 | 1 | 0 | 0.005 | 1 | 0 | 0 | 0.53 | 1 | 0 | 0.66 |
| EGFR* | | | | | | | | | | | | | |
| Typical | 27 | 5 | | 30 | 2 | | 18 | 5 | 9 | | 16 | 16 | |
| >Typical | 1 | 5 | 0.003 | 1 | 5 | 0.0002 | 3 | 0 | 2 | 1.00 | 4 | 2 | 0.66 |
| EGFR | | | | | | | | | | | | | |
| Very Low | 14 | 1 | | 15 | 0 | | 8 | 1 | 6 | | 7 | 8 | |
| Low | 14 | 7 | | 16 | 5 | | 12 | 4 | 4 | | 12 | 9 | |
| Normal | 0 | 2 | 0.012 | 0 | 2 | 0.003 | 1 | 0 | 1 | 0.51 | 1 | 1 | 0.86 |
| ErbB2 | | | | | | | | | | | | | |
| Normal | 25 | 7 | | 28 | 4 | | 18 | 4 | 9 | | 18 | 14 | |
| High | 3 | 1 | | 3 | 1 | | 3 | 0 | 1 | | 1 | 3 | |
| Very High | 0 | 2 | 0.11 | 0 | 2 | 0.029 | 0 | 1 | 1 | 0.35 | 1 | 1 | 0.65 |
| ErbB3 | | | | | | | | | | | | | |
| Low | 0 | 3 | | 1 | 2 | | 3 | 0 | 0 | | 3 | 0 | |
| Normal | 21 | 7 | | 23 | 5 | | 16 | 2 | 9 | | 15 | 13 | |
| High | 7 | 0 | 0.005 | 7 | 0 | 0.060 | 2 | 3 | 2 | 0.10 | 2 | 5 | 0.19 |
| ErbB4 | | | | | | | | | | | | | |
| Low | 1 | 4 | | 1 | 4 | | 2 | 1 | 2 | | 3 | 2 | |
| Normal | 15 | 6 | | 18 | 3 | | 12 | 2 | 6 | | 11 | 10 | |
| High | 12 | 0 | 0.002 | 12 | 0 | 0.002 | 7 | 2 | 3 | 0.86 | 6 | 6 | 1.00 |
| ERRα* | | | | | | | | | | | | | |
| <Typical | 1 | 0 | | 1 | 0 | | 1 | 0 | 1 | | 1 | 0 | |
| Typical | 26 | 5 | | 28 | 3 | | 18 | 4 | 7 | | 16 | 15 | |
| >Typical | 1 | 5 | 0.003 | 2 | 4 | 0.006 | 2 | 1 | 3 | 0.54 | 3 | 3 | 1.00 |
| ERRα | | | | | | | | | | | | | |
| Low | 3 | 3 | | 5 | 1 | | 4 | 0 | 1 | | 5 | 1 | |
| Normal | 25 | 7 | 0.31 | 26 | 6 | 1.00 | 17 | 5 | 10 | 0.66 | 15 | 17 | 0.18 |
| ERRβ | | | | | | | | | | | | | |
| Low | 5 | 0 | | 5 | 0 | | 1 | 1 | 2 | | 1 | 4 | |
| Normal | 22 | 8 | | 24 | 6 | | 18 | 4 | 7 | | 18 | 12 | |
| High | 1 | 1 | | 1 | 1 | | 1 | 0 | 1 | | 0 | 2 | |
| Very High | 0 | 1 | 0.12 | 1 | 0 | 0.38 | 1 | 0 | 0 | 0.61 | 1 | 0 | 0.069 |
| ERRγ | | | | | | | | | | | | | |
| Normal | 4 | 5 | | 5 | 4 | | 3 | 2 | 3 | | 4 | 5 | |
| High | 19 | 3 | | 20 | 2 | | 12 | 3 | 7 | | 10 | 12 | |
| Very High | 5 | 1 | 0.054 | 6 | 0 | 0.045 | 6 | 0 | 0 | 0.21 | 6 | 0 | 0.042 |

Pos (positive), Neg (negative), P val (P value), Int (intermediate), Di (diploid), Aneu (aneuploid)
*(expression levels relative to other tumors, not MECs)*

TABLE 2

Spearman's rank correlcation coefficients ($\rho_s$) for pairwise comparison in breast tumors and normal MECs

| | Breast Tumors | | | | | | | | | | | |
|---|---|---|---|---|---|---|---|---|---|---|---|---|
| | PgR-LB | S-phase | Ploidy | ERα | ERβ | EGFR | ErbB2 | ErbB3 | ErbB4 | ERRα | ERRβ | ERRγ |
| ER-LB | 0.74* | −0.07 | 0.09 | 0.86* | −0.11 | −0.76* | −0.01 | 0.17 | 0.53* | −0.23 | 0.11 | 0.19 |
| | <0.0001 | 0.68 | 0.59 | <0.0001 | 0.51 | <0.0001 | 0.97 | 0.3 | 0.001 | 0.16 | 0.51 | 0.27 |
| | 39 | 38 | 39 | 38 | 38 | 38 | 38 | 38 | 38 | 38 | 38 | 37 |

TABLE 2-continued

Spearman's rank correlation coefficients ($\rho_s$) for pairwise comparison in breast tumors and normal MECs Breast Tumors

| | PgR-LB | S-phase | Ploidy | ERα | ERβ | EGFR | ErbB2 | ErbB3 | ErbB4 | ERRα | ERRβ | ERRγ |
|---|---|---|---|---|---|---|---|---|---|---|---|---|
| PgR-LB | | −0.13 | 0.07 | 0.68* | −0.22 | −0.63* | 0.05 | 0.22 | 0.44* | −0.15 | 0.12 | 0.08 |
| | | 0.43 | 0.68 | <0.0001 | 0.18 | <0.0001 | 0.76 | 0.19 | 0.006 | 0.39 | 0.47 | 0.63 |
| | | 38 | 39 | 38 | 38 | 38 | 38 | 38 | 38 | 38 | 38 | 37 |
| S-phase | | | 0.75* | −0.13 | 0.01 | −0.09 | 0.08 | 0.35* | −0.18 | 0.19 | −0.37* | −0.31 |
| | | | <0.0001 | 0.43 | 0.95 | 0.6 | 0.63 | 0.034 | 0.29 | 0.26 | 0.026 | 0.07 |
| | | | 39 | 37 | 37 | 37 | 37 | 37 | 37 | 37 | 37 | 36 |
| Ploidy | | | | 0.06 | 0.05 | −0.24 | 0.13 | 0.19 | −0.04 | 0.19 | −0.19 | −0.27 |
| | | | | 0.71 | 0.77 | 0.15 | 0.45 | 0.25 | 0.82 | 0.25 | 0.26 | 0.11 |
| | | | | 38 | 38 | 38 | 38 | 38 | 38 | 38 | 38 | 37 |
| ERα | | | | | −0.15 | −0.54 | 0.17 | 0.42* | 0.74* | −0.13 | 0.07 | 0.2 |
| | | | | | 0.39 | 0.001 | 0.31 | 0.009 | <0.0001 | 0.44 | 0.66 | 0.24 |
| | | | | | 38 | 38 | 38 | 38 | 38 | 38 | 38 | 37 |
| ERβ | 0.27 | | | | | 0.08 | 0.24 | −0.15 | −0.16 | 0.35* | 0.58* | −0.14 |
| | 0.49 | | | | | 0.64 | 0.14 | 0.36 | 0.34 | 0.032 | 0.0002 | 0.42 |
| | 9 | | | | | 38 | 38 | 38 | 38 | 38 | 38 | 37 |
| EGFR | 0.73* | 0.03 | | | | | 0.27 | 0.09 | −0.3 | 0.19 | −0.13 | −0.17 |
| | 0.025 | 0.93 | | | | | 0.19 | 0.57 | 0.07 | 0.25 | 0.44 | 0.31 |
| | 9 | 9 | | | | | 38 | 38 | 38 | 38 | 38 | 37 |
| ErbB2 | 0.82* | 0.25 | | | | 0.83* | | 0.54* | 0.04 | 0.45* | −0.1 | 0.1 |
| | 0.007 | 0.52 | | | | 0.002 | | 0.0004 | 0.8 | 0.005 | 0.54 | 0.55 |
| | 9 | 9 | | | | 9 | | 38 | 38 | 38 | 38 | 37 |
| ErbB3 | 0.52 | 0.15 | | | | 0.48 | 0.70* | | 0.42* | 0.33* | −0.28 | 0.11 |
| | 0.15 | 0.7 | | | | 0.19 | 0.036 | | 0.009 | 0.047 | 0.09 | 0.51 |
| | 9 | 9 | | | | 9 | 9 | | 38 | 38 | 38 | 37 |
| ErbB4 | 0.35 | 0.27 | −0.15 | 0.2 | | 0.6 | | | | −0.15 | −0.1 | 0.32* |
| | 0.36 | 0.49 | 0.7 | 0.61 | | 0.09 | | | | 0.36 | 0.56 | 0.052 |
| | 9 | 9 | 9 | 9 | | 9 | | | | 38 | 38 | 37 |
| ERRα | 0.70* | 0.33 | | 0.90* | 0.93* | 0.57 | 0.05 | | | | 0.3 | 0.02 |
| | 0.036 | 0.38 | | 0.0009 | 0.0002 | 0.11 | 0.9 | | | | 0.07 | 0.92 |
| | 9 | 9 | | 9 | 9 | 9 | 9 | | | | 38 | 37 |
| ERRβ | 0.23 | 0.27 | | 0.5 | 0.58 | 0.28 | 0 | | | 0.77* | | −0.08 |
| | 0.55 | 0.49 | | 0.17 | 0.1 | 0.46 | 1 | | | 0.016 | | 0.62 |
| | 9 | 9 | | 9 | 9 | 9 | 9 | | | 9 | | 37 |
| ERRγ | 0.48 | 0.33 | | 0.14 | 0.64 | 0.81* | 0.76* | | | 0.38 | 0.17 | |
| | 0.23 | 0.42 | | 0.74 | 0.09 | 0.015 | 0.028 | | | 0.35 | 0.69 | |
| | 8 | 8 | | 8 | 8 | 8 | 8 | | | 8 | 8 | |

Normal MECs

*Spearman coefficient significance at P ≤ 0.05 (bolded)
Top ($\rho_s$), middle (P value), bottom (sample size)

ERβ mRNA Levels: The median ERβ mRNA level in the breast tumors was not significantly elevated compared to that in the normal MECs (FIG. 22B). ERβ mRNA levels were high or very high in 16% (6 of 38) of tumors and low in 5% (2 of 38) of tumors (FIG. 22B). The median level of ERβ mRNA expression was approximately 3.2-fold higher in PgR-LB-negative tumors compared to positive tumors (Kruskal-Wallis ANOVA, P=0.040; FIG. 22B). Dotzlaw et al. (68) have also reported increased ERβ expression in PgR-negative tumors. Also, tumors that overexpressed ERβ associated with ER-LB-negative and PgR-LB-negative status (Fisher's exact, P=0.002 and P=0.005, respectively; Table 1). Thus, increased ERβ levels inversely related with functional ERα status, and may therefore have reflected improper estrogen responsiveness.

ERα and ERβ are capable of forming functional heterodimers (69, 70). Because ERβ mRNA was present at much lower levels than ERα (FIG. 21A) as previously reported (71), ERα-ERβ heterodimers likely formed in addition to ERα homodimers in ER-LB/PgR-LB-positive tumors, whereas a greater proportion of ERβ homodimers likely formed in ER-LB/PgR-LB-negative tumors where ERα levels are relatively increased. Since ERα and ERβ display opposing transcriptional activities at AP-1 sites (72), it is reasonable to hypothesize that the transcriptional activities of ERα-ERβ heterodimers and ERβ-ERβ homodimers at AP-1 sites would also differ. Thus, ERα would have opposing modes of action dependent upon coexpression of ERα and may explain the result of Jensen et al.(7) that ERα-negative/ERβ-positive breast tumors contained significantly more proliferation markers than ERα-positive/ERβ-positive tumors. Hence, it has been put forth that ERα-negative/ERβ-positive tumor cells represent a potential population insensitive to the antiproliferative effects of antiestrogens (7). In support of this possibility, increased ERβ levels have been reported to be increased in tamoxifen-resistant versus sensitive breast tumors (73).

EGFR mRNA Levels: EGFR mRNA was the second most abundant transmembrane receptor mRNA species following ErbB2 in the normal MECs (FIG. 21B), consistent with EGFR acting as a dominant heterodimerization partner with ErbB2 in this tissue type (74). The median EGFR mRNA level was approximately $\frac{1}{25}^{th}$ in breast tumors relative to normal MECs (Kruskal-Wallis ANOVA, P<0.0001; FIG. 23A), with 55% (21 of 38) of tumors showing low and 39% (15 of 38) showing very low expression (solid symbols, FIG. 23A). However, when compared within the tumors as a class, 16% (6 of 38) showed elevated or greater than typical levels of EGFR expression (triangles, FIG. 23A) in agreement with other reports (reviewed in (13)). EGFR exhibited strongly significant inverse relationships with ERα expression in breast tumors. The median EGFR mRNA level was approximately 7.4-fold higher in ER-LB-negative and 6.8-fold higher in PgR-LB-negative versus positive tumors (Kruskal-Wallis ANOVA, P=0.0002 and P=0.0004, respectively; FIG. 23A). Also, tumors exhibiting greater than typical EGFR levels associated with ER-LB-negative and PgR-LB-negative status (Fisher's exact, P=0.003 and P=0.0002, respectively; Table 1). Further, EGFR mRNA levels inversely correlated with ERα mRNA levels ($\rho_s$32 –0.54, P=0.001; Table 2) as well as with ER-LB protein ($\rho_s$=–0.76, P<0.0001; Table 2) and PgR-LB protein amounts ($\rho_s$=–0.63, P<0.0001; Table 2) over a continuous scale in tumors, while directly correlating with ERα mRNA levels in normal MECs ($\rho_s$=0.73, P=0.025; Table 2). These data indicate that EGFR and ERα were coregulated in the normal MECs, but, in accordance with previous reports [reviewed in (13)], were inversely regulated in the tumors.

The strongly significant inverse relationships observed between EGFR and ERα expression in breast tumors were likely indicative of a negative feedback regulatory loop previously demonstrated to exist (75, 76). This negative feedback loop may explain why EGFR levels in tumors were $\frac{1}{25}^{th}$ of the levels in normal MECs; the dramatically elevated ERα levels in the tumors could have led to EGFR down-regulation. Escape from ERα-mediated negative feedback regulation would result in the greater than typical levels of EGFR seen in a subset of the tumors. Increased EGFR expression could potentially promote estrogen-independent cellular proliferation, as has been demonstrated by forced EGFR overexpression in cell lines (77) and reports that have linked EGFR-positive status to hormonal therapy resistance (20, 78, 79).

ErbB2 mRNA Levels: ErbB2 was the dominant transmembrane receptor as it was observed at markedly higher levels than the other ErbB members in every tissue subgroup (FIG. 21B). This finding is consistent with ErbB2 acting as the dominant heterodimerization subunit (reviewed in (10, 11)) and highlights its importance in mammary tissues. The median ErbB2 level showed a non-statistically significant 2.3-fold increase in expression in the breast tumors compared to the normal MECs (FIG. 23B). However, in agreement with reports of others ((17), reviewed in (14)), ErbB2 expression was significantly increased in 16% (6 of 38) of tumors, with 11% displaying high and 5% displaying very high ErbB2 levels. The maximum level of ErbB2 expression was 18-fold higher in the tumors compared to the maximum level in the normal MECs. Overexpression of ErbB2 associated with PgR-LB-negative status (Fisher's exact, P=0.029; Table 1) and, thereby, inversely associated with ERα functionality in the tumors as has been previously demonstrated (reviewed in (14)). On the other hand, ErbB2 mRNA levels directly correlated with both ERα mRNA levels ($\rho_s$=0.82, P=0.007; Table 2) and EGFR mRNA levels ($\rho_s$=0.83, P=0.002; Table 2) in the normal MECs. Thus, ErbB2 and EGFR likely participated in similar functions along with ERα in the normal MECs, yet distinct functions from ERα in a subset of tumors.

ErbB3 MRNA Levels: The median ErbB3 mRNA level showed a non-significant 2.0-fold increase in breast tumors compared to normal MECs (FIG. 23C). High expression of ErbB3 was observed in 18% (7 of 38) of the tumors, whereas low ErbB3 expression was observed in 8% (3 of 38) of the tumors. ErbB3 overexpression associated with ER-LB-positive tumor status (Fisher's exact, P=0.005; Table 1). Further, ErbB3 levels correlated with ERα mRNA levels in the tumors ($\rho_s$=0.42, P=0.009; Table 2), indicating that ErbB3 may have participated in ERα-mediated activities in this tissue type. A similar relationship between ErbB3 and ERα has been previously described (34). ErbB3 expression also correlated with ErbB2 expression in tumors ($\rho_s$=0.54, P=0.0004; Table 2) and normal MECs ($\rho_s$=0.70, P=0.036; Table 2), consistent with a prior report (32) and suggesting that these ErbB members form heterodimers in both tissue types. Moreover, ErbB3 correlated with S-phase fraction ($\rho_s$=0.35, P=0.034; Table 2), an established clinical indicator of tumor aggressiveness. Hence, ErbB3 may have similar, yet distinct roles with both ErbB2 and ERα in tumor cell proliferation.

ErbB4 mRNA Levels: The median ErbB4 mRNA level was a non-significant 2.1-fold higher in the breast tumors compared to the normal MECs (FIG. 23D). However, ErbB4 mRNA was present at high levels in 32% (12 of 38) of tumors and at low levels in 13% (5 of 38) of them. Interestingly, ErbB4 mRNA levels were elevated 4.7-fold in the ER-LB-positive and 15-fold in the PgR-LB-positive tumors relative to the LB-negative tumors (Kruskal-Wallis ANOVA, P=0.001 and P=0.0002, respectively; FIG. 23D), and overexpression of ErbB4 associated with ER-LB-positive and PgR-LB-positive status (Fisher's exact, P=0.002 and P=0.002, respectively; Table 1). Furthermore, ErbB4 levels also correlated with ERα mRNA levels ($\rho_s$=0.74, P<0.0001; Table 2) as well as with ER-LB ($\rho_s$=0.53, P=0.001; Table 2) and PgR-LB protein levels ($\rho_s$=0.44, P=0.006; Table 2) over a continuous scale in tumors. Therefore, in accordance with a similar finding of Knowlden et al. (34), ErbB4 shared a strong relationship with ERα functionality in tumors. Additionally, ErbB4 and ErbB3 correlated in tumors ($\rho_s$=0.42, P=0.009; Table 2), illustrating that ErbB4 and ErbB3 were coordinately overexpressed in steroid receptor-positive tumors. Hence, ErbB4 and ErbB3 likely shared some function, and jointly participated in activities with ERα in tumors The relationships observed here between ErbB4 and ERα were stronger and more extensive than between ErbB3 and ERα. For instance, ErbB4 mRNA levels significantly correlated with ER-LB and PgR-LB protein levels whereas ErbB3 did not (Table 2). Possibly, the relationship shared between ErbB3 and ERα indirectly occurred through ErbB4, via heterodimerization of ErbB3 with ErbB4 as indicated by a correlation between these latter genes (Table 2). Several possibilities exist that may explain the strong relationships observed between ErbB4 and ERα, including increased ErbB4 signaling leading to induction of ERα expression and increased ERα activity leading to induction of ErbB4 levels. Overexpressed ErbB4 shows good potential as a favorable biomarker because it associates with more differentiated histotypes (36), and it may oppose the negative effects of ErbB2 on clinical course (16, 35). Moreover, the finding that overexpressed ErbB4 strongly correlates with hormonally responsive indicators illustrates that ErbB4 may, itself, serve as a second biomarker of ERα functionality, in a similar manner as PgR, further improving selection of patients who may benefit from endocrine therapy.

ERRα mRNA Levels: The median ERRα mRNA level in the breast tumors was non-significantly 44% of the median level observed in normal MECs, though 16% (6 of 38) of tumors did contain significantly lower levels of ERRα (solid symbols, FIG. 24A). However, when ERRα levels were compared within the tumor group, ERRα levels were significantly greater than typical in 16% (6 of 38) of the samples, while only 3% (1 of 38) of the samples showed significantly lower than typical levels (triangles, FIG. 24A). Quite importantly, most of these ERRα-elevated tumors were also ER-LB-negative and PgR-LB-negative (Fisher's exact, P0.003 and P=0.006, respectively; Table 1), with the median ERRα mRNA level being significantly 2.5-fold higher in the PgR-LB-negative compared to PgR-LB-positive tumors (Kruskal- Wallis ANOVA, P=0.021, FIG. 24A). Thus, as with ERβ, EGFR and ErbB2, higher levels of ERRα occurred in the absence of functional ERα in the tumors. ERRα levels correlated with ERβ levels in tumors ($\rho_s$=0.35, P=0.032; Table 2), while they correlated with ERα levels in normal MECs ($\rho_s$=0.70, P=0.036; Table 2). ERRα also correlated with ErbB3 in tumors ($\rho_s$=0.33, P=0.047; Table 2), whereas it correlated with EGFR in normal MECs ($\rho_s$=0.90, P=0.0009; Table 2). Furthermore, ERRα displayed correlations with ErbB2 in both tumors ($\rho_s$=0.45, P=0.005; Table 2) and normal MECs ($\rho_s$=0.93, P=0.0002; Table 2). Hence, while ERRα may have functioned together with ErbB2 in both normal and tumor mammary cells, it may have also acted together with ERα and EGFR in normal MECs, and with ERβ and ErbB3 apart from ERα in tumors. These correlations could be indicative of irregular estrogen responsiveness in the pathogenesis of breast cancer.

As noted above, ERα was the dominant nuclear receptor in the majority of tumors. However, ERRα was the next most abundant transcription factor, showing greater levels of expression than ERβ, ERRβ and ERRγ in every tissue subgroup (FIG. 21A). Additionally, in normal MECs, ER-LB-negative tumors and PgR-LB-negative tumors, ERα and ERRα were expressed at similar levels when these variables were evaluated as independent variables (FIG. 21A), enabling ERRα to be a significant contributor to estrogen responsiveness or lack thereof. The distributions of ERα and ERRα expression were also compared within tissue samples as paired rather than independent variables by 1-way ANOVA with repeated measures (FIG. 25). Again, ERα and ERRα were expressed at similar levels in normal MECs (P=0.14) and ER-LB-negative tumors (P=0.98), while ERα was more abundant in the ER-LB-positive (P<0.0001) and PgR-LB-positive groups (P<0.0001). Most importantly, ERRα levels were significantly greater than ERα levels in PgR-LB-negative tumors (P=0.030) when examined as dependent variables. ERRα was present at greater levels than ERα in 13% (5 of 38), at approximately equivalent levels in 11% (4 of 38), and at lower levels in 76% (29 of 38) of tumors. Therefore, ERRα may have played a prominent or major role in ERE-dependent transcription in almost one-fourth of the breast tumors, while ERα may have played a greater physiological role in the remaining tumors.

ERRα's Potential Role in Breast Cancer: A primary conclusion from the above data is that ERRα showed a strong inverse relationship with ERα functionality in the tumors. Why might this be so? Without intending to be limited by theory, we hypothesize that ERRα functions in normal MECs as a modulator of the response to estrogen, competing with ERα for binding to EREs to achieve fine-tuned regulation of transcription. Misregulation can occur in tumors by several mechanisms. One common mechanism likely involves the overexpression of ERα, often accompanied by underexpression of ERRα relative to normal MECs, such that ERα outcompetes ERRα for binding to EREs. In this case, the modulatory effects of ERRα are largely lost. Alternatively, in ER-negative tumors or ones with high ERRα levels, ERRα becomes a major regulator of ERE-containing genes, acting constitutively since it functions independently of estrogen (37, 51).

Interestingly, ERRα has been shown to function actively as either as a repressor (43) or an activator (53, 59, 60) of transcription in mammary carcinoma cell lines in a cell type-dependent manner. The factors which determine ERRα's transcriptional activity have yet to be identified, but likely involve, in part, the ErbB2 signal transduction pathway. Here, we found ERRα mRNA abundance strongly correlated with ErbB2 abundance in both the breast tumors and normal MECs (Table 2), suggesting a functional relationship between these factors. Consistent with this correlation, ERRα has been shown to function as a transcriptional activator in SK-BR-3 mammary cells, cells in which the erbB2 locus has been amplified such that ErbB2 mRNA levels are 128-fold higher than in MCF-7 cells (80), while it functions as a transcriptional repressor in MCF-7 cells (43). ERRα has also been demonstrated to exist as a phosphoprotein in COS-7 cells, another cell line in which ERRα activates transcription (48). Moreover, we have recently found that ERRα can serve as a substrate for activated MAPK in vitro. Thus, ERRα and ErbB2 likely share a functional relationship through ErbB2-mediated modulation of ERRα's phosphorylation state. Combining these observations, we propose the following hypothesis: in cells containing low ErbB2 levels, ERRα down-modulates ERα-regulated ERE-dependent transcription; in cells containing high ErbB2 levels, ERRα constitutively activates transcription independent of ERα. A major prediction of this hypothesis is that tumors containing high levels of both ErbB2 and ERRα will not respond to antiestrogen therapy. This hypothesis also provides one of multiple mechanisms to explain ErbB2's relationship with tamoxifen resistance (18-23) and suggests that ERRα's phosphorylation status may have predictive value in assessing the effectiveness of therapeutic agents such as Herceptin which are directed against ErbB2. It also implicates ERRα itself as another likely efficacious target for therapy.

ERRβ mRNA Levels: ERRβ mRNA abundance was not significantly different between the tumors and the normal MECs, nor were ERRβ levels significantly different among the ER-LB and PgR-LB subgroups. ERRβ mRNA was increased in 8% (3 of 38) of tumors (FIG. 24B) and decreased in 3% (1 of 38) of tumors. Aberrant ERRβ expression was not associated with any of the clinical biomarkers, though too few tumors contained aberrant ERRβ amounts for strong statistical testing. Indicative of roles with other genes, ERRβ levels correlated with ERRα levels in normal MECs ($\rho_s$=0.77, P=0.016; Table 2), but with ERβ in tumors ($\rho_s$=0.58, P=0.0002; Table 2). The potential role of ERRβ in breast cancer may lie in its correlation with ERβ, which has been associated with indicators of both low and high tumor aggressiveness, (6, 7, 73). Curiously, ERRβ levels inversely correlated with S-phase fraction ($\rho_s$=−0.37, P=0.026; Table 2), perhaps suggesting that greater ERRβ levels inhibit cellular proliferation or, possibly, promote cellular differentiation. The importance for ERRβ in differentiation has been demonstrated by genetic ablation of this locus in mice, producing a severe defect in placental development that leads to embryonic lethality (81). Hence, whether ERRβ status predicts a favorable or unfavorable clinical course remains unclear. It should be noted that ERRβ mRNA levels were quite low (FIG. 20A and FIG. 24B), indicating the prognostic potential of ERRβ is not promising. However, ERβ mRNA levels were also quite low compared to ERα (FIG. 21A), yet allow accumulation of ERβ protein to levels clearly detectable by immunohistochemistry and participation in biologically significant roles in breast cancer (6, 7, 68, 73).

ERRγ mRNA Levels: The median ERRγ mRNA level was significantly elevated 3.9-fold in breast tumors relative to normal MECs (Kruskal-Wallis ANOVA, P=0.001; FIG. 24C). Moreover, ERRγ mRNA was overexpressed in approximately three-fourths of tumors, with high levels in 59% (22 of 37) and very high levels in an additional 16% (6 of 37) of tumors (FIG. 24C). These findings may indicate that ERRγ could be involved in the development of breast cancer. The median ERRγ mRNA level was not significantly different among the ER-LB or PgR-LB tumor subgroups. Nonetheless, tumors that overexpressed ERRγ were associated with ER-LB-positive and PgR-LB-positive status (Fisher's exact, P=0.054 and P=0.045, respectively; Table 1). Thus, tumors that overexpressed ERRγ were also frequently steroid receptor-positive, similar to tumors overexpressing ErbB3 or ErbB4. Hence, increased ERRγ levels may reflect hormonal sensitivity. ERRγ levels correlated with ErbB4 levels in both tumors ($\rho_s$=0.32, P=0.052; Table 2) and normal MECs ($\rho_s$=0.76, P=0.028; Table 2), as well as with ErbB3 levels in normal MECs ($\rho_s$=0.81, P=0.015; Table 2). As discussed above, ErbB4 overexpression likely indicates a preferable clinical outcome; likewise, ERRγ overexpression may also indicate a more positive outcome. Interestingly, the median ERRγ level was 2.0-fold higher in the less aggressive-in-nature diploid tumors (157 copies/ng cDNA) compared to the aneuploid tumors (79 copies/ng cDNA; Kruskal-Wallis ANOVA, P=0.033; data not shown), and the tumors that overexpressed ERRγ associated with diploid status (Fisher's exact, P=0.042; Table 1). Collectively, these findings indicate that ERRγ may serve as a marker of favorable clinical course. Further, in light of the studies that demonstrated ERRγ binds 4-hydroxytamoxifen as an antagonist (46, 52, 54), ERRγ-overexpressing tumors may help identify a subset of patients that would benefit from this treatment.

Clustered Expression Patterns: Cluster analysis provided a means to organize the observed pairwise relationships into higher ordered groups that likely reflected gene regulatory networks formed by extensive signaling cross-talk among the group's constituents. Expression patterns clustered into three groups in both the normal MECs and breast tumors. In the normal MECs, ERRα, EGFR, ErbB2, and ERα clustered, with ERRα and ErbB2 sharing the most significant relationship, followed by EGFR and then ERα; ERRβ and ERβ clustered; and ErbB4, ErbB3 and ERRγ clustered, with ErbB3 and ERRγ sharing the most significant relationship. In the breast tumors, ErbB2, ErbB3, ERRα, and EGFR clustered, with ErbB2 and ErbB3 sharing the most significant relationship, followed by ERRα and then EGFR; ERRβ and ERβ clustered; and ErbB4, ERα, and ERRγ clustered, with ErbB4 and ERα sharing the most significant relationship. Therefore, the cluster analysis indicated that ERα may have participated in a network with ErbB2, EGFR and ERRα in normal MECs, whereas it may have operated with ErbB4 and ERRγ in breast tumors.

The change in the genes that clustered with ERα may reflect altered signaling pathways necessary to support ERα-dependent tumor cell proliferation and, therefore, sensitivity to hormonal therapy. This may be illustrated by noting in the cluster analysis that the breast tumors generally segregated according to ERα status: those tumors with relatively high levels of ERα mRNA also frequently contained significant amounts of either ErbB4 or ERRγ or both factors. Importantly, the cluster analysis indicated the presence of two networks that lack ERα, yet which each may be capable of functionally substituting for some normally ERα-dependent activities; one cluster or network combines ERRα with EGFR, ErbB2, and ErbB3, while another cluster or network pairs ERRβ and ERβ. Thus, tumors with low levels of ERα mRNA tended to contain higher than typical levels of ERRα, EGFR, ErbB2 and/or ErbB3 or to contain overexpressed ERRβ and ERβ. Thus, these latter clusters may represent separate regulatory networks capable of supporting ERα-independent cellular proliferation and, consequently, insensitivity to hormonal therapy.

Conclusions

The results presented here show that the status of ERRα and ERRγ can indicate clinical outcomes and sensitivity to hormonal therapy. ERRα mRNA was found to be a major species (FIG. 21A), being expressed at levels greater than or similar to ERα in 24% of the tumors (FIG. 25). Tumors showing the highest levels of ERRα expression associated with a steroid receptor-negative status (Table 1, FIG. 24A) and, therefore, hormonal insensitivity. ERRα levels also directly correlated with levels of ErbB2 (Table 2), a marker of aggressive tumor behavior (reviewed in (14)). Thus, ERRα may be an important unfavorable marker in a significant proportion of breast cancer patients. Additionally, ERRα status may indicate the effectiveness of ErbB2-based therapeutics, with ERRα itself being a candidate therapeutic target, especially for ER/PgR-negative tumors. ERRγ was overexpressed in 75% of the tumors (FIG. 24C), indicating a role for this transcription factor in the pathogenesis of breast cancer. However, unlike ERRα, ERRγ overexpression associated with the presence of functional ERα (Table 1) and, hence, hormonal sensitivity. Further, ERRγ levels correlated with levels of ErbB4 (Table 2), a likely positive indicator of clinical outcome (16, 34-36), as well as with less aggressive diploid tumors (Table 1). Therefore, ERRγ shows potential as a favorable marker of clinical course. Moreover, since 4-hydroxytamoxifen has been found to antagonize ERRγ (46, 52, 54), selection of patients for treatment with this SERM may be improved by knowledge of ERRγ status.

References

1. Edwards, B. K., Howe, H. L., Ries, L. A., Thun, M. J., Rosenberg, H. M., Yancik, R., Wingo, P. A., Jemal, A., and Feigal, E. G. Annual report to the nation on the status of cancer, 1973 through 1999, featuring implications of age and aging on U.S. cancer burden. Cancer, 94: 2766-2792, 2002.
2. Nuclear Receptors Nomenclature Committee. A unified nomenclature system for the nuclear receptor superfamily [letter]. Cell, Vol. 97, pp. 161-163, 1999.
3. Sanchez, R., Nguyen, D., Rocha, W., White, J. H., and Mader, S. Diversity in the mechanisms of gene regulation by estrogen receptors. Bioessays, 24: 244-254., 2002.
4. Russo, J., Hu, Y. F., Yang, X., and Russo, I. H. Developmental, cellular, and molecular basis of human breast cancer [In Process Citation]. J Natl Cancer Inst Monogr, 27: 17-37, 2000.
5. Clark, G. M. and McGuire, W. L. Prognostic factors in primary breast cancer. Breast Cancer Res Treat, 3: S69-72, 1983.
6. Jarvinen, T. A., Pelto-Huikko, M., Holli, K., and Isola, J. Estrogen receptor beta is coexpressed with ERalpha and PR and associated with nodal status, grade, and proliferation rate in breast cancer. Am J Pathol, 156: 29-35, 2000.
7. Jensen, E. V., Cheng, G., Palmieri, C., Saji, S., Makela, S., Van Noorden, S., Wahlstrom, T., Warner, M., Coombes, R. C., and Gustafsson, J. A. Estrogen receptors and proliferation markers in primary and recurrent breast cancer. Proc Natl Acad Sci U S A, 98: 15197-15202., 2001.
8. Stern, D. F. Tyrosine kinase signalling in breast cancer: ErbB family receptor tyrosine kinases. Breast Cancer Res, 2: 176-183, 2000.
9. Olayioye, M. A. Update on HER-2 as a target for cancer therapy: Intracellular signaling pathways of ErbB2/HER-2 and family members. Breast Cancer Res, 3: 385-389, 2001.
10. Klapper, L. N., Glathe, S., Vaisman, N., Hynes, N. E., Andrews, G. C., Sela, M., and Yarden, Y. The ErbB-2/

HER2 oncoprotein of human carcinomas may function solely as a shared coreceptor for multiple stroma-derived growth factors. Proc Natl Acad Sci U S A, 96: 4995-5000., 1999.

11. Klapper, L. N., Kirschbaum, M. H., Sela, M., and Yarden, Y. Biochemical and clinical implications of the ErbB/HER signaling network of growth factor receptors. Adv Cancer Res, 77: 25-79, 2000.

12. Guy, P. M., Platko, J. V., Cantley, L. C., Cerione, R. A., and Carraway, K. L., 3rd Insect cell-expressed p180erbB3 possesses an impaired tyrosine kinase activity. Proc Natl Acad Sci U S A, 91: 8132-8136., 1994.

13. Klijn, J. G., Berns, P. M., Schmitz, P. I., and Foekens, J. A. The clinical significance of epidermal growth factor receptor (EGF-R) in human breast cancer: a review on 5232 patients. Endocr Rev, 13: 3-17, 1992.

14. Hynes, N. E. and Stern, D. F. The biology of erbB-2/neu/HER-2 and its role in cancer. Biochim Biophys Acta, 1198: 165-184., 1994.

15. Torregrosa, D., Bolufer, P., Lluch, A., Lopez, J. A., Barragan, E., Ruiz, A., Guillem, V., Munarriz, B., and Garcia Conde, J. Prognostic significance of c-erbB-2/neu amplification and epidermal growth factor receptor (EGFR) in primary breast cancer and their relation to estradiol receptor (ER) status. Clin Chim Acta, 262: 99-119., 1997.

16. Suo, Z., Risberg, B., Kalsson, M. G., Willman, K., Tierens, A., Skovlund, E., and Nesland, J. M. EGFR family expression in breast carcinomas. c-erbB-2 and c-erbB-4 receptors have different effects on survival. J Pathol, 196: 17-25., 2002.

17. Slamon, D. J., Clark, G. M., Wong, S. G., Levin, W. J., Ullrich, A., and McGuire, W. L. Human breast cancer: correlation of relapse and survival with amplification of the HER-2/neu oncogene. Science, 235: 177-182., 1987.

18. Wright, C., Nicholson, S., Angus, B., Sainsbury, J. R., Farndon, J., Cairns, J., Harris, A. L., and Home, C. H. Relationship between c-erbB-2 protein product expression and response to endocrine therapy in advanced breast cancer. Br J Cancer, 65: 118-121, 1992.

19. Borg, A., Baldetorp, B., Ferno, M., Killander, D., Olsson, H., Ryden, S., and Sigurdsson, H. ERBB2 amplification is associated with tamoxifen resistance in steroid-receptor positive breast cancer. Cancer Lett, 81: 137-144, 1994.

20. Newby, J. C., Johnston, S. R., Smith, I. E., and Dowsett, M. Expression of epidermal growth factor receptor and c-erbB2 during the development of tamoxifen resistance in human breast cancer. Clin Cancer Res, 3: 1643-1651, 1997.

21. Houston, S. J., Plunkett, T. A., Barnes, D. M., Smith, P., Rubens, R. D., and Miles, D. W. Overexpression of c-erbB2 is an independent marker of resistance to endocrine therapy in advanced breast cancer. Br J Cancer, 79: 1220-1226, 1999.

22. Dowsett, M., Harper-Wynne, C., Boeddinghaus, I., Salter, J., Hills, M., Dixon, M., Ebbs, S., Gui, G., Sacks, N., and Smith, I. HER-2 amplification impedes the antiproliferative effects of hormone therapy in estrogen receptor-positive primary breast cancer. Cancer Res, 61: 8452-8458., 2001.

23. Lipton, A., Ali, S. M., Leitzel, K., Demers, L., Chinchilli, V., Engle, L., Harvey, H. A., Brady, C., Nalin, C. M., Dugan, M., Carney, W., and Allard, J. Elevated serum Her-2/neu level predicts decreased response to hormone therapy in metastatic breast cancer. J Clin Oncol, 20: 1467-1472., 2002.

24. Elledge, R. M., Green, S., Ciocca, D., Pugh, R., Allred, D. C., Clark, G. M., Hill, J., Ravdin, P., O'Sullivan, J., Martino, S., and Osborne, C. K. HER-2 expression and response to tamoxifen in estrogen receptor-positive breast cancer: a Southwest Oncology Group Study. Clin Cancer Res, 4: 7-12, 1998.

25. Berry, D. A., Muss, H. B., Thor, A. D., Dressler, L., Liu, E. T., Broadwater, G., Budman, D. R., Henderson, I. C., Barcos, M., Hayes, D., and Norton, L. HER-2/neu and p53 expression versus tamoxifen resistance in estrogen receptor-positive, node-positive breast cancer. J Clin Oncol, 18: 3471-3479., 2000.

26. Sliwkowski, M. X., Lofgren, J. A., Lewis, G. D., Hotaling, T. E., Fendly, B. M., and Fox, J. A. Nonclinical studies addressing the mechanism of action of trastuzumab (Herceptin). Semin Oncol, 26: 60-70., 1999.

27. Vogel, C. L., Cobleigh, M. A., Tripathy, D., Gutheil, J. C., Harris, L. N., Fehrenbacher, L., Slamon, D. J., Murphy, M., Novotny, W. F., Burchmore, M., Shak, S., Stewart, S. J., and Press, M. Efficacy and safety of trastuzumab as a single agent in first-line treatment of HER2-overexpressing metastatic breast cancer. J Clin Oncol, 20: 719-726., 2002.

28. Slamon, D. J., Leyland-Jones, B., Shak, S., Fuchs, H., Paton, V., Bajamonde, A., Fleming, T., Eiermann, W., Wolter, J., Pegram, M., Baselga, J., and Norton, L. Use of chemotherapy plus a monoclonal antibody against HER2 for metastatic breast cancer that overexpresses HER2. N Engl J Med, 344: 783-792., 2001.

29. Esteva, F. J., Valero, V., Booser, D., Guerra, L. T., Murray, J. L., Pusztai, L., Cristofanilli, M., Arun, B., Esmaeli, B., Fritsche, H. A., Sneige, N., Smith, T. L., and Hortobagyi, G. N. Phase II study of weekly docetaxel and trastuzumab for patients with HER-2-overexpressing metastatic breast cancer. J Clin Oncol, 20: 1800-1808., 2002.

30. Moulder, S. L., Yakes, F. M., Muthuswamy, S. K., Bianco, R., Simpson, J. F., and Arteaga, C. L. Epidermal growth factor receptor (HER1) tyrosine kinase inhibitor ZD1839 (Iressa) inhibits HER2/neu (erbB2)-overexpressing breast cancer cells in vitro and in vivo. Cancer Res, 61: 8887-8895., 2001.

31. Normanno, N., Campiglio, M., De, L. A., Somenzi, G., Maiello, M., Ciardiello, F., Gianni, L., Salomon, D. S., and Menard, S. Cooperative inhibitory effect of ZD1839 (Iressa) in combination with trastuzumab (Herceptin) on human breast cancer cell growth. Ann Oncol, 13: 65-72., 2002.

32. Gasparini, G., Gullick, W. J., Maluta, S., Dalla Palma, P., Caffo, O., Leonardi, E., Boracchi, P., Pozza, F., Lemoine, N. R., and Bevilacqua, P. c-erbB-3 and c-erbB-2 protein expression in node-negative breast carcinoma—an immunocytochemical study. Eur J Cancer, 1: 16-22, 1994.

33. Lemoine, N. R., Barnes, D. M., Hollywood, D. P., Hughes, C. M., Smith, P., Dublin, E., Prigent, S. A., Gullick, W. J., and Hurst, H. C. Expression of the ERBB3 gene product in breast cancer. Br J Cancer, 66: 1116-1121., 1992.

34. Knowlden, J. M., Gee, J. M., Seery, L. T., Farrow, L., Gullick, W. J., Ellis, I. O., Blamey, R. W., Robertson, J. F., and Nicholson, R. I. c-erbB3 and c-erbB4 expression is a feature of the endocrine responsive phenotype in clinical breast cancer. Oncogene, 17: 1949-1957., 1998.

35. Bacus, S. S., Chin, D., Yarden, Y., Zelnick, C. R., and Stern, D. F. Type 1 receptor tyrosine kinases are differentially phosphorylated in mammary carcinoma and differentially associated with steroid receptors. Am J Pathol, 148: 549-558., 1996.

36. Kew, T. Y., Bell, J. A., Pinder, S. E., Denley, H., Srinivasan, R., Gullick, W. J., Nicholson, R. I., Blamey, R. W., and Ellis, I. O. c-erbB-4 protein expression in human breast cancer. Br J Cancer, 82: 1163-1170., 2000.
37. Giguère, V., Yang, N., Segui, P., and Evans, R. M. Identification of a new class of steroid hormone receptors. Nature, 331: 91-94, 1988.
38. Shi, H., Shigeta, H., Yang, N., Fu, K., O'Brian, G., and Teng, C. T. Human estrogen receptor-like 1 (ESRL1) gene: genomic organization, chromosomal localization, and promoter characterization. Genomics, 44: 52-60, 1997.
39. Johnston, S. D., Liu, X., Zuo, F., Eisenbraun, T. L., Wiley, S. R., Kraus, R. J., and Mertz, J. E. Estrogen-related receptor alpha 1 functionally binds as a monomer to extended half-site sequences including ones contained within estrogen-response elements. Mol Endocrinol, 11: 342-352, 1997.
40. Chen, F., Zhang, Q., McDonald, T., Davidoff, M. J., Bailey, W., Bai, C., Liu, Q., and Caskey, C. T. Identification of two hERR2-related novel nuclear receptors utilizing bioinformatics and inverse PCR. Gene, 228: 101-109, 1999.
41. Eudy, J. D., Yao, S., Weston, M. D., Ma-Edmonds, M., Talmadge, C. B., Cheng, J. J., Kimberling, W. J., and Sumegi, J. Isolation of a gene encoding a novel member of the nuclear receptor superfamily from the critical region of Usher syndrome type IIa at 1q41. Genomics, 50: 382-384, 1998.
42. Heard, D. J., Norby, P. L., Holloway, J., and Vissing, H. Human ERRgamma, a third member of the estrogen receptor-related receptor (ERR) subfamily of orphan nuclear receptors: tissue-specific isoforms are expressed during development and in the adult. Mol Endocrinol, 14: 382-392, 2000.
43. Kraus, R. J., Ariazi, E. A., Farrell, M. L., and Mertz, J. E. Estrogen-related receptor alpha 1 actively antagonizes estrogen receptor-regulated transcription in MCF-7 mammary cells. J Biol Chem, Paper In Press, published online ahead of print, 2002.
44. Vanacker, J. M., Pettersson, K., Gustafsson, J. A., and Laudet, V. Transcriptional targets shared by estrogen receptor-related receptors (ERRs) and estrogen receptor (ER) alpha, but not by ERbeta. EMBO J, 18: 4270-4279, 1999.
45. Hong, H., Yang, L., and Stallcup, M. R. Hormone-independent transcriptional activation and coactivator binding by novel orphan nuclear receptor ERR3. J Biol Chem, 274: 22618-22626, 1999.
46. Coward, P., Lee, D., Hull, M. V., and Lehmann, J. M. 4-Hydroxytamoxifen binds to and deactivates the estrogen-related receptor gamma. Proc Natl Acad Sci USA, 98: 8880-8884., 2001.
47. Bonnelye, E., Vanacker, J. M., Spruyt, N., Alric, S., Fournier, B., Desbiens, X., and Laudet, V. Expression of the estrogen-related receptor 1 (ERR-1) orphan receptor during mouse development. Mech Dev, 65: 71-85, 1997.
48. Sladek, R., Bader, J. A., and Giguere, V. The orphan nuclear receptor estrogen-related receptor alpha is a transcriptional regulator of the human medium-chain acyl coenzyme A dehydrogenase gene. Mol Cell Biol, 17: 5400-5409, 1997.
49. Vanacker, J. M., Bonnelye, E., Chopin-Delannoy, S., Delmarre, C., Cavailles, V., and Laudet, V. Transcriptional activities of the orphan nuclear receptor ERR alpha (estrogen receptor-related receptor-alpha). Mol Endocrinol, 13: 764-773, 1999.
50. Xie, W., Hong, H., Yang, N. N., Lin, R. J., Simon, C. M., Stallcup, M. R., and Evans, R. M. Constitutive activation of transcription and binding of coactivator by estrogen-related receptors 1 and 2. Mol Endocrinol, 13: 2151-2162, 1999.
51. Tremblay, G. B., Kunath, T., Bergeron, D., Lapointe, L., Champigny, C., Bader, J. A., Rossant, J., and Giguere, V. Diethylstilbestrol regulates trophoblast stem cell differentiation as a ligand of orphan nuclear receptor ERR beta. Genes Dev, 15: 833-838., 2001.
52. Greschik, H., Wurtz, J. M., Sanglier, S., Bourguet, W., van Dorsselaer, A., Moras, D., and Renaud, J. P. Structural and functional evidence for ligand-independent transcriptional activation by the estrogen-related receptor 3. Mol Cell, 9: 303-313., 2002.
53. Chen, S., Zhou, D., Yang, C., and Sherman, M. Molecular basis for the constitutive activity of estrogen related receptor a-1 (ERRa-1). J Biol Chem, 16: 16, 2001.
54. Tremblay, G. B., Bergeron, D., and Giguere, V. 4-Hydroxytamoxifen is an isoform-specific inhibitor of orphan estrogen-receptor-related (ERR) nuclear receptors beta and gamma. Endocrinology, 142: 4572-4575., 2001.
55. Lu, D., Kiriyama, Y., Lee, K. Y., and Giguere, V. Transcriptional regulation of the estrogen-inducible pS2 breast cancer marker gene by the ERR family of orphan nuclear receptors. Cancer Res, 61: 6755-6761., 2001.
56. Yang, N., Shigeta, H., Shi, H., and Teng, C. T. Estrogen-related receptor, hERR1, modulates estrogen receptor-mediated response of human lactoferrin gene promoter. J Biol Chem, 271: 5795-5804, 1996.
57. Bonnelye, E., Vanacker, J. M., Dittmar, T., Begue, A., Desbiens, X., Denhardt, D. T., Aubin, J. E., Laudet, V., and Fournier, B. The ERR-1 orphan receptor is a transcriptional activator expressed during bone development. Mol Endocrinol, 11: 905-916, 1997.
58. Vanacker, J. M., Delmarre, C., Guo, X., and Laudet, V. Activation of the osteopontin promoter by the orphan nuclear receptor estrogen receptor related alpha. Cell Growth Differ, 9: 1007-1014, 1998.
59. Yang, C., Zhou, D., and Chen, S. Modulation of aromatase expression in the breast tissue by ERR alpha-1 orphan receptor. Cancer Res, 58: 5695-5700, 1998.
60. Yang, C. and Chen, S. Two organochlorine pesticides, toxaphene and chlordane, are antagonists for estrogen-related receptor alpha-1 orphan receptor. Cancer Res, 59: 4519-4524, 1999.
61. Zhang, Z. and Teng, C. T. Estrogen receptor-related receptor alpha 1 interacts with coactivator and constitutively activates the estrogen response elements of the human lactoferrin gene. J Biol Chem, 275: 20837-20846., 2000.
62. Zhang, Z. and Teng, C. T. Estrogen receptor alpha and estrogen receptor-related receptor alpha1 compete for binding and coactivator. Mol Cell Endocrinol, 172: 223-233., 2001.
63. Bustin, S. A. Absolute quantification of mRNA using real-time reverse transcription polymerase chain reaction assays. J Mol Endocrinol, 25: 169-193, 2000.
64. Dressler, L. G., Seamer, L. C., Owens, M. A., Clark, G. M., and McGuire, W. L. DNA flow cytometry and prognostic factors in 1331 frozen breast cancer specimens. Cancer, 61: 420-427., 1988.
65. Wenger, C. R., Beardslee, S., Owens, M. A., Pounds, G., Oldaker, T., Vendely, P., Pandian, M. R., Harrington, D., Clark, G. M., and McGuire, W. L. DNA ploidy, S-phase, and steroid receptors in more than 127,000 breast cancer patients. Breast Cancer Res Treat, 28: 9-20, 1993.

66. Eisen, M. B., Spellman, P. T., Brown, P. O., and Botstein, D. Cluster analysis and display of genome-wide expression patterns. Proc Natl Acad Sci U S A, 95: 14863-14868, 1998.

67. Clark, G. M., McGuire, W. L., Hubay, C. A., Pearson, O. H., and Carter, A. C. The importance of estrogen and progesterone receptor in primary breast cancer. Prog Clin Biol Res 183-190, 1983.

68. Dotzlaw, H., Leygue, E., Watson, P. H., and Murphy, L. C. Estrogen receptor-beta messenger RNA expression in human breast tumor biopsies: relationship to steroid receptor status and regulation by progestins. Cancer Res, 59: 529-532, 1999.

69. Cowley, S. M., Hoare, S., Mosselman, S., and Parker, M. G. Estrogen receptors alpha and beta form heterodimers on DNA. J Biol Chem, 272: 19858-19862, 1997.

70. Tremblay, G. B., Tremblay, A., Labrie, F., and Giguere, V. Dominant activity of activation function 1 (AF-1) and differential stoichiometric requirements for AF-1 and -2 in the estrogen receptor alpha-beta heterodimeric complex. Mol Cell Biol, 19: 1919-1927, 1999.

71. Knowlden, J. M., Gee, J. M., Robertson, J. F., Ellis, I. O., and Nicholson, R. I. A possible divergent role for the oestrogen receptor alpha and beta subtypes in clinical breast cancer. Int J Cancer, 89: 209-212, 2000.

72. Paech, K., Webb, P., Kuiper, G. G., Nilsson, S., Gustafsson, J., Kushner, P. J., and Scanlan, T. S. Differential ligand activation of estrogen receptors ERalpha and ERbeta at AP1 sites [see comments]. Science, 277: 1508-1510, 1997.

73. Speirs, V., Malone, C., Walton, D. S., Kerin, M. J., and Atkin, S. L. Increased expression of estrogen receptor beta mRNA in tamoxifen-resistant breast cancer patients. Cancer Res, 59: 5421-5424., 1999.

74. Brandt, B. H., Roetger, A., Dittmar, T., Nikolai, G., Seeling, M., Merschjann, A., Nofer, J. R., Dehmer-Moller, G., Junker, R., Assmann, G., and Zaenker, K. S. c-erbB-2/EGFR as dominant heterodimerization partners determine a motogenic phenotype in human breast cancer cells. Faseb J, 13: 1939-1949., 1999.

75. Yarden, R. I., Lauber, A. H., El-Ashry, D., and Chrysogelos, S. A. Bimodal regulation of epidermal growth factor receptor by estrogen in breast cancer cells. Endocrinology, 137: 2739-2747, 1996.

76. Chrysogelos, S. A., Yarden, R. I., Lauber, A. H., and Murphy, J. M. Mechanisms of EGF receptor regulation in breast cancer cells. Breast Cancer Res Treat, 31: 227-236, 1994.

77. Miller, D. L., el-Ashry, D., Cheville, A. L., Liu, Y., McLeskey, S. W., and Kern, F. G. Emergence of MCF-7 cells overexpressing a transfected epidermal growth factor receptor (EGFR) under estrogen-depleted conditions: evidence for a role of EGFR in breast cancer growth and progression. Cell Growth Differ, 5: 1263-1274., 1994.

78. Nicholson, S., Wright, C., Sainsbury, J. R., Halcrow, P., Kelly, P., Angus, B., Farndon, J. R., and Harris, A. L. Epidermal growth factor receptor (EGFr) as a marker for poor prognosis in node-negative breast cancer patients: neu and tamoxifen failure. J Steroid Biochem Mol Biol, 37: 811-814, 1990.

79. Nicholson, S., Halcrow, P., Sainsbury, J. R., Angus, B., Chambers, P., Farndon, J. R., and Harris, A. L. Epidermal growth factor receptor (EGFr) status associated with failure of primary endocrine therapy in elderly postmenopausal patients with breast cancer. Br J Cancer, 58: 810-814., 1988.

80. Kraus, M. H., Popescu, N. C., Amsbaugh, S. C., and King, C. R. Overexpression of the EGF receptor-related proto-oncogene erbB-2 in human mammary tumor cell lines by different molecular mechanisms. Embo J, 6: 605-610, 1987.

81. Luo, J., Sladek, R., Bader, J. A., Matthyssen, A., Rossant, J., and Giguere, V. Placental abnormalities in mouse embryos lacking the orphan nuclear receptor ERR-beta. Nature, 388: 778-782, 1997.

EXAMPLE 4

Identification of ERRα-binding Sites in Human Promoters of Genes Implicated in Breast Cancer Knowing which genes are transcriptionally modulated by ERR may help to clarify ERR's potential role in breast cancer. To identify potential ERR-responsive genes, we examined the transcriptional regulatory regions of genes known to be involved in breast cancer for sequences capable of being bound by ERR. In Example 1, we showed that ERR binds with high affinity the consensus sequence 5'-TCAAGGTCA-3' (16), which is referred to here in Example 4 as an ERRE. This sequence is a half-site of the consensus palindromic estrogen response element (ERE, 5'-AGGTCAnnnTGACCT (SEQ ID NO:32)) with a 3-base pair extension at the 5' end. Searching sequence databases (the EPD Eukaryotic Promoter Database available on line from the Swiss Institute of Bioinformatics (17), and Genbank available on line from the National Center for Biotechnology Information, National Library of Medicine, National Institute of Health) facilitated the location of this consensus and similar non-consensus ERREs in human gene promoters, which were selected and tested experimentally for whether they contained authentic ERR-binding sites. Using quantitative competitive EMSAs performed similarly as described in FIG. 5 of Example 1, we identified many authentic ERR-binding sites that exist in the promoters of important genes implicated in breast cancer. These sequences and ERR's affinity for binding these sites relative to a reference consensus ERRE are shown in Table 3 (Location, distance of the ERRE sequence from the gene's transcriptional start site; Ref, reference of the gene's prognostic status or relevance to human breast cancer). Hence, the genes listed in Table 3 are potentially transcriptionally responsive to ERR.

Interestingly, ERRα-binding sites, identical in their core sequence but found in separate promoters, exhibited different relative binding affinities (RBAs). For example, identical ERREs of sequence 5'-TCAAGGTCA-3' present in PgR (site 3) and the reference ERRE manifested RBAs of 1.45 and 1.00, respectively. Similarly, identical ERREs of sequence 5'-CCAAGGTCA-3' found in ErbB2 and aromatase exhibited RBAs of 1.01 and 0.17, respectively. Thus, the site's context modulates ERRα's binding affinity. Importantly, relative to the reference consensus ERRE, naturally occurring ERREs identified in the PgR (site 3 with RBA=1.45; site 2 with RBA=0.91) and ErbB2 promoters (RBA=1.01) exhibited higher or similar affinities for binding ERRα, indicating a high probability that these genes are targets of ERRα. Significantly, several of the breast cancer gene promoters contain more than one ERRE, with 3 sites in PgR, 2 sites in pS2, 2 sites in IGF2 and 3 sites in prolactin. Multiple binding sites in a given promoter indicate a higher likelihood that ERRα regulates transcription of the gene. Using a cell line stably transfected with ERRα, Yang et al. (18) demonstrated that ERRα induced aromatase levels in vivo, an enzyme expressed in breast tissue that converts androgens to estrogens (12). Thus, ERREs with RBAs significantly lower than the reference ERRE (aromatase, RBA=0.17) are capable of mediating ERRα-dependent transcriptional regulation.

Notably, we have found that ERRα and ErbB2 mRNA expression levels directly correlate in human breast cancer as shown in Table 2 of Example 3, and here we show a high affinity ERRα binding site in the ErbB2 promoter. ErbB2 associates with ER-negative tumor status, indicates aggressive tumor behavior, and predicts poor prognosis [reviewed in (2)]. ErbB2 signals via the mitogen-activated protein kinase (MAPK) pathway [reviewed in (10, 19)], and many other genes listed in Table 3 are involved in ErbB2/MAPK signaling, including EGF, which is a ligand of EGF receptor-ErbB2 heterodimers [reviewed in (19)]; and elk1, which is a transcription factor that is activated via MAPK signaling (10, 20). Moreover, growth factors or their receptors listed in Table 3 including IGF2, IGF1R and prolactin, either signal directly or participate in cross-talk via the MAPK pathway [reviewed in (10, 20, 21)]. Hence, ERRα could potentially modulate expression of ErbB2 as well as expression of several members of its signaling pathway, and thereby share an important functional relationship with ErbB2. Thus, ERRα's potential to regulate transcription of multiple breast cancer biomarkers including PgR, ErbB2 and other important genes lends credence to ERRα's utility as a breast cancer biomarker.

TABLE 3

Relative binding affinities (RBA) of ERRα1 for DNA sequences found in transcriptional regulatory regions (promoters) of human genes implicated in breast cancer.^

| Gene | Ref | Location | Oligodeoxynucleotide Sequence | | RBA |
|---|---|---|---|---|---|
| PgR site 3 | (1) | -3.29 kb | TCCTAAGGACTGTCAAGGTCATCAAATACAAGG | (SEQ ID NO:33) | 1.45 |
| ErbB2 | (2) | -3.44 kb | AAAGGAACTTTCCCAAGGTCACAGAGCTGAGCT* | (SEQ ID NO:34) | 1.01 |
| Reference ERRE | NA | | TCGAGAGCAGTGGCGATTTGTCAAGGTCACACAGTGAG | (SEQ ID NO:35) | 1.00 |
| PgR site 2 | (1) | -5.17 kb | TCCTTGCTAAACCCAAGGTCATAAATCTTTTCT* | (SEQ ID NO:36) | 0.91 |
| ERβ | (3) | -559 bp | GGTGCTCCCACTTAGAGGTCACGCGCGGCGTCG | (SEQ ID NO:37) | 0.54 |
| pS2 site 1 | (4) | -407 bp | TCCCTTCCCCCTGCAAGGTCACGGTGGCCACCC | (SEQ ID NO:38) | 0.49 |
| Cathepsin D | (5) | -3.64 kb | TGGCATATTGGGTGAAGGTCAAGGGAGTGGCTT* | (SEQ ID NO:39) | 0.49 |
| IGF1R | (6) | +272 bp | GCTCCGGCTCGCTGAAGGTCACAGCCGAGGCGA* | (SEQ ID NO:40) | 0.36 |
| hMDM2 | (7) | +575 bp | GGGAGTTCAGGGTAAAGGTCACGGGGCCGGGGC | (SEQ ID NO:41) | 0.35 |
| Prl site 2 | (8) | -1.35 kb | CAAATTTGAAACTAAAGGTCACAGGCTGCTTTA | (SEQ ID NO:42) | 0.33 |
| IGF2 site 2 | (9) | -6.48 kb | CTGTCGGCAGGAACAAGGTCACCCCTTGGCGTT* | (SEQ ID NO:43) | 0.25 |
| elk1 | (10) | -2.19 kb | CTCCCATCTCACTTAAGGTCAAAGCCAGGGTCC | (SEQ ID NO:44) | 0.22 |
| BRCA1 | (11) | -293 bp | GTAATTGCTGTACGAAGGTCAGAATCGCTACCT* | (SEQ ID NO:45) | 0.17 |
| aromatase | (12) | -99 bp | CCTGAGACTCTACCAAGGTCAGAAATGCTGCAA | (SEQ ID NO:46) | 0.17 |
| PgR site 1 | (1) | -5.91 kb | AAAATTGTTTTGTCTAGGTCATTTGCATTTTCA* | (SEQ ID NO:47) | 0.14 |
| EGF | (13) | -396 bp | CAAATAATGGGCTGAAGGTGAACTATCTTTACT | (SEQ ID NO:48) | 0.14 |
| pS2 site 2 | (4) | -266 bp | GTAGGACCTGGATTAAGGTCAGGTTGGAGGAGA | (SEQ ID NO:49) | 0.12 |
| ERα | (1) | -865 bp | ATGTTTGGTATGAAAAGGTCACATTTTATATTC | (SEQ ID NO:50) | 0.11 |
| BRCA2 | (14) | -339 bp | AGAACATCCCTTTTAAGGTCAGAACAAAGGTAT | (SEQ ID NO:51) | 0.08 |
| Prl site 3 | (8) | -1.18 kb | CCTCAGAGTGGCTCAGGGTCAGAGAAGGTAGAG | (SEQ ID NO:52) | 0.07 |
| cyclin D1 | (15) | -2.56 kb | GCGAGGAAAGCGTGAAGGTGATTTCAGTTAATT | (SEQ ID NO:53) | 0.07 |

TABLE 3-continued

Relative binding affinities (RBA) of ERRα1 for DNA sequences found in transcriptional regulatory regions (promoters) of human genes implicated in breast cancer.^

| Gene | Ref | Location | Oligodeoxynucleotide Sequence | | RBA |
|---|---|---|---|---|---|
| IGF2 site 3 | (9) | −2.72 kb | GGTGGACGCTGCTGAAGGTGAGCGAGACCCCGG* | (SEQ ID NO:54) | 0.06 |
| Prl site 1 | (8) | −4.81 kb | TGTCCATTTTCTTCTAGGTCAACCCCAATGGTA | (SEQ ID NO:55) | 0.06 |

*Sequence found in reverse orientation in the natural promoter.
^Quantitative competition electrophoretic mobility shift assays (EMSAs) were carried out as described above for FIG. 5 in Example 1. Whole cell extracts of COS cells transfected with an ERRα1 expression plasmid were employed as a protein source. Unlabeled oligodeoxynucleotides (Table 3) corresponding to genes relevant to breast cancer were allowed to compete with the $^{32}$P-labeled reference consensus ERRE (estrogen-related receptor response element) oligodeoxynucleotide for binding to ERRα1. The RBAs were determined empirically as the reciprocal of the fold molar excess of unlabeled competitor oligodeoxynucleotide needed to reduce by 50% the amount of shifted reference labeled probe. PgR (progesterone receptor), ER (estrogen receptor), IGF1R (IGF-1 receptor), hMDM2 (human p53-binding protein MDM2 (murine double minute 2)), Prl (prolactin), IGF2 (insulin-like growth factor-2), BRCA (breast and ovarian cancer susceptibility gene), EGF (epidermal growth factor).

References

1. Clark, G. M. and McGuire, W. L. Prognostic factors in primary breast cancer. Breast Cancer Res Treat, 3: S69-72, 1983.
2. Hynes, N. E. and Stern, D. F. The biology of erbB-2/neu/HER-2 and its role in cancer. Biochim Biophys Acta, 1198: 165-184., 1994.
3. Jensen, E. V., Cheng, G., Palmieri, C., Saji, S., Makela, S., Van Noorden, S., Wahlstrom, T., Warner, M., Coombes, R. C., and Gustafsson, J. A. Estrogen receptors and proliferation markers in primary and recurrent breast cancer. Proc Natl Acad Sci U S A, 98: 15197-15202., 2001.
4. Crombach, G., Ingenhorst, A., Gohring, U. J., Scharl, A., Neuhaus, W., Mobus, V., and Schaeffer, H. J. Expression of pS2 protein in breast cancer. Arch Gynecol Obstet, 253: 183-192, 1993.
5. Rochefort, H. Cathepsin D in breast cancer. Breast Cancer Res Treat, 16: 3-13, 1990.
6. Papa, V., Gliozzo, B., Clark, G. M., McGuire, W. L., Moore, D., Fujita-Yamaguchi, Y., Vigneri, R., Goldfine, I. D., and Pezzino, V. Insulin-like growth factor-I receptors are overexpressed and predict a low risk in human breast cancer. Cancer Res, 53: 3736-3740, 1993.
7. Jiang, M., Shao, Z. M., Wu, J., Lu, J. S., Yu, L. M., Yuan, J. D., Han, Q. X., Shen, Z. Z., and Fontana, J. A. p21/waf1/cip1 and mdm-2 expression in breast carcinoma patients as related to prognosis. Int J Cancer, 74: 529-534, 1997.
8. Bhatavdekar, J. M., Patel, D. D., Shah, N. G., Vora, H. H., Suthar, T. P., Ghosh, N., Chikhlikar, P. R., and Trivedi, T. I. Prolactin as a local growth promoter in patients with breast cancer: GCRI experience. Eur J Surg Oncol, 26: 540-547., 2000.
9. Toropainen, E. M., Lipponen, P. K., and Syrjanen, K. J. Expression of insulin-like growth factor II in female breast cancer as related to established prognostic factors and long-term prognosis. Anticancer Res, 15: 2669-2674, 1995.
10. Santen, R. J., Song, R. X., McPherson, R., Kumar, R., Adam, L., Jeng, M. H., and Yue, W. The role of mitogen-activated protein (MAP) kinase in breast cancer. J Steroid Biochem Mol Biol, 80: 239-256., 2002.
11. Futreal, P. A., Liu, Q., Shattuck-Eidens, D., Cochran, C., Harshman, K., Tavtigian, S., Bennett, L. M., Haugen-Strano, A., Swensen, J., Miki, Y., and et al. BRCA1 mutations in primary breast and ovarian carcinomas. Science, 266: 120-122, 1994.
12. Chen, S., Zhou, D., Okubo, T., Kao, Y. C., and Yang, C. Breast tumor aromatase: functional role and transcriptional regulation. Endocr Relat Cancer, 6: 149-156., 1999.
13. Spitzer, E., Koepke, K., Kunde, D., and Grosse, R. EGF binding is quantitatively related to growth in node-positive breast cancer. Breast Cancer Res Treat, 12: 45-49, 1988.
14. Armes, J. E., Trute, L., White, D., Southey, M. C., Hammet, F., Tesoriero, A., Hutchins, A. M., Dite, G. S., McCredie, M. R., Giles, G. G., Hopper, J. L., and Venter, D. J. Distinct molecular pathogeneses of early-onset breast cancers in BRCA1 and BRCA2 mutation carriers: a population-based study. Cancer Res, 59: 2011-2017, 1999.
15. Reed, W., Fllrenes, V. A., Holm, R., Hannisdal, E., and Nesland, J. M. Elevated levels of p27, p21 and cyclin D1 correlate with positive oestrogen and progesterone receptor status in node-negative breast carcinoma patients. Virchows Arch, 435: 116-124, 1999.
16. Johnston, S. D., Liu, X., Zuo, F., Eisenbraun, T. L., Wiley, S. R., Kraus, R. J., and Mertz, J. E. Estrogen-related receptor alpha 1 functionally binds as a monomer to extended half-site sequences including ones contained within estrogen-response elements. Mol Endocrinol, 11: 342-352, 1997.
17. Périer, R. C., Praz, V., Junier, T., Bonnard, C., and Bucher, P. The eukaryotic promoter database (EPD). Nucleic Acids Res, 28: 302-303, 2000.
18. Yang, C., Zhou, D., and Chen, S. Modulation of aromatase expression in the breast tissue by ERR alpha-1 orphan receptor. Cancer Res, 58: 5695-5700, 1998.
19. Olayioye, M. A. Update on HER-2 as a target for cancer therapy: Intracellular signaling pathways of ErbB2/HER-2 and family members. Breast Cancer Res, 3: 385-389, 2001.
20. Pearson, G., Robinson, F., Beers Gibson, T., Xu, B. E., Karandikar, M., Berman, K., and Cobb, M. H. Mitogen-activated protein (MAP) kinase pathways: regulation and physiological functions. Endocr Rev, 22: 153-183., 2001.
21. Zhang, X. and Yee, D. Tyrosine kinase signalling in breast cancer: insulin-like growth factors and their receptors in breast cancer. Breast Cancer Res, 2: 170-175, 2000.

The present invention is not intended to be limited to the foregoing examples, but emcompasses all such modifications and variations as come within the scope of the appended claims.

We claim:

1. A method for determining breast cancer prognosis comprising the steps of:
   determining the level of estrogen-related receptor (ERR) α expression in breast cancer cells of a breast cancer patient; and
   comparing the ERRα level of the patient to a median ERRα level of a population of at least twenty-five breast cancer patients as expressed in their breast cancer cells wherein, on average, breast cancer patients with an ERRα level higher than the median level have a shorter survival time than breast cancer patients with an ERRα level lower than the median level.

2. A method for categorizing breast cancer patients based on ERRα status comprising the steps of measuring the expression level of ERRα in the breast cancer cells of a breast cancer patient and determining whether the expression level is high or low by comparing the ERRα level of the patient to a median ERRα level of a population of at least twenty-five breast cancer patients as expressed in their breast cancer cells.

3. The method of claim 2 further comprising the step of identifying a breast cancer patient as unlikely to respond to hormonal blockade therapy if the breast cancer cells express ERRα at a high level.

4. The method of claim 2 further comprising the step of identifying a breast cancer patient as likely to respond to hormonal blockade therapy if the breast cancer cells express ERRα at a low level.

5. The method of claim 2, wherein the expression level of ERRα is determined by measuring ERRα mRNA.

6. The method of claim 2, wherein the expression level of ERRα is determined by measuring ERRα protein.

7. The method of claim 2 further comprising the step of determining the expression level of estrogen receptor (ER)α in the breast cancer cells of a breast cancer patient.

8. The method of claim 7 further comprising the step of identifying a breast cancer patient as unlikely to respond to hormonal blockade therapy if the breast cancer cells express ERRα at a level higher than or similar to ERα.

9. The method of claim 7 further comprising the step of identifying a breast cancer patient as likely to respond to hormonal blockade therapy if the breast cancer cells express ERRα at a level lower than ERα.

10. The method of claim 7, wherein the expression level of at least one of ERRα and ERα is determined by measuring mRNA.

11. The method of claim 7, wherein the expression level of at least one of ERRα and ERα is determined by measuring protein.

12. The method of claim 2 further comprising the step of determining the expression level of ErbB2 in the breast cancer cells of a breast cancer patient.

13. The method of claim 12 further comprising the step of identifying a breast cancer patient as likely to respond to ErbB2-based therapy if the breast cancer cells of the patient express ErbB2 at a high level and ERRα at a high level.

14. The method of claim 12 further comprising the step of identifying a breast cancer patient as unlikely to respond to ErbB2-based therapy if the breast cancer cells of the patient express ErbB2 at a high level and ERRα at a low level.

15. The method of claim 12, wherein the expression level of at least one of ERRα and ErbB2 is determined by measuring mRNA.

16. The method of claim 12, wherein the expression level of at least one of ERRα and ErbB2 is determined by measuring protein.

* * * * *